(12) United States Patent
Babu et al.

(10) Patent No.: US 10,512,649 B2
(45) Date of Patent: Dec. 24, 2019

(54) METHODS AND COMPOSITIONS FOR TREATMENT OF ZIKA VIRUS INFECTION

(71) Applicant: Biocryst Pharmaceuticals, Inc., Durham, NC (US)

(72) Inventors: Yarlagadda S. Babu, Birmingham, AL (US); Pravin L. Kotian, Hoover, AL (US); Shanta Bantia, Birmingham, AL (US)

(73) Assignee: BioCryst Pharmaceuticals, Inc., Durham, NC (US)

(*) Notice: Subject to any disclaimer, the term of this patent is extended or adjusted under 35 U.S.C. 154(b) by 0 days.

(21) Appl. No.: 16/082,437

(22) PCT Filed: Mar. 6, 2017

(86) PCT No.: PCT/US2017/020961
§ 371 (c)(1),
(2) Date: Sep. 5, 2018

(87) PCT Pub. No.: WO2017/155886
PCT Pub. Date: Sep. 14, 2017

(65) Prior Publication Data
US 2019/0083496 A1     Mar. 21, 2019

Related U.S. Application Data

(60) Provisional application No. 62/304,317, filed on Mar. 6, 2016, provisional application No. 62/324,180, filed on Apr. 18, 2016, provisional application No. 62/368,111, filed on Jul. 28, 2016, provisional application No. 62/370,697, filed on Aug. 3, 2016, provisional application No. 62/411,867, filed on Oct. 24, 2016, provisional application No. 62/414,466, filed on Oct. 28, 2016, provisional application No. 62/462,852, filed on Feb. 23, 2017.

(51) Int. Cl.
*A61K 31/519* (2006.01)
*C07D 487/04* (2006.01)
*A61P 31/14* (2006.01)
*A61K 9/00* (2006.01)

(52) U.S. Cl.
CPC ........... *A61K 31/519* (2013.01); *A61P 31/14* (2018.01); *C07D 487/04* (2013.01); *A61K 9/0019* (2013.01); *A61K 9/0053* (2013.01)

(58) Field of Classification Search
CPC .................................................... A61K 31/519
USPC ........................................................ 514/265.1
See application file for complete search history.

(56) References Cited

U.S. PATENT DOCUMENTS

2015/0051230 A1   2/2015   Bantia

OTHER PUBLICATIONS

Young, Lee W., Written Opinion of Int'l Searching Authority (PCT/US17/020961), dated May 31, 2017.
CDC "Flaviviridae" Creat Date: Apr. 1, 2014 (Apr. 1, 2014) <https://www.cdc.gov/vhf/virus-families/flaviviridae.html.
Medicine.net "Zika Virus Infection" Create Date: Feb. 10, 2016 (Feb. 10, 2016) <http:/www.medicinenet.com/zika_virus_infection_symptons_and_signs/symptoms.htm>.
Gubler et al., "Dengue/Dengue Hemorrahagic Fever: The Emergence of a Global Health Problem" Emerging Infectious Diseases, Jun. 1995, vol. 1, pp. 55-57.
Warren, et al., "Protection against filovirus diseases by a novel broad-spectrum nucleoside analogue BCX4430" Nature, Mar. 2, 2014, vol. 508, pp. 402-411.
Julander, et al., "Efficacy of the broad-spectrum antiviral compound BCX4430 against Zika virus in cell culture and in a mouse model" Antiviral Research, Nov. 10, 2016, vol. 137, pp. 14-22.

*Primary Examiner* — Jeffrey H Murray
(74) *Attorney, Agent, or Firm* — Thomas G. Peterson; Maynard Cooper & Gale

(57) ABSTRACT

Disclosed are 9-deazaaadenine derivatives of the general formula (I)

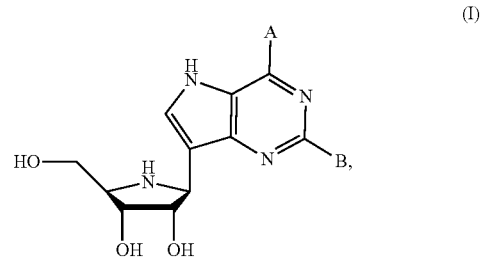

and pharmaceutically acceptable salts thereof, wherein A is OH or NH$_2$, and B is H or NH$_2$. Methods for treating, preventing and/or suppressing a Zika virus infection with the compounds disclosed are also provided. Pharmaceutical compositions comprising the disclosed compounds are also provided. Such pharmaceutical compositions may optionally contain one or more additional active agents.

22 Claims, 27 Drawing Sheets

Days post-virus infection

METHODS AND COMPOSITIONS FOR TREATMENT OF ZIKA VIRUS INFECTION

CROSS-REFERENCE TO RELATED APPLICATIONS

This application is a national stage under 35 U.S.C. 371 of International Application No. PCT/US2017/020961 having an international filing date of Mar. 6, 2017 (currently published). International Application No. PCT/US2017/020961 cites the priority of U.S. 62/304,317, filed Mar. 6, 2016; U.S. 62/324,180, filed Apr. 18, 2016; U.S. 62/368,111, filed Jul. 28, 2016; U.S. 62/370,697, filed Aug. 3, 2016; U.S. 62/411,867, filed Oct. 24, 2016; U.S. 62/414,466, filed Oct. 28, 2016; and U.S. 62/462,852, filed Feb. 23, 2017.

BACKGROUND

Viral diseases are responsible for both global pandemics and yearly seasonal epidemics such as influenza. Outbreaks may be characterized by potentiated virulence and may occur suddenly, resulting in serious morbidity and/or mortality. Importantly, viral diseases are not limited to humans. For example, influenza also affects livestock and birds, which may have significant impact on food supply in addition to increasing the risk of transmission to humans. Exemplary conditions related to viral infection include, for example, influenza, small pox, encephalitis, West Nile disease, yellow fever, Dengue fever, hepatitis, human immunodeficiency, polio, and Coxsackie.

SUMMARY OF THE DISCLOSURE

The present disclosure provides methods and compositions for inhibition of viral nucleic acid polymerases from Zika virus. The present disclosure also provides methods and compositions that are useful for treating, suppressing and/or preventing Zika virus infection in a subject. The present disclosure also provides methods and compositions that are useful for treating, suppressing and/or preventing a disease or condition resulting from a Zika virus infection in a subject.

The methods comprise administering to the subject an effective amount of a compound of the disclosure, or a composition comprising a compound of the disclosure and a pharmaceutically acceptable carrier. The method may optionally comprise administering to the subject one or more additional anti-viral agents.

These and other embodiments of the disclosure are further described in the following sections of the application, including the Detailed Description, Examples, and Claims.

Still other objects and advantages of the disclosure will become apparent to those of skill in the art from the disclosure herein, which is simply illustrative and not restrictive. Thus, other embodiments will be recognized by the skilled artisan without departing from the spirit and scope of the disclosure.

BRIEF DESCRIPTION OF THE FIGURES

FIG. 15C shows PRNT90 titers of neutralizing antibodies over time in Compound A treatment Groups 1 to 4 and control Group 5 following subcutaneous infection with Zika virus strain PRVABC-59.

FIG. 15D shows the maximum titer of Zika virus RNA by total dose (mg/kg) of Compound A administered in Groups 1-5.

DETAILED DESCRIPTION

Figure 1A:
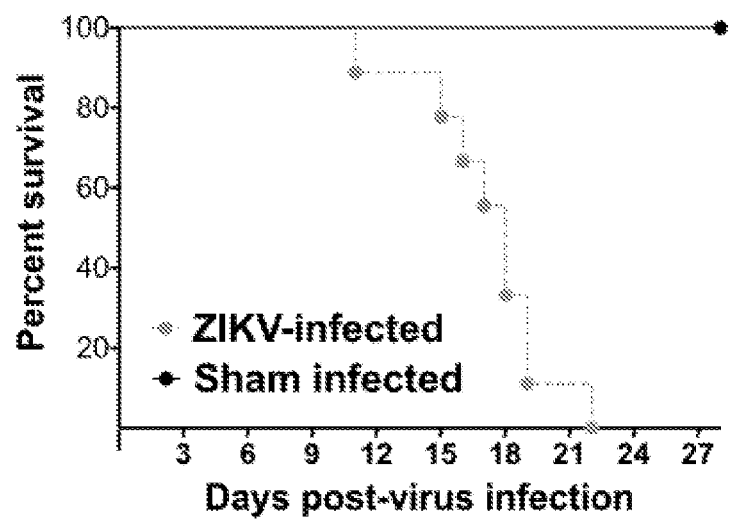
FIG. 1A shows the survival of AG129 mice exposed to a challenge dose of $10^3$ pfu/mouse Zika virus (Malaysian, strain P 6-740) as compared to sham-infected controls.

The Zika virus disease is caused by a virus transmitted by *Aedes* mosquitoes. Zika virus typically causes a mild disease in infected patients, such as skin rashes, conjunctivitis, muscle and joint pain, malaise, headache and arthralgia. This virus is rapidly emerging throughout the Americas, infecting millions of people in many different countries. While the majority of those infected do not display disease, more serious adverse events, including congenital disease or severe neurologic manifestations, have been associated with recent Zika outbreaks. Microcephaly appears to be the most dramatic and severe outcome associated with Zika virus infection during pregnancy. The virus has been detected in the placenta, amniotic fluid and fetal brain tissue in cases of congenital microcephaly and evidence suggests a causal relationship between Zika virus and microcephaly. Zika virus has also been isolated from amniotic fluid, semen or seminal fluid, urine and saliva of infected patients. These symptoms normally last for 2-7 days. There is no specific treatment or vaccine currently available. The virus is known to circulate in Africa, the Americas, Asia and the Pacific.

Zika virus was first identified in Uganda in 1947 in rhesus monkeys through a monitoring network of sylvatic yellow fever. It was subsequently identified in humans in 1952 in Uganda and the United Republic of Tanzania. Outbreaks of Zika virus disease have been recorded in Africa, the Americas, Asia and the Pacific. During large outbreaks in French Polynesia and Brazil in 2013 and 2015 respectively, national health authorities reported potential neurological and autoimmune complications of Zika virus disease. Recently in Brazil, local health authorities have observed an increase in Guillain-Barré syndrome which coincided with Zika virus infections in the general public, as well as an increase in babies born with microcephaly in northeast Brazil. Zika virus is transmitted to people through the bite of an infected mosquito from the *Aedes* genus, mainly *Aedes aegypti* in tropical regions. This is the same mosquito that transmits dengue, chikungunya and yellow fever. However, sexual transmission of Zika virus has been described in 2 cases, and the presence of the Zika virus in semen in 1 additional case. Zika virus disease outbreaks were reported for the first time from the Pacific in 2007 and 2013 (Yap and French Polynesia, respectively), and in 2015 from the Americas (Brazil and Colombia) and Africa (Cabo Verde). In addition, more than 13 countries in the Americas have reported sporadic Zika virus infections indicating rapid geographic expansion of Zika virus.

Unfortunately, developing an antiviral compound for the treatment of a pregnant woman to prevent or treat virus infection is difficult in regard to regulatory concerns and is hampered by justified concerns for the wellbeing of the mother and her developing fetus. Several precedents exists for treatment during pregnancy in the human immunodeficiency virus (HIV) field. In addition to the obvious treatment target of pregnant women, a more readily treatable group would be infected men that have the potential to transmit the virus to their sexual partners.

The structure of Zika virus follows that of other flaviviruses. It contains a nucleocapsid approximately 25-30 nm in diameter surrounded by a host-membrane derived lipid bilayer that contains envelope proteins E and M. The virion is approximately 40 inn in diameter with surface projections that measure roughly 5-10 nm. The surface proteins are arranged in an icosohedral-like symmetry. The reproductive cycle of Zika virus follows that of other known flaviviruses. First, the virion attaches to the host cell membrane receptors via the envelope protein which induces virion endocytosis. Next, the virus membrane fuses with the endosomal membrane and the ssRNA genome of the virus is released into the cytoplasm of the host cell. It is then translated into a polyprotein that is subsequently cleaved to faint all structural and non-structural proteins. Replication then takes place at intracellular compartments known as cytoplasmic viral factories in the endoplasmic reticulum resulting in a dsRNA genome. The dsRNA genome is then transcribed resulting in additional ssRNA genomes. Assembly then occurs within the endoplasmic reiticulum and the new virions are transported to the Golgi apparatus and then excreted into the intracellular space where the new virions can infect new host cells.

In a particular embodiment, the present invention relates to methods and compositions that are useful for treating, suppressing and/or preventing Zika viral infections in subjects. In another particular embodiment, the present invention relates to methods and compositions for treatment, suppression or and/or prevention of diseases or conditions relating to Zika virus infection in a subject. Such diseases or conditions relating to Zika virus infection include, but are not limited to, fever, skin rashes, conjunctivitis, muscle and joint pain, malaise, headache, neurological complications, auto-immune complications, Guillain-Barré syndrome and microcephaly, particularly pediatric microcephaly. In a particular embodiment, the present invention provides methods and compositions that are useful for reducing a viral titer of a Zika virus in a bodily fluid, tissue or cell of a subject. In a particular embodiment, the present invention provides methods and compositions for reducing or preventing the transmission of a Zika virus infection from a first subject to a second subject. In a particular embodiment, the present invention provides methods and compositions that are useful reducing or preventing the transmission of a Zika virus infection from a pregnant female to a prenatal human. The methods comprise administering to the subject an effective amount of a compound of the invention or a composition (such as a pharmaceutical composition) comprising a compound of the invention. The methods may optionally comprise administering one or more additional anti-viral agents.

Compounds of the Invention

The compounds of the disclosure are 9-deazaadenine derivatives generally known as immucillins, the syntheses of which are described, for example, in WO 03/80620, and by Evans et al., in Tetrahedron 2000, 56, 3053 and J. Org. Chem. 2001, 66(17), 5723 (each of which herein incorporated by reference in its entirety). Syntheses of similar structures are discussed, for example, in U.S. Pat. Nos. 5,985,848; 6,066,722; 6,228,741 and PCT publications WO 2003/080620 and 2008/030119 (each of which herein incorporated by reference in its entirety). Immucillin derivatives have been studied as purine nucleoside phosphorylase (PNP) inhibitors (See, Kicska et al., J. Biol. Chem. 2002, 277, 3219-3225, and Kicska et al., J. Biol. Chem. 2002, 277, 3226-3231; each of which herein incorporated by reference in its entirety). Some immucillins have also been studied as 5'-methylthioadenosine phosphorylase (MTAP) or 5'-methylthioadenosine nucleosidase (MTAN) inhibitors. Such mechanisms have been implicated in the treatment of cancer and bacterial infections (See, WO 03/080620, herein incorporated by reference in its entirety).

The compounds of the disclosure may exhibit tautomeric properties. Thus, the compounds of the disclosure also encompasses tautomeric forms of compounds of formula I, and mixtures thereof. It will further be appreciated that some compounds exist as pharmaceutically acceptable salts, solvates, and/or hydrates, each of which are also within the description of a compound of the disclosure.

The compounds of formula (I) are as follows:

(I)

wherein A is OH or $NH_2$, and B is H or $NH_2$.

Thus, in some embodiments of the compound of formula (I), A is $NH_2$.

In some embodiments of the compound of formula (I), B is $NH_2$.

In some embodiments of the compound of formula (I), A is OH.

In yet some embodiments of the compound of formula (I), B is H.

In still some embodiments of the compound of formula (I), A is $NH_2$ and B is H.

In still some embodiments of the compound of formula (I), A is OH and B is $NH_2$.

In still some embodiments of the compound of formula (I), A is $NH_2$ and B is $NH_2$.

In still some embodiments of the compound of formula (I), A is OH and B is H.

In a particularly preferred embodiment of the compound of formula (I), A is $NH_2$ and B is H.

The synthesis of compounds of the formula I is known in the art and is described, for example in PCT/US2011/056421, which is hereby incorporated by reference for such teaching.

The compounds of the disclosure may be prepared in different forms, such as salts, pharmaceutically acceptable salts, hydrates, solvates, or complexes, and the disclosure includes compositions and methods encompassing all variant forms of the compounds. In some embodiments, the compounds are prepared as hydrates or salts.

In some embodiments, the compounds of the disclosure exist as a pharmaceutically acceptable salt. In some embodiments, the salt form is about a 1:1 ratio of acid and compound of the disclosure. In some embodiments, the salt form is greater than about a 1:1 ratio of acid and compound of the disclosure. In some embodiments, the salt form is about a 2:1 ratio of acid and compound of the disclosure. In some embodiments, the salt form exists as a hydrate. In some embodiments, the compounds of the disclosure exist as a hydrate or solvate.

Abbreviations and Definitions

The term "compound(s) of the disclosure" or "compound(s) of the invention" as used herein means a compound of formula I, and may include salts (including pharmaceutically acceptable salts), tautomeric forms, hydrates and/or solvates thereof. In certain embodiments, a compound of the disclosure is compound A.

The term "compound A" as used herein means a compound of formula I where A is $NH_2$ and B is H, and may include salts (including pharmaceutically acceptable salts), tautomeric forms, hydrates and/or solvates thereof.

The term "solvate" as used herein means a compound of formula I, or a pharmaceutically acceptable salt thereof, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate."

A "pharmaceutical composition" refers to a mixture of one or more of the compounds of the disclosure, with other components, such as physiologically/pharmaceutically acceptable carriers and/or excipients. The purpose of a pharmaceutical composition is to facilitate administration of a compound of formula I, including salts, tautomeric forms, hydrates and/or solvates to a subject (including pharmaceutically acceptable forms of the foregoing).

The term "pharmaceutically acceptable salt" is intended to include salts derived from inorganic or organic acids including, for example hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluoroacetic, trichloroacetic, naphthalene-2 sulfonic and other acids. Pharmaceutically acceptable salt forms may also include forms wherein the ratio of molecules comprising the salt is not 1:1. For example, the salt may comprise more than one inorganic or organic acid molecule per molecule of base, such as two hydrochloric acid molecules per molecule of compound of formula I. As another example, the salt may comprise less than one inorganic or organic acid molecule per molecule of base, such as two molecules of compound of formula I per molecule of tartaric acid. Salts may also exist as solvates or hydrates.

The term "acid" contemplates all pharmaceutically acceptable inorganic or organic acids. Inorganic acids include mineral acids such as hydrohalic acids, such as hydrobromic and hydrochloric acids, sulfuric acids, phosphoric acids and nitric acids. Organic acids include all pharmaceutically acceptable aliphatic, alicyclic and aromatic carboxylic acids, dicarboxylic acids, tricarboxylic acids, and fatty acids. Preferred acids are straight chain or branched, saturated or unsaturated C1-C20 aliphatic carboxylic acids, which are optionally substituted by halogen or by hydroxyl groups, or C6-C12 aromatic carboxylic acids. Examples of such acids are carbonic acid, formic acid, fumaric acid, acetic acid, propionic acid, isopropionic acid, valeric acid, alpha-hydroxy acids, such as glycolic acid and lactic acid, chloro acetic acid, benzoic acid, methane sulfonic acid, and salicylic acid. Examples of dicarboxylic acids include oxalic acid, malic acid, succinic acid, tataric acid and maleic acid. An example of a tricarboxylic acid is citric acid. Fatty acids include all pharmaceutically acceptable saturated or unsaturated aliphatic or aromatic carboxylic acids having 4 to 24 carbon atoms. Examples include butyric acid, isobutyric acid, sec-butyric acid, lauric acid, palmitic acid, stearic acid, oleic acid, linoleic acid, linolenic acid, and phenylsteric acid. Other acids include gluconic acid, glycoheptonic acid and lactobionic acid.

The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

The term an "effective amount," "sufficient amount" or "therapeutically effective amount" as used herein is an amount of a compound that is sufficient to effect beneficial or desired results, including clinical results. As such, the effective amount may be sufficient, for example, to reduce or ameliorate the severity and/or duration of the viral infection, or one or more symptoms thereof, prevent the advancement of the viral infection, prevent the recurrence, development, or onset of one or more symptoms associated with the viral infection, prevent or reduce the replication or multiplication of a virus, prevent or reduce the production and/or release of a viral particle, enhance or otherwise improve the prophylactic or therapeutic effect(s) of another therapy. In certain embodiments, an effective amount is an amount of the compound of the disclosure that avoids or substantially attenuates undesirable side effects.

In certain embodiments, the "effective amount," "sufficient amount" or "therapeutically effective amount" in the context of a Zika virus infection is an amount sufficient to reduce one or more of the following steps of a the life cycle of the Zika virus: the docking of the virus particle to a cell, the introduction of viral genetic information into a cell, the expression of viral proteins, the translation of viral RNA, the transcription of viral RNA, the replication of viral RNA, the synthesis of new viral RNA, the production of new virus particles and the release of virus particles from a cell by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100%. In some embodiments, the "effective amount," "sufficient amount" or "therapeutically effective amount" in the context of a Zika virus infection reduces the replication, multiplication or spread of the Zika virus by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100%. In some embodiments, the "effective amount," "sufficient amount" or "therapeutically effective amount" in the context of a Zika virus infection increases the survival rate of infected subjects by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100%. In some embodiments, the "effective amount," "sufficient amount" or "therapeutically effective amount" in the context of a Zika virus infection decreases the rate of infants born with pediatric microcephaly by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100%. In each of the foregoing, when a reduction of increase is specified, such reduction of increase may be determined with respect to a subject that has not been treated with a compound of the disclosure.

The term, "treatment" is an approach for obtaining beneficial or desired results, including clinical results. Beneficial or desired clinical results may include, but are not limited to, alleviation or amelioration of one or more symptoms or conditions, diminution of extent of disease, a stabilized (i.e., not worsening) state of disease, preventing spread of disease, delay or slowing of disease progression, amelioration or palliation of the disease state and remission (whether partial or total), whether detectable or undetectable. "Treatment" can also mean prolonging survival as compared to expected survival if not receiving treatment.

The term "carrier" refers to a diluent, adjuvant, excipient, or vehicle with which a compound is administered. Non-limiting examples of such pharmaceutical carriers include liquids, such as water and oils, including those of petroleum, animal, vegetable or synthetic origin, such as peanut oil, soybean oil, mineral oil, sesame oil and the like. The pharmaceutical carriers may also be saline, gum acacia, gelatin, starch paste, talc, keratin, colloidal silica, urea, and the like. In addition, auxiliary, stabilizing, thickening, lubricating and coloring agents may be used. Other examples of suitable pharmaceutical carriers are described in "Remington's Pharmaceutical Sciences" by E. W. Martin; herein incorporated by reference in its entirety. The twits "animal," "subject" and "patient" as used herein include all members of the animal kingdom including, but not limited to, mammals, animals (e.g., cats, dogs, horses, swine, etc.) and humans. In certain embodiments, the subject is a human. In certain embodiments, the subject is a human of the female sex. In certain embodiments, the subject is a human of the female sex that is pregnant. In certain embodiments, the subject is a human of the female sex that is of child-bearing potential. In certain embodiments, the subject is a human of the male sex. In certain embodiments, the subject is a human of the male sex that is physiologically capable of fathering a child. In certain embodiments, the subject is sexually active. In some embodiments, the subject is an infant or a child. In some embodiments, the subject is a prenatal human (for example an embryo or a fetus, however, the prenatal human may be at any stage of development after fertilization)

The compounds of the invention are 9-deazaadenine derivatives generally known as immucillins, the syntheses of which are described, for example, in WO 03/80620, and by Evans et al., in Tetrahedron 2000, 56, 3053 and J. Org. Chem. 2001, 66(17), 5723 (each of which herein incorporated by reference in its entirety).

Syntheses of similar structures are discussed, for example, in U.S. Pat. Nos. 5,985,848; 6,066,722; 6,228,741 and PCT publications WO 2003/080620 and 2008/030119 (each of which herein incorporated by reference in its entirety). Immucillin derivatives have been studied as PNP inhibitors (See, Kicska et al., J. Biol. Chem. 2002, 277, 3219-3225, and Kicska et al., J. Biol. Chem. 2002, 277, 3226-3231; each of which herein incorporated by reference in its entirety). Some immucillins have also been studied as 5'-methylthioadenosine phosphorylase (MTAP) or 5'-methylthioadenosine nucleosidase (MTAN) inhibitors. Such mechanisms have been implicated in the treatment of cancer and bacterial infections (See, WO 03/080620, herein incorporated by reference in its entirety).

The compounds of the invention may exhibit tautomeric properties. Thus, the present invention also encompasses tautomeric forms of compounds of formula I, and mixtures thereof. It will further be appreciated that some compounds exist as pharmaceutically acceptable salts, solvates, and/or hydrates, each of which are also within the embodiments of the invention.

In some embodiments, the compounds of the invention exist as a pharmaceutically acceptable salt. In some embodiments, the salt form is about a 1:1 ratio of acid and compound of the invention. In some embodiments, the salt form is greater than about a 1:1 ratio of acid and compound of the invention. In some embodiments, the salt form is about a 2:1 ratio of acid and compound of the invention. In some embodiments, the salt form exists as a hydrate.

In some embodiments, the compounds of the invention exist as a hydrate or solvate.

When a Zika virus infection is presented in a subject along with another viral infection, the additional viral infection may be selected from a virus of the families retroviridae, adenoviridae, orthomyxoviridae, paramyxoviridae, arenaviridae, bunyaviridae, flaviviridae, Filoviridae, togaviridae, picornaviridae, poxviridae, hepadnaviridae, hepviridae, and coronaviridae. Specific viruses within these families include, but are not limited to, adenovirus, rhinovirus, hepatitis A, B, C, D and E, human immunodeficiency virus, polio, measles, Ebola, Coxsackie, West Nile, small pox, yellow fever, Dengue fever, influenza (including human, avian, and swine), lassa, lymphocytic choriomeningitis, junin, machupo, guanarito, hantavirus, Rift Valley Fever, La Crosse, Calif. encephalitis, Crimean-Congo, Marburg, Japanese Encephalitis, Kyasanur Forest, Venezuelan equine encephalitis, Eastern equine encephalitis, Western equine encephalitis, severe acute respiratory syndrome (SARS), parainfluenza, respiratory syncytial, Punta Toro, Tacaribe and pachinde. In a particular embodiment, the additional virus is a virus transmitted by a mosquito of the *Aedes* genus, such as, but not limited to, Dengue fever, chikungunya and yellow fever.

In some embodiments, the compounds of the invention are used to inhibit the replication or infectivity of a Zika virus. In some embodiments, the compounds of the invention are used to inhibit the expression of viral proteins, the translation of viral RNA, the transcription of viral RNA, the replication of viral RNA, the synthesis of new viral RNA, the production of new virus particles or the release of virus particles from a cell. In some embodiments, the compounds of the invention are used to inhibit the growth of a cell infected with a Zika virus.

In some embodiments, the present invention provides a method for inhibiting a Zika virus RNA polymerase in a subject comprising administering to said subject an effective amount of a compound of the invention, including but not limited to, compound A.

According to the Baltimore classification system, RNA polymerase viruses may be classified into groups such as, but not limited to, double-stranded viruses, positive-sense single-stranded viruses, and negative-sense single stranded viruses. Positive-sense single-stranded families include, for example, coronaviridae, picornaviridae, togaviridae, flaviviridae, and the like. Negative-sense single-stranded families include, for example, paramyxoviridae, arenaviridae, bunyaviridae, orthomyxoviridae, filoviridae, and the like. Each of the virus families may be further classified into genera, species, and serotype (or subtype). Other designations for taxonomic designations of viruses are set forth by the classification guidelines according to the International Committee on Taxonomy of Viruses.

RNA-dependent RNA polymerase catalyzes viral RNA transcription and replication. Because the transcription and replication of the virus depends on the activity of RNA polymerase, this enzyme has become of interest as a target for development of new anti-viral compounds in the wake of the recent emergence of drug resistant viruses. Viruses may develop resistance to one drug upon treatment, thus decreasing the efficacy of the drug and requiring the subject to be treated with another antiviral drug. A drug or treatment that exhibits simultaneous efficacy against a broad spectrum of viral strains would thus be useful.

In addition, the compositions or methods described herein may further comprise one or more additional anti-viral agents in combination with a compound of the invention. Examples of such anti-viral agents include, but are not limited to, cytovene, ganciclovir, trisodium phosphonoformate, ribavirin, interferon, d4T, ddI, AZT, amantadine, rimandatine, and other anti-influenza agents; acyclovir, and related agents, foscarnet and other anti-herpes virus agents.

In some embodiments, an additional anti-viral agent is an anti-influenza agent. In some embodiments, an additional anti-viral agent is a neuraminidase inhibitor. In some embodiments, an additional anti-viral agent is selected from the group consisting of laninamivir, oseltamivir, zanamivir, and peramivir. In some embodiments, an additional antiviral agent is peramivir. In some embodiments, an additional anti-viral agent is laninamivir. In some embodiments, an additional anti-viral agent is oseltamivir. In some embodiments, an additional anti-viral agent is zanamivir.

Compounds that relate to inhibition of influenza polymerase are described, for example, in U.S. Pat. Nos. 7,388,002; 7,560,434; and in U.S. patent application Ser. No. 12/440,697 (published as U.S. Patent Publication No. 20100129317); and Ser. No. 12/398,866 (published as U.S. Patent Publication No. 20090227524), each of which herein incorporated by reference in its entirety. Currently, there is one influenza polymerase inhibitor in clinical trials, known as T-705 (favipiravir; 6-fluoro-3-hydroxy-2-pyrazinecarboxamide). T-705 possesses potent and broad spectrum antiviral activity against multiple strains of influenza virus infection in vitro and in vivo (Kiso et al., PNAS 2010, 107, 882-887; herein incorporated by reference in its entirety). T-705 is characterized by a mechanism of action that is different from most anti-influenza viral drugs.

Another class of compounds used as anti-virals are M2 inhibitors (See, Pielak, R., Schnell, J., & Chou, J. (2009) Proceedings of the National Academy of Sciences, 106 (18), 7379-7384 (herein incorporated by reference in its entirety). Exemplary members of this class include amantadine and rimantadine.

In some embodiments, the compositions of the invention further comprise two additional anti-viral agents and the methods of the invention further comprise administration of two additional anti-viral agents. In some embodiments, the additional anti-viral agents are a neuraminidase inhibitor and an M2 inhibitor. In some embodiments, the additional anti-viral agents are selected from the groups consisting of 1) laninamivir, oseltamivir, zanamivir, and peramivir; and 2) amantadine and rimandatine. In some embodiments, the additional antiviral agents are peramivir and amantadine. In some embodiments, the additional antiviral agents are peramivir and rimantadine.

Thus, in some embodiments, the composition of the invention further comprise one or more additional anti-viral agents and the methods of the invention further comprise administration of one or more additional anti-viral agents.

The present invention provides methods for inhibiting a Zika virus RNA polymerase comprising contacting the polymerase with an effective amount of a compound of the invention.

In some embodiments, the present invention provides a method for treating a subject suffering from a Zika virus infection comprising administering to said subject an effective amount of a compound of the invention. In some embodiments, the present invention provides a method for suppressing a Zika virus infection in a subject comprising administering to the subject an effective amount of a compound of the invention. In some embodiments, the present invention provides a method for preventing a Zika virus infection in a subject comprising administering to the subject an effective amount of a compound of the invention.

In some embodiments, the present invention provides a method for treating, suppressing and/or preventing a disease or condition relating to Zika virus infection which comprises administering to said subject an effective amount of a compound of the invention. Such diseases or conditions relating to Zika virus infection include, but are not limited to, fever, skin rashes, conjunctivitis, muscle and joint pain, malaise, headache, neurological complications, auto-immune complications, Guillain-Barré syndrome and microcephaly, particularly pediatric microcephaly.

In some embodiments, the present invention provides a method for reducing viral titer for Zika virus in a bodily fluid, tissue or cell of a subject comprising contacting said fluid, tissue or cell with a compound of the invention. In some embodiments, the present invention provides a method for reducing viral titer for Zika virus in a bodily fluid, tissue or cell of a subject, the method comprising administering an effective amount of a compound of the invention to the subject. Such bodily fluids include, but are not limited to, blood, blood plasma, blood serum, amniotic fluid, breast milk, semen, seminal fluid, vaginal secretions, cerebrospinal fluid, urine or saliva (or a combination of the foregoing). In the foregoing embodiments, the tissue may an embryo, a fetus, placenta, liver, kidney, spleen, brain, testis or uterus (or a combination of the foregoing). In certain embodiments, the transmission of Zika virus (for example, from a subject infected with Zika virus to a subject that is not yet infected) is reduced.

In some embodiments, the present invention provides a method for reducing or preventing the transmission of a Zika virus infection from a first subject to a second subject which comprises administering to said first subject an effective amount of a compound of the invention. In certain embodiments, such reduction or prevention is obtained, at least in part, by reducing the viral titer of a Zika virus in a bodily fluid of the first subject. In certain embodiments, the first subject is a male. In certain embodiments, the first subject is a female. In certain embodiments, the second subject is a family member or acquaintance of the first subject. In certain embodiments, the second subject is a sexual partner of the first subject. In certain embodiments, the second subject is an infant or child (for example, a subject under the age of 16 years).

In certain embodiments, the second subject is a prenatal human (for example, an embryo or a fetus; however, the prenatal human may be at any stage of development after fertilization). In certain embodiments, the first subject is a female and the second subject is an infant, child or a prenatal human.

In certain embodiments, the Zika virus infection is transmitted from the first subject to the second subject through transmission of a bodily fluid of the first subject to the second subject. Such bodily fluids include, but are not limited to, blood, blood plasma, blood serum, amniotic fluid, breast milk, semen, seminal fluid, vaginal secretions, cerebrospinal fluid, urine or saliva.

In certain embodiments, the second subject is a family member or acquaintance of the first subject and the Zika virus is transmitted to the second subject through an interaction of the first subject and the second subject. In certain embodiments, the second subject is a sexual partner of the first subject and the Zika virus is transmitted from the first subject to the second subject by a bodily fluid, such as, but not limited to, semen, seminal fluid, vaginal secretions, blood or saliva (or a combination of the foregoing). In certain embodiments, the first subject is female and the second subject is an infant or child and the Zika virus is transmitted from the first subject to the second subject by a bodily fluid, such as, but not limited to, breast milk, blood or saliva (or a combination of the foregoing). In certain embodiments, the first subject is female and the second subject is a prenatal human (such as an embryo or fetus; however, the prenatal human may be at any stage of development after fertilization) and the Zika virus is transmitted from the first subject to the second subject by a bodily fluid, such as, but not limited to, amniotic fluid.

In certain embodiments, the compound of the invention is administered to the first subject before the first subject has been infected with the Zika virus infection, after the first subject has been infected with the Zika virus infection or after the first subject has been infected with the Zika virus and before the Zika virus infection can be detected.

In some embodiments, the present invention provides a method for reducing or preventing the transmission of a suspected or an actual Zika virus infection from a first subject to a second subject which comprises administering to said second subject an effective amount of a compound of the invention. In certain embodiments, such reduction or prevention is obtained, at least in part, by preventing or suppressing a Zika virus infection in the second subject. In certain embodiments, such reduction or prevention is obtained, at least in part, by reducing the viral titer of a Zika virus in a bodily fluid of the second subject such that a Zika virus infection in the second subject, if such infection occurs, is not likely to be spread further by the second subject. In certain embodiments, such reduction or prevention is obtained, at least in part, by reducing the viral titer of a Zika virus in a bodily fluid of the second subject such that a Zika virus infection in the second subject, if such infection initially occurs, it can be eliminated physiologically (for example, by the immune system) by the second subject, either with or without the administration of additional therapeutic compounds. In certain embodiments, the first subject is a male. In certain embodiments, the first subject is suspected of having a Zika virus infection (for example, the first subject may have travelled to a region where Zika virus infections have been documented). Therefore, in certain embodiments, the Zika virus infection is a suspected Zika virus infection. In certain embodiments, the first subject has a Zika virus infection (including a Zika virus infection that cannot be detected by current diagnostic methods at the time and a Zika virus infection that is active and can be detected by current diagnostic methods). Therefore, in certain embodiments, the Zika virus infection is an actual Zika virus infection. In certain embodiments, the first subject is a female. In certain embodiments, the second subject is a family member or acquaintance of the first subject. In certain embodiments, the second subject is a sexual partner of the first subject. In certain embodiments, the second subject is an infant or child (for example, a subject under the age of 16 years). In certain embodiments, the first subject is a female and the second subject is an infant or a child.

In certain embodiments, the Zika virus infection is transmitted from the first subject to the second subject through transmission of a bodily fluid of the first subject to the second subject. Such bodily fluids include, but are not limited to, blood, blood plasma, blood serum, amniotic fluid, breast milk, semen, seminal fluid, vaginal secretions, cerebrospinal fluid, urine or saliva.

In certain embodiments, the second subject is a sexual partner of the first subject and the Zika virus is transmitted from the first subject to the second subject by a bodily fluid, such as, but not limited to, semen, seminal fluid, vaginal secretions, blood or saliva (or a combination of the foregoing). In certain embodiments, the first subject is female and the second subject is an infant or child and the Zika virus is transmitted from the first subject to the second subject by a bodily fluid, such as, but not limited to, breast milk, blood or saliva (or a combination of the foregoing). In certain embodiments, the second subject is a family member or acquaintance of the first subject and the Zika virus is transmitted to the second subject through an interaction of the first subject and the second subject.

In certain embodiments, the compound of the invention is administered to the second subject before the first subject has been infected with the Zika virus infection, after the first subject has been infected with the Zika virus infection or after the first subject has been infected with the Zika virus and before the Zika virus infection can be detected.

In some embodiments, the present invention provides a method for reducing or preventing the transmission of a Zika virus infection from a pregnant female to a prenatal human which comprises administering to said subject an effective amount of a compound of the invention. In certain embodiments, such reduction or prevention is obtained, at least in part, by reducing the viral titer of a Zika virus in a bodily fluid of the female. In certain embodiments, the prenatal human is an embryo or a fetus (however, the prenatal human may be at any stage of development after fertilization).

In certain embodiments, the Zika virus is transmitted from the pregnant female to the prenatal human by a bodily fluid, such as, but not limited to, amniotic fluid, blood, blood plasma or blood serum.

In certain embodiments, the compound of the invention is administered to the pregnant female before the pregnant female has been infected with the Zika virus infection, after the pregnant female has been infected with the Zika virus infection or after the pregnant female has been infected with the Zika virus and before the Zika virus infection can be detected. In certain embodiments, the compound of the invention is administered to the pregnant female before fertilization, after fertilization and before embryogenesis or after embryogenesis.

In some embodiments, the present invention provides a method for treating a subject who is at risk for developing a Zika virus infection, which comprises administering to the subject an effective amount of a compound of the invention. In certain embodiments, such treating is obtained, at least in part, by treating, preventing or suppressing a Zika virus infection in the subject. In certain embodiments, such treating is obtained, at least in part, by reducing the viral titer of a Zika virus in a bodily fluid of the subject such that a Zika virus infection in the subject, if such infection initially occurs, is not likely to be spread further by the subject. In certain embodiments, such treating is obtained, at least in part, by reducing the viral titer of a Zika virus in a bodily fluid of the subject such that a Zika virus infection in the subject, if such infection initially occurs, it can be eliminated physiologically (for example, by the immune system) by the subject, either with or without the administration of additional therapeutic compounds. In certain embodiments, the subject is a male. In certain embodiments, the subject is a female. In certain embodiments, the subject is at risk as a result of traveling to a region where Zika virus infections have been documented. In certain embodiments, the subject is at risk as a result of having contact with a person who has travelled to a region where Zika virus infections have been documented. In certain embodiments, the subject is at risk as a result of having contact with a person who has a Zika virus infection (including a Zika virus infection that cannot be detected). In certain embodiments, the subject is at risk as a result of having contact with a person who is at risk of developing a Zika virus infection (for example, as a result of traveling to a region where Zika virus infections have been documented). In certain embodiments, the subject is a family member or acquaintance of a person who has a Zika virus infection or is at risk of having a Zika virus infection. In certain embodiments, the subject is a sexual partner of a person who has a Zika virus infection or is at risk of having a Zika virus infection. In certain embodiments, the subject is an infant or child (for example, a subject under the age of 16 years) who has a caregiver or parent who has a Zika virus infection or is at risk of having a Zika virus infection.

In certain embodiments, the compound of the invention is administered to the subject before the subject has been infected with the Zika virus infection. In certain embodiments, the compound of the invention is administered to the subject before the subject has been placed at risk of contracting a Zika virus infection. In certain embodiments, the compound of the invention is administered to the subject after the subject has been placed at risk of contracting a Zika virus infection.

In some embodiments, the viral infection comprises infection by Zika virus and by one or more additional viruses.

In some embodiments, the additional viral infection is an infection selected from a viruses of the families retroviridae, adenoviridae, orthomyxoviridae, paramyxoviridae, arenaviridae, bunyaviridae, flaviviridae, filoviridae, togaviridae, picomaviridae, poxviridae, hepadnaviridae, hepviridae, and coronaviridae. Specific viruses within these families include, but are not limited to, adenovirus, rhinovirus, hepatitis A, B, C, D and E, human immunodeficiency virus, polio, measles, Ebola, Coxsackie, West Nile, small pox, yellow fever, Dengue fever, influenza (including human, avian, and swine), lassa, lymphocytic choriomeningitis, junin, machupo, guanarito, hantavirus, Rift Valley Fever, La Crosse, Calif. encephalitis, Crimean-Congo, Marburg, Japanese Encephalitis, Kyasanur Forest, Venezuelan equine encephalitis, Eastern equine encephalitis, Western equine encephalitis, severe acute respiratory syndrome (SARS), parainfluenza, respiratory syncytial, Punta Toro, Tacaribe and pachinde. In a particular embodiment, the additional virus is a virus transmitted by a mosquito of the *Aedes* genus, such as, but not limited to, Dengue fever, chikungunya and yellow fever.

In some embodiments, the methods described herein comprise the steps of: i) optionally identifying a subject in need; (ii) optionally providing a compound of the invention or a pharmaceutical composition comprising a compound of the invention; and (iii) administering said compound or composition in an effective amount. Such administration may be used to inhibit a Zika virus RNA polymerase, to treat a subject suffering from a Zika virus infection or suspected of being at risk for a Zika virus infection, to prevent a Zika virus infection in a subject, to suppress a Zika virus infection in a subject or to treat, suppress or prevent a disease or condition relating to Zika virus infection and/or to reduce a viral titer of Zika virus in a bodily fluid, tissue or cell of the subject.

In some embodiments, the methods described herein comprise administering the compound of the invention at an effective amount (such as is described herein). In some embodiments, the methods described herein comprise administering a compound of the invention at an effective amount per day (such as is described herein). Suitable effective amounts are described in more detail herein. In some embodiments, the methods described herein comprise administering a single dose of a compound of the invention during a course of treatment (where the dose may contain an effective amount of a compound of the invention). Such dose may be administered in a single administration (q.d.) or such dose may be administered in multiple administration on the same day (such as but not limited to b.i.d. or t.i.d.). In some embodiments, the methods described herein comprise administering more than one dose of a compound of the invention during a course of treatment (where the dose may contain an effective amount of a compound of the invention). Each dose may be administered in a single administration (q.d.) or such dose may be administered in multiple administration on the same day (such as but not limited to bid. or t.i.d.). The amount of a compound of the invention in each dose administered during a course of treatment is not required to be the same. For example, in some embodiments a course of treatment comprises administering at least one loading dose and at least one maintenance dose, wherein the loading dose contains a greater amount of a compound of the invention as compared to the maintenance dose (such as, but not limited to, 2 to 10 times higher). Dosing is described in more details herein.

In some embodiments, the disclosure provides for the use of pharmaceutical compositions and/or medicaments comprising a compound of the invention in any of the methods described herein.

In some embodiments, the treatment efficacy results from the inhibition of a viral RNA polymerase. In some embodiments, the treatment efficacy results from inhibiting viral polymerases from one or more virus family.

In some embodiments, the method is performed in vivo. In some embodiments, the method is performed in vitro. In some embodiments, the method is performed ex vivo.

In some embodiments, the subject is a mammal. In some embodiments, the subject is a human. In some embodiments, the subject is avian. In some embodiments, the subject is a swine or pig. In some embodiments, the subject is a human of the male sex. In some embodiments, the subject is a human of the female sex. In some embodiments, the subject is a human of the female sex that is pregnant. In some embodiments, the subject is a human of the female sex that is of child-bearing potential. In certain embodiments, the subject is a human of the male sex that is physiologically capable of fathering a child. In certain embodiments, the subject is sexually active. In some embodiments, the subject is an infant or a child. In some embodiments, the subject is a prenatal human (for example an embryo or a fetus, however, the prenatal human may be at any stage of development after fertilization).

In some embodiments, the bodily fluid is blood. In some embodiments, the bodily fluid is plasma. In some embodiments, the bodily fluid is blood serum. In some embodiments, the bodily fluid is semen or seminal fluid. In some embodiments, the bodily fluid is a vaginal secretion. In some embodiments, the bodily fluid is cerebrospinal fluid. In some embodiments, the bodily fluid is urine. In some embodiments, the bodily fluid is saliva. In some embodiments, the bodily fluid is breast milk. In some embodiments, the bodily fluid is amniotic fluid.

In some embodiments, the compound or composition is administered intravenously, interperitonealy, parenterally, intramuscularly or orally.

In some embodiments, the compound or composition is administered intravenously.

In some embodiments, the compound or composition is administered intraperitonealy.

In some embodiments, the compound or composition is administered parenterally.

In some embodiments, the compound or composition is administered intramuscularly.

In some embodiments, the compound or composition is administered orally.

In certain embodiments, the methods comprise administering to the subject an effective amount of a compound of the invention, or a composition, such as a pharmaceutical composition, comprising a compound of the invention and a pharmaceutically acceptable carrier.

The compounds of the present invention may be prepared in different forms, such as salts, hydrates, solvates, tautomers or complexes, and the invention includes methods encompassing all variant forms of the compounds.

In some embodiments, the methods of the invention comprise pharmaceutically acceptable salts of a compound of the invention. A compound the invention may be formulated as a pharmaceutically acceptable salt, e.g., acid addition salt, and complexes thereof. The preparation of such salts can facilitate the pharmacological use by altering the physical characteristics of the agent without preventing its physiological effect. Examples of useful alterations in physical properties include, but are not limited to, lowering the melting point to facilitate transmucosal administration and increasing the solubility to facilitate administering higher concentrations of the drug.

In preferred embodiments of the methods described herein, the compound of the invention is Compound A.

The methods of the invention may be carried out both in vitro and in vivo systems, including, for example, with isolated or cultured cells or tissues, non-cellular in vitro assay systems and animals (e.g., an amphibian, a bird, a fish, a mammal, a marsupial, a human, a domestic animal such as, but not limited to, a cat, dog, monkey, mouse or rat; or a commercial animal such as, but not limited to, a cow or pig).

Pharmaceutical Compositions

The compounds of the disclosure may be formulated into pharmaceutical compositions for administration to subjects in a biologically compatible form suitable for administration in vivo. The present disclosure provides a pharmaceutical composition comprising compounds of the disclosure in admixture with a pharmaceutically acceptable carrier. The pharmaceutically-acceptable carrier must be acceptable in the sense of being compatible with the other ingredients of the composition and not deleterious to the recipient thereof. The pharmaceutically-acceptable carriers employed herein may be selected from various organic or inorganic materials that are used as materials for pharmaceutical formulations and which are incorporated as analgesic agents, buffers, binders, disintegrants, diluents, emulsifiers, excipients, extenders, glidants, solubilizers, stabilizers, suspending agents, tonicity agents, vehicles and viscosity-increasing agents. Pharmaceutical additives, such as antioxidants, aromatics, colorants, flavor-improving agents, preservatives, and sweeteners, may also be added. Examples of acceptable pharmaceutical carriers include carboxymethyl cellulose, crystalline cellulose, glycerin, gum arabic, lactose, magnesium stearate, methyl cellulose, powders, saline, sodium alginate, sucrose, starch, talc and water, among others. In some embodiments, the term "pharmaceutically acceptable" means approved by a regulatory agency of the Federal or a state government or listed in the U.S. Pharmacopeia or other generally recognized pharmacopeia for use in animals, and more particularly in humans.

Often, the pharmaceutically acceptable carrier is chemically inert toward the active compounds and is non-toxic under the conditions of use. Examples of pharmaceutically acceptable carriers may include, for example, water or saline solution, polymers such as polyethylene glycol, carbohydrates and derivatives thereof, oils, fatty acids, or alcohols. In some embodiments, the carrier is saline or water. In some embodiments, the carrier is saline. In some embodiments, the carrier is water.

Surfactants such as, but not limited to, detergents, are also suitable for use in the formulations. Specific examples of surfactants include polyvinylpyrrolidone, polyvinyl alcohols, copolymers of vinyl acetate and of vinylpyrrolidone, polyethylene glycols, benzyl alcohol, mannitol, glycerol, sorbitol or polyoxyethylenated esters of sorbitan; lecithin or sodium carboxymethylcellulose; or acrylic derivatives, such as methacrylates and others, anionic surfactants, such as alkaline stearates, in particular sodium, potassium or ammonium stearate; calcium stearate or triethanolamine stearate; alkyl sulfates, in particular sodium lauryl sufate and sodium cetyl sulfate; sodium dodecylbenzenesulphonate or sodium dioctyl sulphosuccinate; or fatty acids, in particular those derived from coconut oil, cationic surfactants, such as water-soluble quaternary ammonium salts of formula $N^+R'R''R'''R''''Y^-$, in which the R radicals are identical or different optionally hydroxylated hydrocarbon radicals and $Y^-$ is an anion of a strong acid, such as halide, sulfate and sulfonate anions; cetyltrimethylammonium bromide is one of the cationic surfactants which can be used, amine salts of formula $R^+R'R''R'''$, in which the R radicals are identical or different optionally hydroxylated hydrocarbon radicals; octadecylamine hydrochloride is one of the cationic surfactants which can be used, non-ionic surfactants, such as optionally polyoxyethylenated esters of sorbitan, in particular Polysorbate 80, or polyoxyethylenated alkyl ethers; polyethylene glycol stearate, polyoxyethylenated derivatives of castor oil, polyglycerol esters, polyoxyethylenated fatty alcohols, polyoxyethylenated fatty acids or copolymers of ethylene oxide and of propylene oxide, amphoteric surfactants, such as substituted lauryl compounds of betaine, When administered to a subject, the compounds of the disclosure and pharmaceutically acceptable carriers may be sterile. In some embodiments, water is a carrier when the compound of the disclosure is administered intravenously. In some embodiments, the carrier is a saline solution when the compound of the disclosure I is administered intravenously. Aqueous dextrose and glycerol solutions may also be employed as liquid carriers, particularly for injectable solutions. Suitable pharmaceutical carriers may also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, polyethylene glycol 300, water, ethanol, polysorbate 20, and the like. The present compositions, if desired, may also contain minor amounts of wetting or emulsifying agents, or pH buffering agents.

The pharmaceutical formulations of the present disclosure are prepared by methods well-known in the pharmaceutical arts. For example, the compounds of the disclosure are brought into association with a carrier and/or diluent, as a suspension or solution. Optionally, one or more accessory ingredients (e.g., buffers, flavoring agents, surface active agents, and the like) also are added. The choice of carrier is determined by the solubility and chemical nature of the compounds, chosen route of administration and standard pharmaceutical practice. In some embodiments, the formulation comprises a compound of the disclosure and water. In some embodiments, the formulation comprises a compound of the disclosure and saline.

Additionally, the compounds of the disclosure are administered to a subject, such as a human or animal subject, by known procedures including, without limitation, oral administration, sublingual or buccal administration, parenteral administration, transdermal administration, via inhalation or intranasally, vaginally, rectally, and intramuscularly. The compounds of the disclosure may be administered parenterally, by epifascial, intracapsular, intracranial, intracutaneous, intrathecal, intramuscular, intraorbital, intraperitoneal, intraspinal, intrasternal, intravascular, intravenous, parenchymatous, subcutaneous or sublingual injection, or by way of catheter. In some embodiments, the compounds of the disclosure are administered to the subject by way of intramuscular delivery. In some embodiments, the compounds of the disclosure are administered to the subject by way of intraperitoneal delivery. In some embodiments, the compounds of the disclosure are administered to the subject by way of intravenous delivery. In some embodiments, the compounds of the disclosure are administered orally. In certain embodiments, the compounds of the disclosure are administered by bolus administration, for example an IV or IM bolus administration.

For oral administration, a formulation of the compound of the disclosure may be presented as capsules, tablets, powders, granules, or as a suspension or solution. Capsule formulations may be gelatin, soft-gel or solid. Tablets and capsule formulations may further contain one or more adjuvants, binders, diluents, disintegrants, excipients, fillers, or lubricants, each of which are known in the art. Examples of such include carbohydrates such as lactose or sucrose, dibasic calcium phosphate anhydrous, corn starch, mannitol, xylitol, cellulose or derivatives thereof, microcrystalline cellulose, gelatin, stearates, silicon dioxide, talc, sodium starch glycolate, acacia, flavoring agents, preservatives, buffering agents, disintegrants, and colorants. Orally administered compositions may contain one or more optional agents such as, but not limited to, sweetening agents such as fructose, aspartame or saccharin; flavoring agents such as peppermint, oil of wintergreen, or cherry; coloring agents; and preservative agents, to provide a pharmaceutically palatable preparation.

For parenteral administration (i.e., administration by injection through a route other than the alimentary canal), the compounds of the disclosure may be combined with a sterile aqueous solution that is isotonic with the blood of the subject. Such a formulation is prepared by dissolving a solid active ingredient in water containing physiologically-compatible substances, such as sodium chloride, glycine and the like, and having a buffered pH compatible with physiological conditions, so as to produce an aqueous solution, then rendering said solution sterile. The formulation may be presented in unit or multi-dose containers, such as sealed ampules or vials. The formulation may be delivered by any mode of injection, including, without limitation, epifascial, intracapsular, intracranial, intracutaneous, intrathecal, intramuscular, intraorbital, intraperitoneal, intraspinal, intrasternal, intravascular, intravenous, parenchymatous, subcutaneous, or sublingual or by way of catheter into the subject's body.

Parenteral administration includes aqueous and non-aqueous based solutions. Examples of which include, for example, water, saline, aqueous sugar or sugar alcohol solutions, alcoholic (such as ethyl alcohol, isopropanol, glycols), ethers, oils, glycerides, fatty acids, and fatty acid esters. In some embodiments, water is used for parenteral administration. In some embodiments, saline is used for parenteral administration. Oils for parenteral injection include animal, vegetable, synthetic or petroleum based oils. Examples of sugars for solution include sucrose, lactose, dextrose, mannose, and the like. Examples of oils include mineral oil, petrolatum, soybean, corn, cottonseed, peanut, and the like. Examples of fatty acids and esters include oleic acid, myristic acid, stearic acid, isostearic acid, and esters thereof.

For transdermal administration, the compounds of the disclosure are combined with skin penetration enhancers, such as propylene glycol, polyethylene glycol, isopropanol, ethanol, oleic acid, N-methylpyrrolidone and the like, which increase the permeability of the skin to the compounds of the disclosure and permit the compounds to penetrate through the skin and into the bloodstream. The compound/enhancer compositions also may be further combined with a polymeric substance, such as ethylcellulose, hydroxypropyl cellulose, ethylene/vinylacetate, polyvinyl pyrrolidone, and the like, to provide the composition in gel form, which are dissolved in a solvent, such as methylene chloride, evaporated to the desired viscosity and then applied to backing material to provide a patch.

In some embodiments, the compounds of the disclosure are in unit dose form such as a tablet, capsule or single-dose vial. Suitable unit doses, i.e., an effective amount, may be determined during clinical trials designed appropriately for each of the conditions for which administration of a chosen compound is indicated and will, of course, vary depending on the desired clinical endpoint.

The present disclosure also provides articles of manufacture for treating and preventing disorders, such as viral disorders, in a subject. The articles of manufacture comprise a compound of the disclosure or a pharmaceutical composition comprising a compound of the disclosure, optionally further containing at least one additional antiviral compound, as described herein. The articles of manufacture may be packaged with indications for various disorders that the pharmaceutical compositions are capable of treating and/or preventing. For example, the articles of manufacture may comprise a unit dose of a compound of the disclosure that is capable of treating or preventing a certain disorder, and an indication that the unit dose is capable of treating or preventing a certain disorder, for example a Zika virus infection.

Dosage and Administration

In accordance with the methods of the present disclosure, the compounds of the disclosure are administered to the subject (or are contacted with cells of the subject) in an effective amount. This amount is readily determined by the skilled artisan, based upon known procedures, including analysis of titration curves established in vivo and methods and assays disclosed herein. In some embodiments, an effective amount decreases the level of Zika virus in the subject and/or limits or prevents an increase in the level of viral particles in the subject. In some embodiments, an effective amount decreases the viral titer of Zika virus in a bodily fluid of the subject. In some embodiments, an effective amount inhibits the activity of Zika virus viral polymerase in the subject, such as a viral RNA polymerase.

In certain embodiments, the effective amount of a compound of the disclosure ranges from about 0.01 mg/kg/day to about 500 mg/kg/day. In certain embodiments, the effective amount ranges from about 0.01 mg/kg/day to about 400 mg/kg/day. In certain embodiments, the effective amount ranges from about 0.01 mg/kg/day to about 300 mg/kg/day. In certain embodiments, the effective amount ranges from about 0.01 mg/kg/day to about 200 mg/kg/day. In certain embodiments, the effective amount ranges from about 0.01 mg/kg/day to about 100 mg/kg/day. In certain embodiments, the effective amount ranges from about 0.01 mg/kg/day to about 50 mg/kg/day. In certain embodiments, the effective amount ranges from about 0.01 mg/kg/day to about 25 mg/kg/day. In certain embodiments, the effective amount ranges from about 0.01 mg/kg/day to about 20 mg/kg/day. In certain embodiments, the effective amount ranges from about 0.01 mg/kg/day to about 15 mg/kg/day. In certain embodiments, the effective amount ranges from about 0.01 mg/kg/day to about 10 mg/kg/day. In certain embodiments, the effective amount ranges from about 0.01 mg/kg/day to about 5 mg/kg/day. In certain embodiments, the effective amount ranges from about 0.01 mg/kg/day to about 2.5 mg/kg/day. In some embodiments, the effective amount ranges from about 5 mg/kg/day to about 100 mg/kg/day. In some embodiments, the effective amount ranges from about 5 mg/kg/day to about 50 mg/kg/day the effective amount ranges from. In some embodiments, the effective amount ranges from about 5 mg/kg/day to about 30 mg/kg/day. In some embodiments, the effective amount ranges from about 5 mg/kg/day to about 10 mg/kg/day.

In some embodiments, the effective amount of a compound of the disclosure ranges from about 5 mg/kg/day to about 200 mg/kg/day. In some embodiments, the effective amount ranges from about 10 mg/kg/day to about 195 mg/kg/day. In some embodiments, the effective amount ranges from about 15 mg/kg/day to about 190 mg/kg/day. In some embodiments, the effective amount ranges from about 20 mg/kg/day to about 185 mg/kg/day. In some embodiments, the effective amount ranges from about 25 mg/kg/day to about 180 mg/kg/day. In some embodiments, the effective amount ranges from about 30 mg/kg/day to about 175 mg/kg/day. In some embodiments, the effective amount ranges from about 35 mg/kg/day to about 170 mg/kg/day. In some embodiments, the effective amount ranges from about 40 mg/kg/day to about 165 mg/kg/day. In some embodiments, the effective amount ranges from about 45 mg/kg/day to about 160 mg/kg/day. In some embodiments, the effective amount ranges from about 50 mg/kg/day to about 155 mg/kg/day. In some embodiments, the effective amount ranges from about 55 mg/kg/day to about 150 mg/kg/day. In some embodiments, the effective amount ranges from about 60 mg/kg/day to about 145 mg/kg/day. In some embodiments, the effective amount ranges from about 65 mg/kg/day to about 140 mg/kg/day. In some embodiments, the effective amount ranges from about 70 mg/kg/day to about 135 mg/kg/day. In some embodiments, the effective amount ranges from about 75 mg/kg/day to about 130 mg/kg/day. In some embodiments, the effective amount ranges from about 80 mg/kg/day to about 125 mg/kg/day. In some embodiments, the effective amount ranges from about 85 mg/kg/day to about 120 mg/kg/day. In some embodiments, the effective amount ranges from about 90 mg/kg/day to about 115 mg/kg/day. In some embodiments, the effective amount ranges from about 95 mg/kg/day to about 110 mg/kg/day. In some embodiments, the effective amount ranges from about 100 mg/kg/day to about 105 mg/kg/day.

In some embodiments, the effective amount of a compound of the disclosure ranges from about 0.1 mg/kg/day to about 50 mg/kg/day. In some embodiments, the effective amount ranges from about 0.5 mg/kg/day to about 30 mg/kg/day. In some embodiments, the effective amount ranges from about 1 mg/kg/day to about 25 mg/kg/day. In some embodiments, the effective amount ranges from about 2 mg/kg/day to about 20 mg/kg/day. In some embodiments, the effective amount ranges from about 3 mg/kg/day to about 15 mg/kg/day. In some embodiments, the effective amount ranges from about 4 mg/kg/day to about 10 mg/kg/day. In some embodiments, the effective amount ranges from about 0.1 mg/kg/day to about 20 mg/kg/day. In some embodiments, the effective amount ranges from about 0.1 mg/kg/day to about 15 mg/kg/day. In some embodiments, the effective amount ranges from about 0.1 mg/kg/day to about 10 mg/kg/day. In some embodiments, the effective amount ranges from about 0.1 mg/kg/day to about 5 mg/kg/day. In some embodiments, the effective amount ranges from about 0.1 mg/kg/day to about 6.5 mg/kg/day. In some embodiments, the effective amount ranges from about 0.1 mg/kg/day to about 9 mg/kg/day. In some embodiments, the effective amount ranges from about 1 mg/kg/day to about 14 mg/kg/day.

In some embodiments, less than 100 mg/kg/day of a compound of the disclosure is administered. In some embodiments, less than 90 mg/kg/day is administered. In some embodiments, less than 80 mg/kg/day is administered. In some embodiments, less than 70 mg/kg/day is administered. In some embodiments, less than 60 mg/kg/day is administered. In some embodiments, less than 50 mg/kg/day is administered. In some embodiments, less than 40 mg/kg/day is administered. In some embodiments, less than 30 mg/kg/day is administered. In some embodiments, less than 700 mg/kg/day is administered. In some embodiments, less than 20 mg/kg/day is administered. In some embodiments, less than 10 mg/kg/day is administered. In some embodiments, less than 5 mg/kg/day is administered. In some embodiments, less than 2.5 mg/kg/day is administered. In some embodiments, less than 1 mg/kg/day is administered.

In the foregoing embodiments, the amount of a compound of the disclosure administered is greater than 0.01 mg/kg/day.

In some embodiments, the effective amount of a compound of the disclosure is between about 0.1 mg/kg/day and about 50 mg/kg/day. In some embodiments, the effective amount is between about 0.1 mg/kg/day and about 40 mg/kg/day. In some embodiments, the effective amount is between about 0.1 mg/kg/day and about 30 mg/kg/day. In some embodiments, the effective amount is between about 0.1 mg/kg/day and about 20 mg/kg/day. In some embodiments, the effective amount is between about 0.1 mg/kg/day and about 10 mg/kg/day. In some embodiments, the effective amount is between about 0.1 mg/kg/day and about 5 mg/kg/day. In some embodiments, the effective amount is 2.5, 5 or 10 mg/kg/day.

In some embodiments, the effective amount is an amount of a compound of the disclosure sufficient to achieve plasma levels of a compound of the disclosure above 100 ng/ml from 1 to 4 hours after administration. In some embodiments, the effective amount is an amount sufficient to achieve plasma levels of a compound of the disclosure above 500 ng/ml from 1 to 4 hours after administration. In some embodiments, the effective amount is an amount sufficient to achieve plasma levels of a compound of the disclosure above 1000 ng/ml from 1 to 4 hours after administration.

In some embodiments, the effective amount is an amount of a compound of the disclosure sufficient to achieve plasma levels of a compound of the disclosure above 50 ng/ml from 12 to 24 hours after administration. In some embodiments, the effective amount is an amount sufficient to achieve plasma levels of a compound of the disclosure above 75 ng/ml from 12 to 24 hours after administration. In some embodiments, the effective amount is an amount sufficient to achieve plasma levels of a compound of the disclosure above 100 ng/ml from 12 to 24 hours after administration. In some embodiments, the effective amount is an amount sufficient to achieve plasma levels of a compound of the disclosure above 200 ng/ml from 12 to 24 hours after administration.

In some embodiments, the effective amount is an amount of a compound of the disclosure sufficient to achieve a minimum plasma level of a compound of the disclosure above 25 ng/ml after at least four days of administration of an amount of a compound of the disclosure between 1 and 20 mg/kg/day. In some embodiments, the effective amount is an amount of a compound of the disclosure sufficient to achieve a minimum plasma level of a compound of the disclosure above 50 ng/ml after at least four days of administration of an amount of a compound of the disclosure between 1 and 20 mg/kg/day. In some embodiments, the effective amount is an amount of a compound of the disclosure sufficient to achieve a minimum plasma level of a compound of the disclosure above 75 ng/ml after at least four days of administration of an amount of a compound of the disclosure between 1 and 20 mg/kg/day. In some embodiments, the effective amount is an amount of a compound of the disclosure sufficient to achieve a minimum plasma level of a compound of the disclosure above 100 ng/ml after at least four days of administration of an amount of a compound of the disclosure between 1 and 20 mg/kg/day.

In some embodiments, the effective amount is an amount of a compound of the disclosure sufficient to achieve plasma levels of a compound of the disclosure ranging from about 0.5 µg/mL to about 15 µg/mL from 1 to 4 hours after administration. In some embodiments, the effective amount is an amount sufficient to achieve plasma levels of a compound of the disclosure ranging from about 1 µg/mL to about 20 µg/mL from 1 to 4 hours after administration. In some embodiments, the effective amount is an amount sufficient to achieve plasma levels of a compound of the disclosure ranging from about 2 µg/mL to about 25 µg/mL from 1 to 4 hours after administration. In some embodiments, the effective amount is an amount sufficient to achieve plasma levels of a compound of the disclosure ranging from about 3 µg/mL to about 30 µg/mL from 1 to 4 hours after administration. In some embodiments, the effective amount is an amount sufficient to achieve plasma levels of a compound of the disclosure ranging from about 4 µg/mL to about 40 µg/mL from 1 to 4 hours after administration. In some embodiments, the effective amount is an amount sufficient to achieve plasma levels of a compound of the disclosure ranging from about 5 µg/mL to about 50 µg/mL from 1 to 4 hours after administration. In some embodiments, the effective amount is an amount sufficient to achieve plasma levels of a compound of the disclosure ranging from about 5 µg/mL to about 10 µg/mL from 1 to 4 hours after administration. In some embodiments, the effective amount is an amount sufficient to achieve plasma levels of a compound of the disclosure ranging from about 10 µg/mL to about 15 µg/mL from 1 to 4 hours after administration. In some embodiments, the effective amount is an amount sufficient to achieve plasma levels of a compound of the disclosure ranging from about 15 µg/mL to about 20 µg/mL from 1 to 4 hours after administration. In some embodiments, the effective amount ranges is an amount sufficient to achieve plasma levels of a compound of the disclosure ranging from about 20 µg/mL to about 25 µg/mL from 1 to 4 hours after administration. In some embodiments, the effective amount is an amount sufficient to achieve plasma levels of a compound of the disclosure ranging from about 25 µg/mL to about 30 µg/mL from 1 to 4 hours after administration. In some embodiments, the effective amount is an amount sufficient to achieve plasma levels of a compound of the disclosure ranging from about 30 µg/mL to about 40 µg/mL from 1 to 4 hours after administration. In some embodiments, the effective amount is an amount sufficient to achieve plasma levels of a compound of the disclosure ranging from about 40 µg/mL to about 50 µg/mL from 1 to 4 hours after administration. In some embodiments, the effective amount is an amount sufficient to achieve plasma levels of a compound of the disclosure ranging from about 50 µg/mL to about 60 µg/mL from 1 to 4 hours after administration. In some embodiments, the effective amount is an amount sufficient to achieve plasma of a compound of the disclosure levels ranging from about 60 µg/mL to about 70 µg/mL from 1 to 4 hours after administration. In some embodiments, the effective amount is an amount sufficient to achieve plasma levels of a compound of the disclosure ranging from about 70 µg/mL to about 80 µg/mL from 1 to 4 hours after administration. In some embodiments, the effective amount is an amount sufficient to achieve plasma levels of a compound of the disclosure ranging from between about 1 µg/mL to about 50 µg/mL from 1 to 4 hours after administration. In some embodiments, the effective amount is an amount sufficient to achieve plasma levels of a compound of the disclosure ranging from between about 1 µg/mL to about 40 µg/mL from 1 to 4 hours after administration. In some embodiments, the effective amount is an amount sufficient to achieve plasma levels of a compound of the disclosure ranging from between about 1 µg/mL to about 30 µg/mL from 1 to 4 hours after administration. In some embodiments, the effective amount is an amount sufficient to achieve plasma levels of a compound of the disclosure ranging from between about 1 µg/mL to about 20 µg/mL from 1 to 4 hours after administration.

In any of the foregoing embodiments, the compound of the disclosure may be Compound A. In any of the foregoing embodiments, the compound of the disclosure may be Compound A as a pharmaceutically acceptable salt. In any of the foregoing embodiments, the compound of the disclosure may be Compound A as a pharmaceutically acceptable salt, hydrate, solvate or combination of the foregoing.

In certain embodiments, the effective amount is administered in one or more doses according to a course of treatment (where a dose refers to an amount of a compound of the invention administered in a single day). In certain embodiments, the dose is administered q.d. (1 time/administration per day). In certain embodiments, the dose is administered b.i.d. (2 times/administrations per day; for example, one-half of the effective amount in two administrations a day). In certain embodiments, the dose is administered t.i.d. (three times/administrations per day; for example, one-third of the effective amount in two administrations a day). When a dose is divided into multiple administrations per day, the dose may be divided equally or the dose may be divided unequally at each administration. Any given dose may be delivered in a single dosage form or more than one dosage form (for example, a tablet).

In certain embodiments, only one dose of a compound of the disclosure is administered during a course of treatment and no further doses are administered. Therefore, in the methods described herein the methods may comprise the administration of a single dose of an effective amount of a compound of the disclosure during the entire course of treatment. When a single dose is administered during the entire course of treatment, the course of treatment is less than 4 weeks, such as 1 week, 2 weeks or three weeks. When a single dose is administered during the entire course of treatment, the dose may be administered q.d. or the dose may be divided into multiple administrations during the day of administration (such as b.i.d or t.i.d). When a dose is divided into multiple administrations per day, the dose may be divided equally or the dose may be divided unequally at each administration. In certain embodiments, the dose is delivered by IM administration. In certain embodiments, the dose is delivered by IV administration. In certain embodiments, the dose is delivered by parenteral administration. In certain embodiments, the dose is delivered by oral administration. The dose may be delivered in a single dosage form or more than one dosage form (for example, a tablet).

In certain embodiments, more than one dose of a compound of the disclosure is administered during a course of treatment. Therefore, in the methods described herein, the methods may comprise the administration of multiple doses of an effective amount of a compound of the disclosure during the course of treatment. In certain embodiments, the course of treatment may range from 2 days to years. In certain embodiments, the course of treatment may range from 2 days to months. In certain embodiments, the course of treatment may range from 2 days to 4 weeks. In certain embodiments, the course of treatment may range from 2 days to 3 weeks. In certain embodiments, the course of treatment may range from 2 days to 2 weeks. In certain embodiments, the course of treatment may range from 2 days to 1 week. In certain embodiments, an effective amount of a compound of the disclosure may be delivered every day during the course of treatment. In certain embodiments, an effective amount of a compound of the disclosure is not administered every day during the course of treatment (for example, an effective amount may be administered every other day or every third day during the course of treatment). Furthermore, the effective amount need not be the same for every administration during a course of treatment. In one embodiment, a course of treatment may comprise administering at least one dose as a loading dose and at least one dose as a maintenance dose, wherein the loading dose contains a greater amount of a compound of the invention as compared to the maintenance dose (such as, but not limited to, 2 to 10 times higher). In one embodiment, a high dose is administered initially, either for a single administration or more than one administration (a loading dose) followed by administration of a lower dose (a maintenance dose) through the remaining course of treatment. For example, for a course of treatment lasting 10 days, a high dose of 200 mg/kg/day may be administered on the first day of administration, followed by a lower dose of 50 mg/kg/day during the remaining nine days of the course of treatment. As another example, for a course of treatment lasting 10 days, a high dose of 100 mg/kg/day may be administered on the first day of administration, followed by a lower dose of 25 mg/kg/day during the remaining nine days of the course of treatment. As another example, for a course of treatment lasting 25 days, a high dose of 100 mg/kg/day may be administered on the first three days of administration, followed by a lower dose of 25 mg/kg/day during the remaining twenty-two days of the course of treatment. For any given administration, the dose may be administered q.d. or the dose may be divided into multiple administrations during the day of administration (such as b.i.d. or t.i.d.). When a dose is divided into multiple administrations per day, the dose may be divided equally or the dose may be divided unequally at each administration. For example, for the course of treatment lasting 10 days, a high dose of 200 mg/kg/day may be administered on the first day of administration and the dose administered b.i.d (in two separate administration during the day of 100 mg/kg), followed by a lower dose of 50 mg/kg/day during the remaining nine days of the course of treatment and the dose administered b.i.d (in two separate administration during each day of 25.0 mg/kg). For example, for the course of treatment lasting 10 days, a high dose of 100 mg/kg/day may be administered on the first day of administration and the dose administered b.i.d (in two separate administration during the day of 50 mg/kg), followed by a lower dose of 25 mg/kg/day during the remaining nine days of the course of treatment and the dose administered b.i.d (in two separate administration during each day of 12.5 mg/kg). In certain embodiments, the dose is delivered by IM administration. In certain embodiments, the dose is delivered by IV administration. In certain embodiments, the dose is delivered by parenteral administration. In certain embodiments, the dose is delivered by oral administration. The dose may be delivered in a single dosage form or more than one dosage form (for example, a tablet).

In certain embodiments, the dose is administered after a subject has been infected with Zika virus. In certain embodiments, the dose is administered any time after a subject has been infected with Zika virus. In certain embodiments, the dose is administered any time after a subject has been infected with Zika virus and before an active Zika virus infection can be detected (i.e., by laboratory diagnosis or other methods). In certain embodiments, the dose is administered any time during which a subject has an active Zika virus infection (i.e., by laboratory diagnosis or other methods). In certain embodiments, the dose is administered any time after a subject has been infected with Zika virus and at a time when the Zika virus infection is active (i.e., Zika virus may be detected by laboratory diagnosis or other methods). An active Zika virus infection may be detected in any bodily fluid or tissue of the subject, such as, but not limited to, blood, blood plasma or serum, breast milk, amniotic fluid, semen, seminal fluid, vaginal secretions, cerebrospinal fluid, urine, saliva and the like as well as in tissues (including, but not limited to, the brain and both male and female reproductive tissues). In certain embodiments, the bodily fluid is blood. In certain embodiments, the bodily fluid is other than blood. In certain embodiments, the dose is administered 1 day after a subject has been infected with Zika virus. In certain embodiments, the dose is administered 2 days after a subject has been infected with Zika virus. In certain embodiments, the dose is administered 3 days after a subject has been infected with Zika virus. In certain embodiments, the dose is administered 4 days after a subject has been infected with Zika virus. In certain embodiments, the dose is administered 5 days after a subject has been infected with Zika virus. In certain embodiments, the dose is administered 6 days after a subject has been infected with Zika virus. In certain embodiments, the dose is administered 7 days after a subject has been infected with Zika virus. In certain embodiments, the dose is administered 8 days after a subject has been infected with Zika virus. In certain embodiments, the dose is administered 9 days after a subject has been infected with Zika virus. In certain embodiments, the dose is administered 10 days after a subject has been infected with Zika virus. In certain embodiments, the dose is administered 20 days after a subject has been infected with Zika virus. In certain embodiments, the dose is administered more than 30 days after a subject has been infected with Zika virus. Infection with Zika virus may be confirmed with standard laboratory tests and/or diagnosis by a medical professional. In certain embodiments, the dose is delivered by IM administration. In certain embodiments, the dose is delivered by IV administration. In certain embodiments, the dose is delivered by parenteral administration. In certain embodiments, the dose is delivered by oral administration.

In certain embodiments, the dose is administered before a subject is infected with Zika virus (i.e., a prophylactic administration). For example, if a subject is planning to travel to a region where Zika virus infection has been reported or believes he/she may be exposed to Zika virus, the subject may undergo a course of treatment with a compound of the disclosure prior to travel to the region. Furthermore, a subject may be someone that is not initially exposed to Zika virus infection from a non-human vector source (for example a mosquito of the *Aedes* genus). For example, the spouse or partner of someone who has been exposed to Zika virus or who is at risk for exposure to Zika virus (for example, by traveling to an area where Zika virus infection has been reported) may undergo a course of treatment with a compound of the disclosure as well.

In one embodiment, such course of treatment may be one dose of a compound of the disclosure administered during the course of treatment as described herein. As one example, a subject may take the one dose prior to travel to the region, on arrival in the region or while in the region. In certain embodiments, the dose is delivered by IM administration. In certain embodiments, the dose is delivered by IV administration. In certain embodiments, the dose is delivered by parenteral administration. In certain embodiments, the dose is delivered by oral administration.

In one embodiment, such course of treatment may be more than one dose of a compound of the disclosure administered during the course of treatment as described herein. As one example, a subject may optionally take a dose of a compound of the disclosure as per the course of treatment prior to travel to the region (such as, but not limited to, one dose per day 1 to 7 days prior to travel to the region), take a dose of a compound of the disclosure as per the course of treatment while in the region (such as, but not limited to, one dose per day while in the region) and optionally take a dose of a compound of the disclosure as per the course of treatment (such as, but not limited to, one dose per day 1 to 7 days after return from travel to the region). In certain embodiments, the subject takes a dose of a compound of the disclosure prior to travel to the region, on return from the region or both prior to travel to the region and on return from the region. Such a prophylactic use of the compounds of the disclosure are beneficial not only to protect the subject that is administered a compound of the disclosure, but also in protecting those the subject comes into contact with (for example, family members and co-workers). In certain embodiments, the dose is delivered by IM administration. In certain embodiments, the dose is delivered by IV administration. In certain embodiments, the dose is delivered by parenteral administration. In certain embodiments, the dose is delivered by oral administration. The dose may be delivered in a single dosage form or more than one dosage form (for example, a tablet).

In any of the embodiments herein the dose may comprise a compound of the disclosure alone or a compound of the disclosure in a pharmaceutical composition.

The precise dose to be employed in the compositions will also depend on the route of administration, and the seriousness of the infection or disorder, and should be decided according to the judgment of the practitioner and each patient's circumstances. In some embodiments the effective amount for oral, IM, IV or IP administration is about 5 mg/kg/day to about 50 mg/kg/day, about 50 mg/kg/day to about 80 mg/kg/day, about 80 mg/kg/day to about 150 mg/kg/day, about 150 mg/kg/day to about 250 mg/kg/day, about 250 mg/kg/day to about 350 mg/kg/day or about 350 mg/kg/day to about 450 mg/kg/day (or the equivalent doses expressed per square meter of body surface area). In some embodiments the effective amount for oral, IM, IV or IP administration is from about 5 to about 2000 mg, without adjustment for a patient's body weight or body surface area. Other effective doses may be extrapolated from dose-response curves derived from in vitro or animal model test systems. Such animal models and systems are well known in the art.

Those skilled in the art will recognize, or be able to ascertain using no more than routine experimentation, many equivalents to the specific embodiments of the disclosure described herein. Such equivalents are intended to be within the scope of the present disclosure.

The disclosure is further described by the following non-limiting Examples.

EXAMPLES

Example 1. Characterization of Murine Zika Virus Mouse Model

The AG129 mouse model was used in this study and has been used previously in the study of viral polymerase inhibitors of Zika virus. AG129 mice lack both the α/β (type I) and γ (type II) interferon receptors. AG129 mice are susceptible to Zika virus infection and display relevant signs of disease, including conjunctivitis, neurologic involvement and disease, measurable viremia, hindlimb paralysis and mortality as well as hunching, lethargy and excitability at late stages of infection. Death as a result of Zika virus infection generally occurs between 8 and 20 to 30 days after virus challenge depending on the dose of the viral challenge.

Figure 1B:
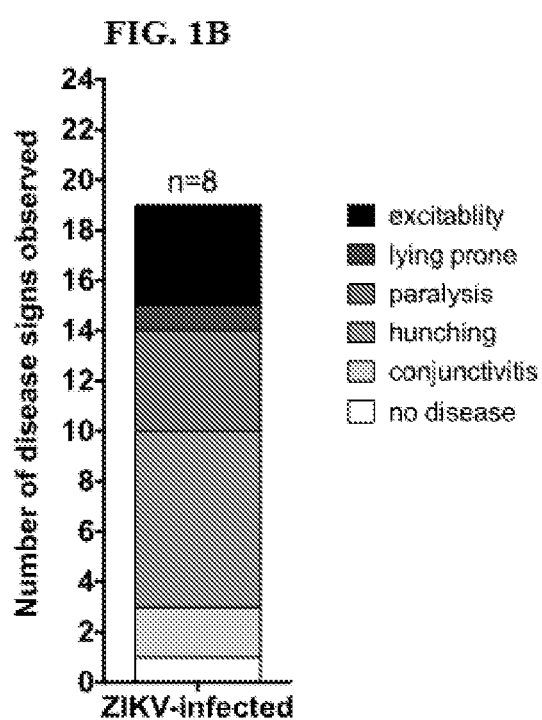
FIG. 1B shows disease signs in AG129 mice exposed to a challenge dose of $10^3$ pfu/mouse Zika virus (Malaysian, strain P 6-740).
Figure 1C:
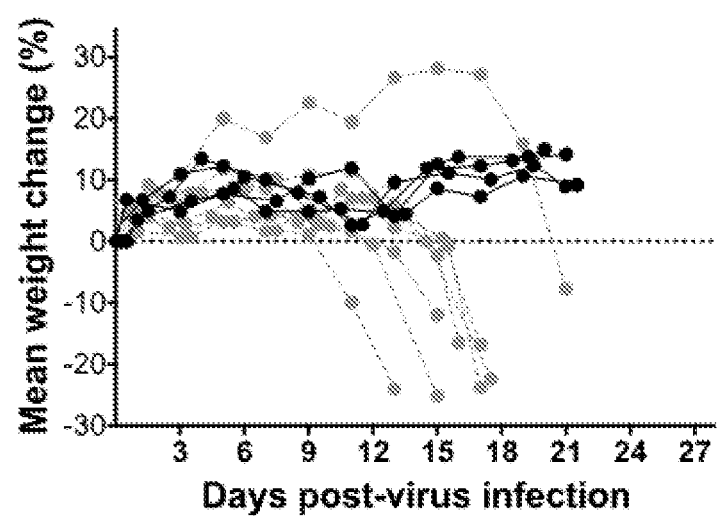
FIG. 1C shows weight change in AG129 mice exposed to a challenge dose of $10^3$ pfu/mouse Zika virus (Malaysian, strain P 6-740).

Malaysian strain (P6-740) of Zika virus was titered in mice (data not shown) and a virus challenge dose of $10^3$ pfu/mouse was identified as a suitable dose to cause 100% mortality in AG129 mice after subcutaneous injection (FIG. 1A). This challenge dose was used in subsequent experiments. Various disease signs including conjunctivitis, limb weakness/paralysis, excitability, hunching and lying prone were observed in infected mice (FIG. 1B). Infected mice typically displayed one or more symptoms, but the disease signs varied from mouse to mouse. Weight change declined rapidly just prior to mortality (FIG. 1C) and coincided with the disease signs described above.

Figure 1D:
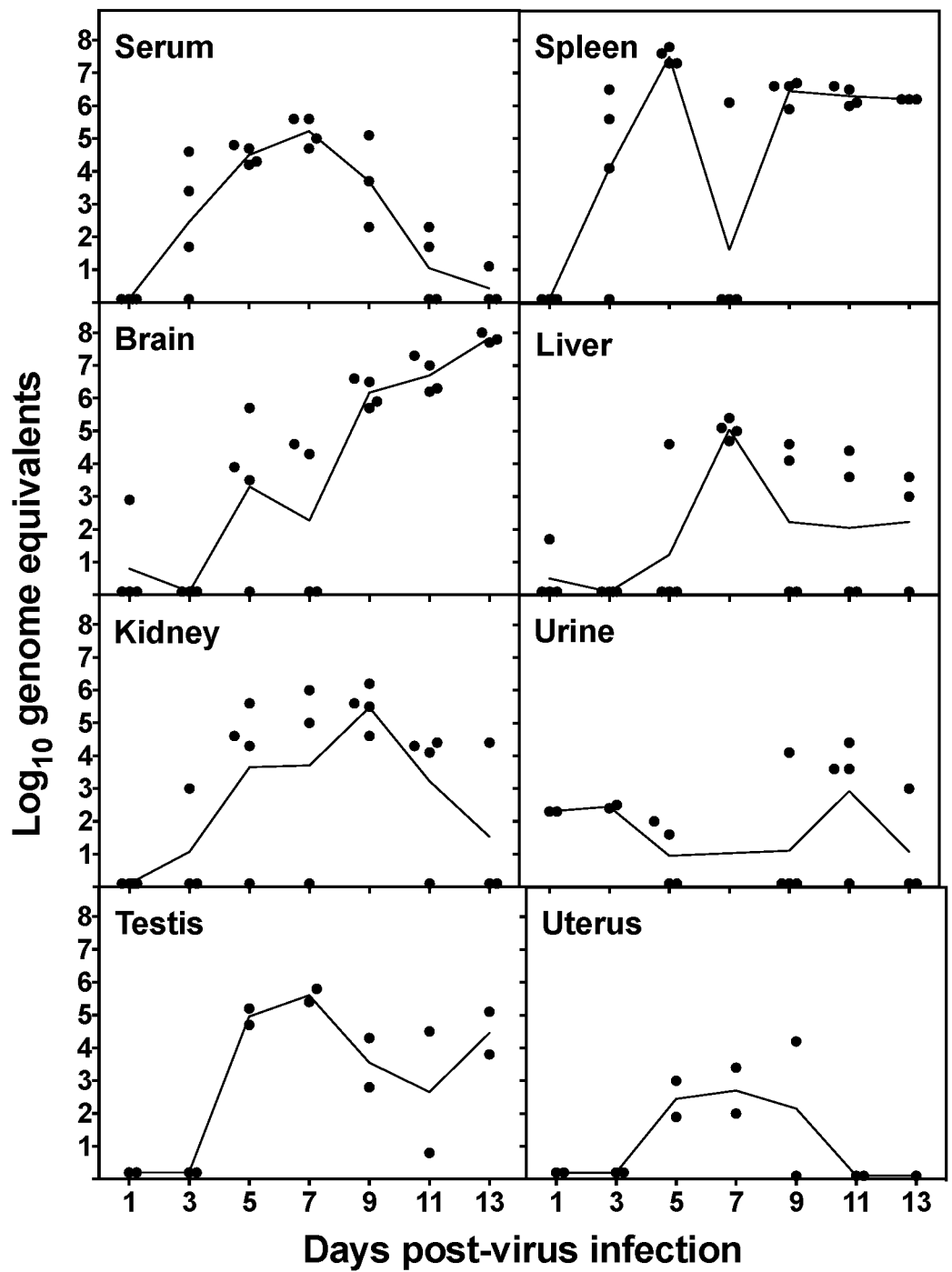
FIG. 1D shows time course of Zika virus RNA accumulation in tissues of AG129 mice exposed to a challenge dose of $10^3$ pfu/mouse Zika virus (Malaysian, strain P 6-740) after infection.

The level of viral RNA accumulation in various tissues was determined by qRT-PCR at various times after infection as described in the Methods section. Viral RNA levels peaked and were cleared from the serum, liver, kidney and uterus, while virus persisted to 13 days post-virus inoculation (dpi) at relatively high titers in spleen, brain and testis (FIG. 1D). High titers were present in serum on 5 and 7 dpi, which was useful as an antemortem parameter for use in antiviral studies. Viral RNA titer in the urine was sporadic, although virus was detected as late as 13 dpi (FIG. 1D). High titers in the brain are consistent with neurological signs of disease that are observed just prior to mortality. Neurological signs included hyperactivity (rapid and uncoordinated running around the cage upon disturbance or randomly), increased respiratory effort, tremor or seizure and hunching.

Example 2. In Vitro Results

The agents used in this experiment were Compound A (the compound of formula I, where A is $NH_2$ and B is H as the HCL salt) and ribavirin. The compounds were administered at a range of concentrations up to 100 µg/ml. Compounds were prepared in MEM just prior to testing. Inhibition of virus replication was determined by microscopic examination of the infected cells for cytopathic effect, increase of neutral red (NR) dye uptake (colorimetric determination), and virus yield reduction. Uninfected cells treated with a compound were assayed as above for cytotoxicity control. The $EC_{50}$, $EC_{90}$ and SI (selectivity index) values were determined in Vero76, Huh7 and RD cells as analyzed by the neutral red uptake dye assay and virus yield reduction assays. The results are presented from 3 or more independent experiments (standard deviations not shown. Three Zika virus strains were used in this in vitro study, Malaysia strain P 6-740, Uganda strain MR-766 and Puerto Rico strain PRVABC-59. Cells were maintained under standard conditions.

Figure 1E:
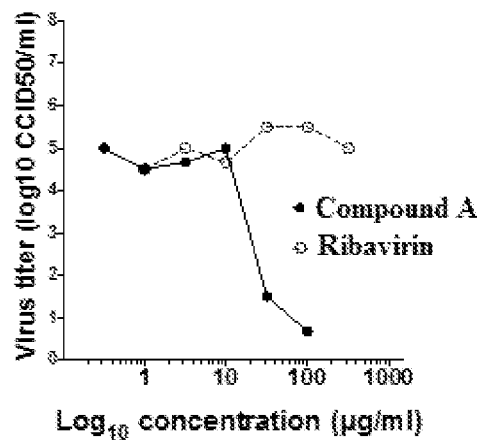
FIG. 1E shows reduction of virus yield by Compound A or Ribavirin in Vero cells.
Figure 1F:
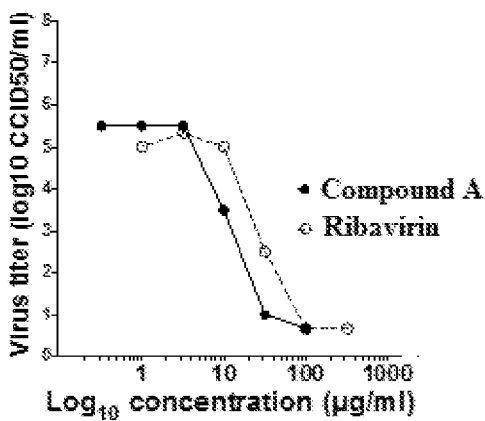
FIG. 1F shows reduction of virus yield by Compound A or Ribavirin in Huh-7 cells.
Figure 1G:
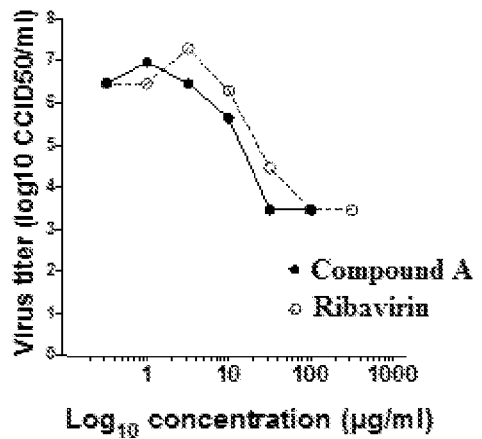
FIG. 1G shows reduction of virus yield by Compound A or Ribavirin in RD cells.

The results are shown in Table 1. Compound A was found to consistently reduce viral CPE induced by Ugandan, Malaysian and Puerto Rican isolates of Zika virus in RD, Huh-7 and Vero76 cell lines with 50% effective concentration ($EC_{50}$) values in the low µM range and favorable selective index (SI) values (Table 1). Efficacy was also similar between the three Zika virus strains that were used, representing African, Asian and currently circulating American strains. Efficacy of Compound A was confirmed by VYR tests. The 90% effective concentration ($EC_{90}$) values, or the concentration required to reduce virus titer by 1 $log_{10}$, were slightly higher but similar to the $EC_{50}$ (Table 1). The VYR curves for Compound A were similar for the three different cell lines tested (FIGS. 1E-1G).

Ribavirin was also active in cell culture with variable results depending on which cell line was used (Table 1). Virus yield reduction assays further demonstrated this cell line-dependent variability. Ribavirin was not active in the VYR studies when the assay was performed in Vero76 cells (FIG. 1E), despite some activity observed in CPE reduction assays. This was unanticipated as Ribavirin has broad-spectrum activity in this cell line against YFV and West Nile virus (WNV). Human cell lines, including Huh-7 and RD, confirmed the antiviral activity of Ribavirin (FIGS. 1F and G, respectively)

TABLE 1

| | | Compound A | | | Ribavirin | | |
|---|---|---|---|---|---|---|---|
| | | CPE | | | | | |
| Zika virus strain | Cell line | red. assay $EC_{50}$ (µg/ml)[a] | VYR assay $EC_{90}$ (µg/ml)[b] | $SI_{90}$[c] | CPE red. assay $EC_{50}$ (µg/ml)[a] | VYR assay $EC_{90}$ (µg/ml)[b] | $SI_{90}$ |
| Puerto Rico PRVABC59 | Vero76 | 3.8 ± 2.5 | 18.2 ± 2.7 | 5.5 | 23.0 ± 16.8 | 2 81 ± 108 | 1.1 |
| | Huh-7 | 4.7 ± 0.6 | 6.7 ± 1.2 | 14.9 | 3.8 ± 1.6 | 10.4 ± 0.8 | 30.7 |
| | RD | 4.7 ± 2.2 | 10.0 ± 2.2 | 10.0 | 10.0 ± 6.0 | 46.3 ± 8.6 | 4.3 |
| Malaysia P 6-740 | Vero76 | 11.5 ± 4.4 | 13.8 ± 3.7 | 7.3 | 143 ± 85.0 | 195 ± 63.6 | 1.6 |
| | Huh-7 | 5.5 ± 0.1 | 4.9 ± 0.9 | 20.5 | 7.2 ± 2.8 | 13.1 ± 0.5 | 24.5 |
| Uganda MR 766 | Vero76 | 11.7 ± 4.7 | 8.7 | 11.6 | 85 ± 77.9 | 198 ± 172.5 | 1.6 |
| | Huh-7 | 5.7 ± 0.9 | 6.4 | 15.7 | 8.9 ± 7.9 | 9.52 ± 2.1 | 33.6 |
| | RD | 4.4 ± 1.3 | 5.4 ± 1.1 | 18.5 | 9.3 ± 5.2 | 13.2 ± 1.7 | 23.1 |

[a]The 50% effective concentration, or the concentration necessary to reduce viral cytopathic effect by 50%, was determined using a CPE reduction assay.
[b]90% effective concentration, or the concentration necessary to reduce virus from cells harvested on 5 dpi by 1 $log_{10}$ 50% cell culture infectious dose (CCID50%).
[c]90% selective index is obtained by dividing the cytotoxic concentration (not shown), obtained by treating cell controls in the absence of virus with serial dilutions of compound and recording dose at which 50% inhibition of cells occurs, by the $EC_{90}$.

Example 3. Efficacy of Compound A and Ribavirin in the Murine Zika Virus Model

The agents used in this experiment were compound A (the compound of formula I, where A is $NH_2$ and B is H as the HCL salt) and ribavirin. Compound A was administered IM at 150 mg/kg/day and 300 mg/kg/day, each in a volume of 0.05 ml saline and ribavirin was administered IP at 75 mg/kg/day and 50 mg/kg/day, each in a volume of 0.1 ml saline. IM or IP administration of the daily dose was accomplished in two IM/IP injections of one-half the daily dose each. Mice were administered the first dose of Compound A and ribavirin 4 hours prior to infection with Zika virus and continued the treatment for 8 days post-infection.

In this experiment, Zika virus (Malaysia, strain P 6-740) was administered at a challenge dose of 100 $CCID_{50}$ ($10^3$ pfu) per mouse via subcutaneous injection in a 0.1 ml volume. The treatment groups are shown in Table 2 below.

TABLE 2

| n | Group | Compound | Dose | Schedule | Virus |
|---|---|---|---|---|---|
| 8 | 1 | Comp A | 300 mg/kg/d | 0.05 ml, IM, bid × 8, beg - 4 h | Zika virus Malaysia |
| 8 | 3 | Comp A | 150 mg/kg/d | 0.05 ml, IM, bid × 8, beg - 4 h | Zika virus Malaysia |
| 8 | 5 | Ribavirin | 75 mg/kg/d | 0.1 ml, IP bid × 8, beg - 4 h | Zika virus Malaysia |
| 8 | 7 | Ribavirin | 50 mg/kg/d | 0.1 ml, IP bid × 8, beg - 4 h | Zika virus Malaysia |
| 8 | 9 | Placebo | N/A | 0.1 ml, bid × 8, beg - 4 h | Zika virus Malaysia |
| 3 | 2 | Comp A | 300 mg/kg/d | 0.05 ml, IM, bid × 8, beg - 4 h | Sham |
| 3 | 4 | Ribavirin | 75 mg/kg/d | 0.1 ml, IP bid × 8, beg - 4 h | Sham |
| 3 | 6 | Placebo | N/A | 0.1 ml, bid × 8, beg - 4 h | Sham |
| 3 | 8 | Normal Controls | NA | NA | NA |

Mice were monitored for survival 28 days post-virus challenge. Weight change for individual mice were taken on day 0 and every other day through the end of the experiments. Mice were observed daily for signs of disease including conjunctivitis, hunching, and limb weakness or paralysis.

Figure 2:
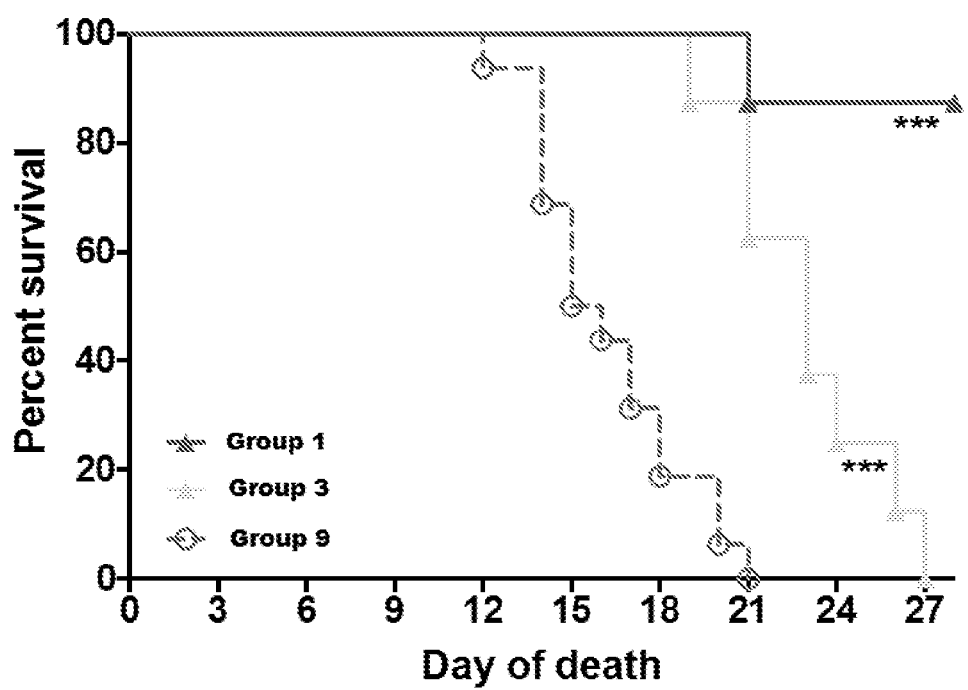
FIG. 2 shows the effect of 150 mg/kg/day and 300 mg/kg/day Compound A administered 4 hours prior to infection with Zika virus on survival in AG129 mice as compared to placebo (***$P<0.001$ as compared with placebo control.

FIG. 2 shows the percent survival for AG129 mice administered 150 mg/kg/day (group 3) and 300 mg/kg/day (group 1) Compound A as compared to placebo (group 9). As shown in FIG. 2, no mice in the placebo group survived past day 21 post-infection, while 7/8 mice treated with Compound A at 300 mg/kg/day survived to day 28 post-infection. The increase in survival was statistically significant (p<0.0001). While the mice treated with 150 mg/kg/day Compound A all died by day 27 post-infection, Compound A delayed the mortality curve of infected mice in a statistically significant manner (p<0.001). Furthermore, no morbidity was observed in the surviving mice in group 1 28 days post-infection. No morbidity or mortality of mic in the sham treated groups (groups 2 and 6) was noted at day 28 post-infection.

Figure 3A:
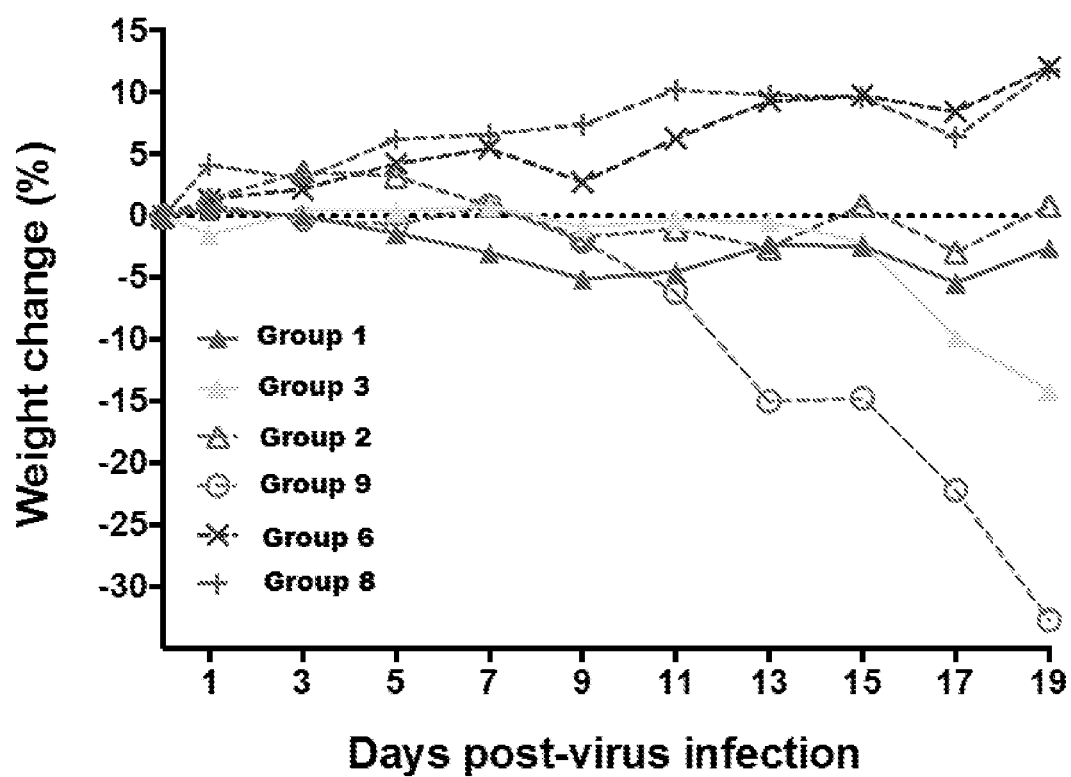
FIG. 3A shows the effect of 150 mg/kg/day and 300 mg/kg/day Compound A administered 4 hours prior to infection with Zika virus on percent weight change in AG129 mice as compared to placebo, normal controls and sham-treated mice.
Figure 3B:
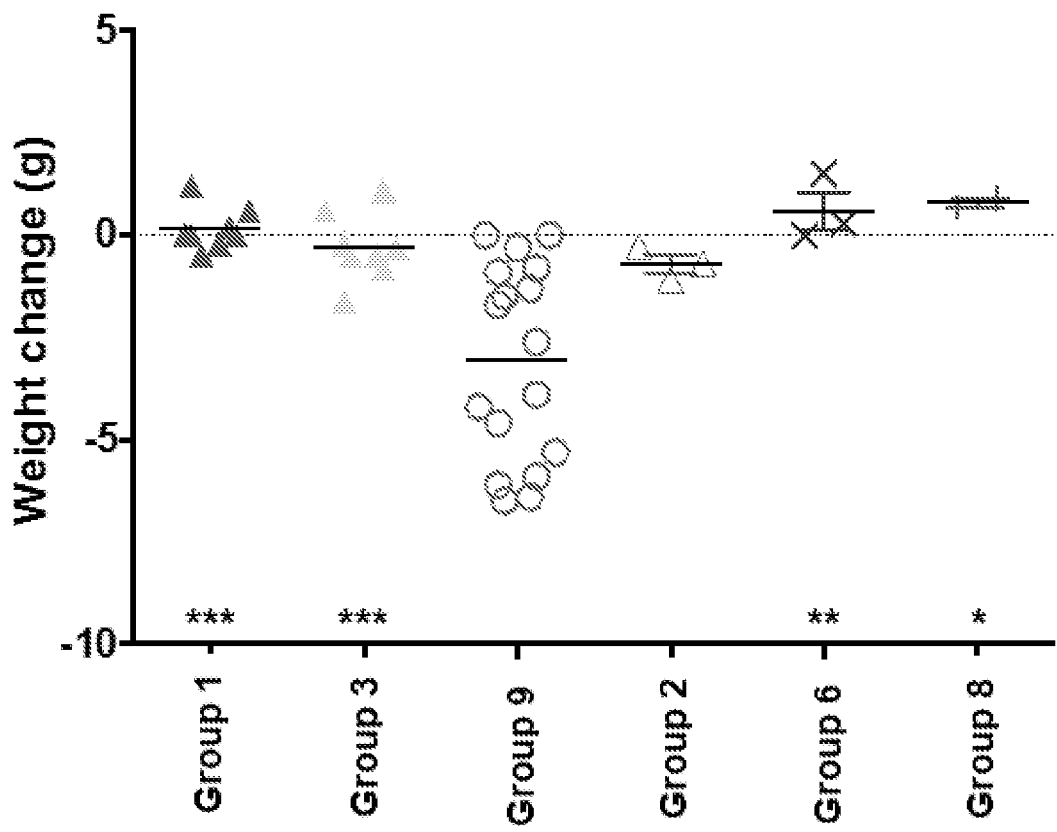
FIG. 3B shows the effect of 150 mg/kg/day and 300 mg/kg/day Compound A administered 4 hours prior to infection with Zika virus on weight change in grams between days 7 and 13 post-infection in AG129 mice as compared to placebo, normal controls and sham-treated mice (*$P<0.001$, $P<0.01$, *$P<0.1$ as compared with placebo control).

FIG. 3A shows the percent weight change in AG129 mice administered 150 mg/kg/day (group 3) and 300 mg/kg/day (group 1) Compound A as compared to placebo (group 9), Compound A 300 mg/kg/day sham group (group 2), sham placebo (group 6) and normal controls (group 8). As shown in FIG. 3A, treatment with 300 mg/kg/day Compound A (both with Zika virus infection, group 1, and sham controls, group 2) resulted in a weight change similar to that seen in normal controls (group 8) and sham mice (group 6). Mice administered 150 mg/kg/day Compound A (group 3) showed modest weight reduction starting around day 15 post-infection. Placebo mice (group 9) showed drastic weight loss starting around day 11 post-infection. FIG. 3B shows the weight change in grams between days 7 and 13 post-infection (a point at which minimal mortality was observed for any group). Treatment with 300 mg/kg/day Compound A (both with Zika virus infection, group 1, and sham controls, group 2) and 150 mg/kg/day Compound A (group 1) resulted in a weight change similar to that seen in normal controls (group 8) and sham mice (group 6). Placebo mice (group 9) showed increased weight loss, mirroring the results shown in FIG. 3A.

Figure 4:
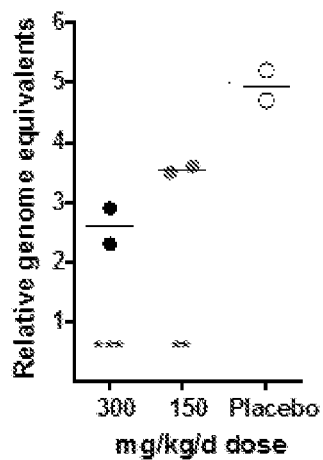
FIG. 4 shows the effect of 150 mg/kg/day and 300 mg/kg/day Compound A administered 4 hours prior to infection with Zika virus on viral load in AG129 mice as compared to placebo (*$P<0.001$, $P<0.01$, as compared with placebo control).

FIG. 4 shows the amount of Zika virus present in AG129 mice. Relative virus levels were determined as described in the Methods section. Treatment with Compound A at 300 mg/kg/day or 150 mg/kg/day (groups 1 and 3, respectively) decreased viral levels in a statistically significant manner as compared to placebo (group 9).

Figure 5:
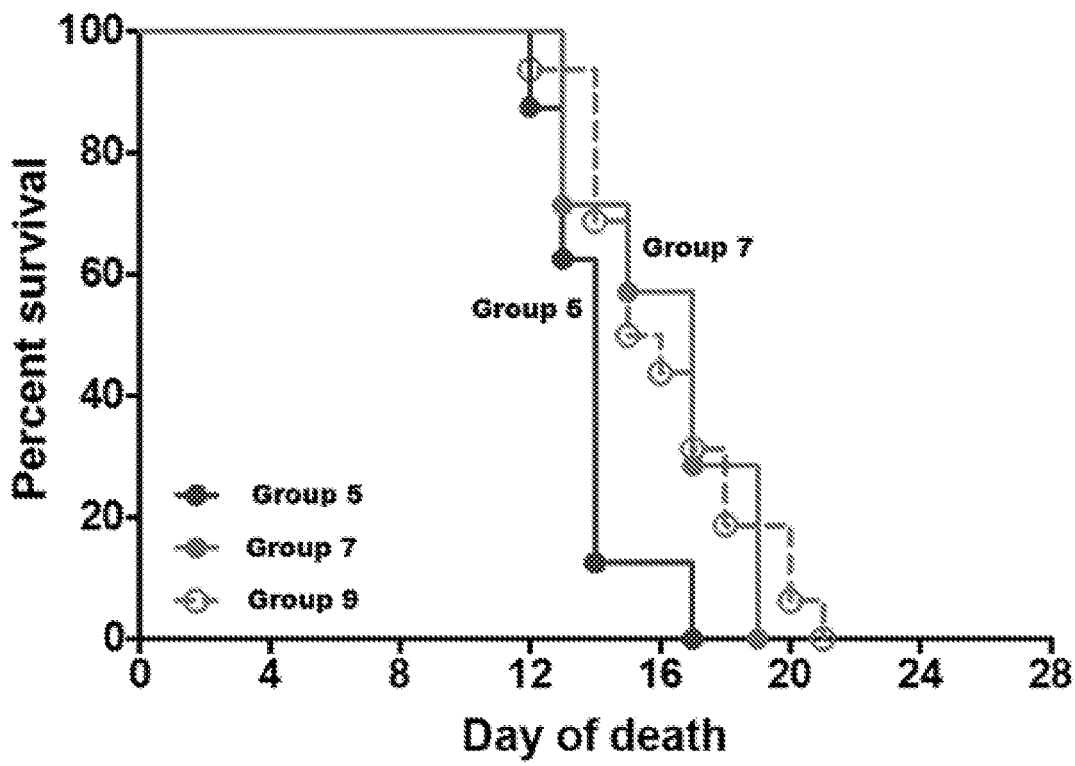
FIG. 5 shows the effect of 50 mg/kg/day and 75 mg/kg/day ribavirin administered 4 hours prior to infection with Zika virus on survival in AG129 mice as compared to placebo.

FIG. 5 shows the percent survival for AG129 mice administered 50 mg/kg/day (group 7) and 75 mg/kg/day (group 5) ribavirin as compared to placebo (group 9). As shown in FIG. 5, treatment with ribavirin at either dose did not increase the survival of AG129 mice as compared to placebo, with no mice in groups 5 and 7 surviving past day 20 post-infection.

Figure 6:
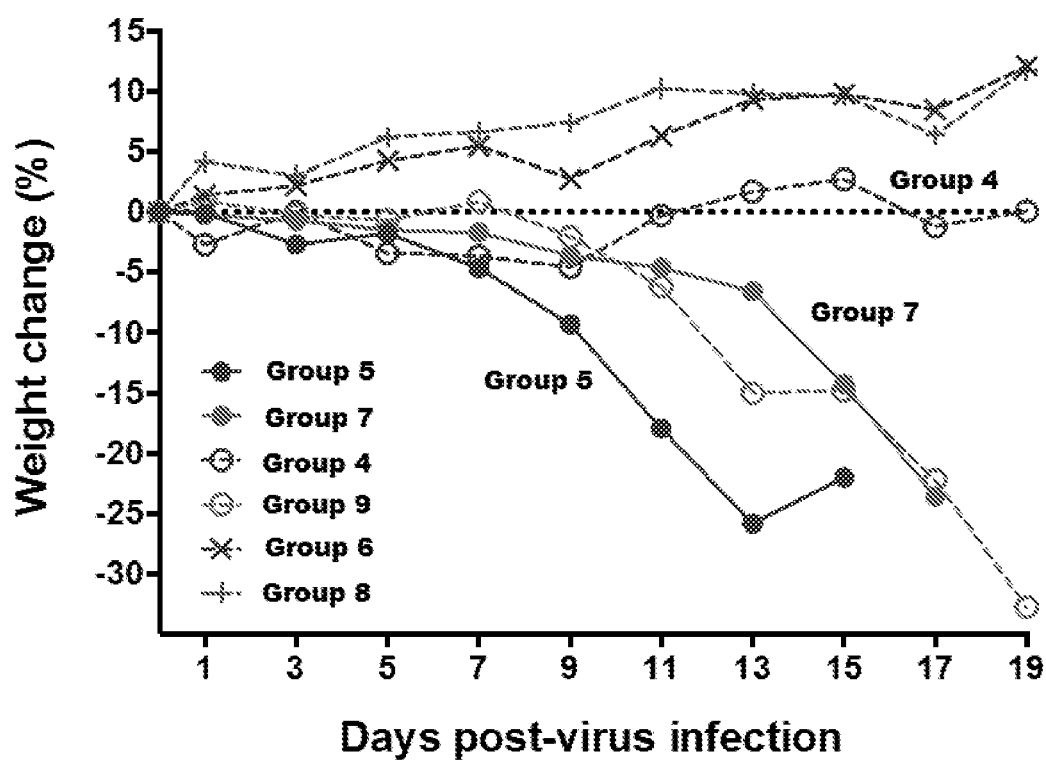
FIG. 6 shows the effect of 50 mg/kg/day and 75 mg/kg/day ribavirin administered 4 hours prior to infection with Zika virus on percent weight change in AG129 mice as compared to placebo, normal controls and sham-treated mice.
Figure 7:
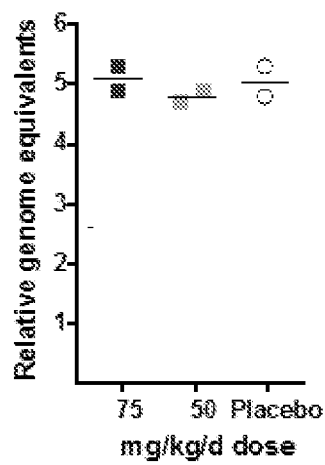
FIG. 7 shows the effect of 50 mg/kg/day and 75 mg/kg/day ribavirin administered 4 hours prior to infection with Zika virus on viral load in AG129 mice as compared to placebo.

FIG. 6 shows the percentage weight change AG129 mice administered 50 mg/kg/day (group 7) and 75 mg/kg/day (group 5) ribavirin as compared to placebo (group 9), ribavirin 75 mg/kg/day sham group (group 4), sham placebo (group 6) and normal controls (group 8). Ribavirin at both 75 mg/kg/day and 50 mg/kg/day showed no significant improvement in percentage weight change as compared to placebo. The mice in group 6 (ribavirin 75 mg/kg/day sham) showed no significant weight change at day 19 post-infection. Consistent with the results in FIGS. 5 and 6, Treatment with ribavirin at 50 mg/kg/day (group 7) and 75 mg/kg/day (group 5) failed to decrease relative virus levels in AG129 mice as compared to placebo (see FIG. 7).

These results show that Compound A is effective in the treatment of Zika virus infection.

Example 4. Efficacy of Compound a in the Murine Zika Virus Model after Re-challenge In this example, the surviving mice from the study described in Example 3 were subject to re-challenge on day 28 post-infection. On day 28, the only surviving mice in a treatment group were in group 1 (7/8 mice), the normal controls (group 8, 8/8 mice) and the virus sham treated groups (group 2, 8/8 mice and group 6, 8/8/mice). All surviving mice (with the exception of normal controls) were administered a challenge of Zika virus identical to the initial challenge.

Zika virus (Malaysia, strain P 6-740) was administered at a challenge dose of 100 $CCID_{50}$ ($10^3$ pfu) per mouse via subcutaneous injection in a 0.1 ml volume to the mice in groups 1, 2 and 6. No animals in Groups 1, 2 and 6 were administered additional doses of Compound A on day 28 prior to or after re-challenge. In this experiment, the sham infected mice of groups 2 and 6 served as the control groups to analyze the effects of treatment of Compound A on immune system activation (note that mice in group 2 received the same 300 mg/kg/day dose of Compound A as the mice in group 1 on day 0). The survival of the mice was monitored through day 60 post-initial infection. The treatment groups are those shown in Table 2 (Example 3).

Figure 8A:
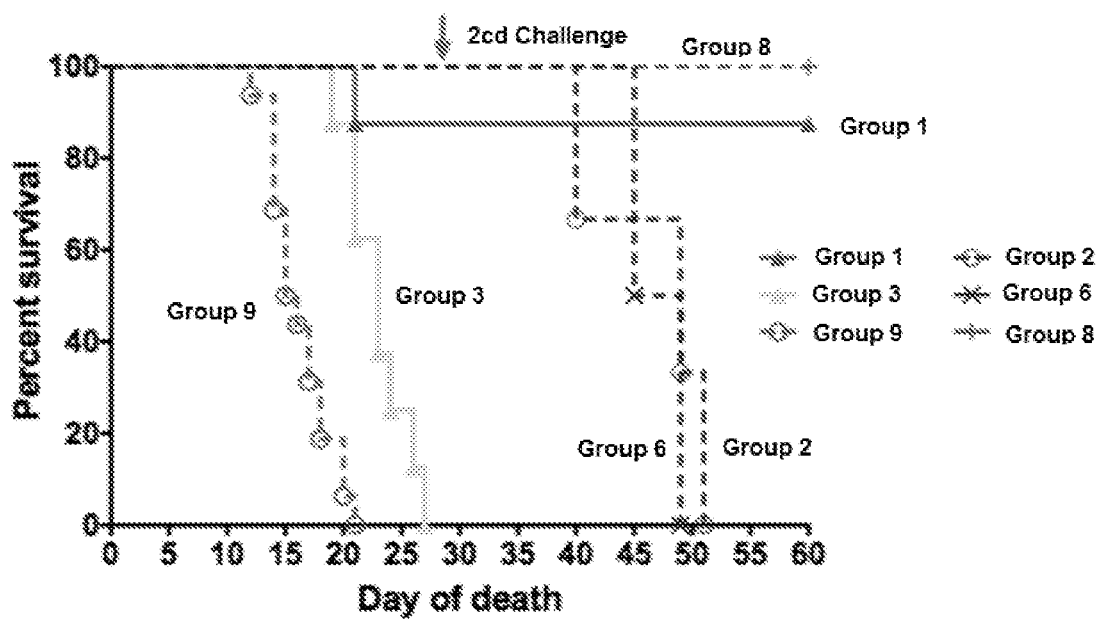
FIG. 8A shows the effect of 300 mg/kg/day Compound A on survival in AG129 mice after a second challenge with Zika virus administered 28 days after initial Zika virus challenge as compared to placebo, normal controls and sham-treated mice.
Figure 8B:
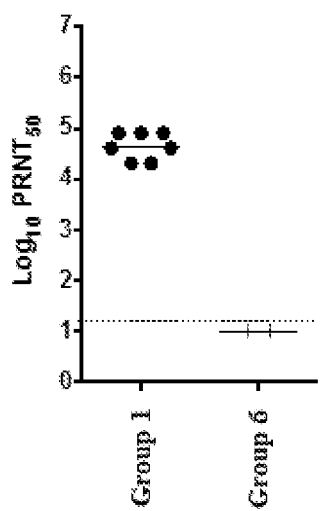
FIG. 8B shows the titer of Zika virus-neutralizing antibody in serum of mice from group 1 (compound A treated 300 mg/kg b.i.d., Zika virus infected) and group 6 (placebo, sham infected) prior to re-challenge with Zika virus on day 28.

FIG. 8A shows the results. No additional mortality was observed in the mice in group 1 after the second challenge with Zika virus, with all 7 of the mice re-challenged with Zika virus surviving at day 60. In contrast, in the sham treated groups (groups 2 and 6, which were challenged with Zika virus for the first time on day 28), no survival was observed past day 51 (or 23 days post secondary challenge for these groups), which is consistent with the earlier results showing 100% mortality of Zika infected AG129 mice absent treatment with Compound A. All normal control mice survived at day 60. Antibody titers for neutralizing antibody to Zika virus were determined in serum samples taken just prior to re-challenge with Zika virus on day 28 from Compound A-treated mice that survived initial Zika virus challenge (group 1) and from mice that were subject to sham infection (group 6). The results are shown in FIG. 8B. The mice of group 1 showed high titers of Zika virus-neutralizing antibody (4-5 $\log_{10}$ $PRNT_{50}$) in serum. Mice that were initially uninfected with Zika virus (group 6) did not show detectable levels of Zika virus-neutralizing antibody in serum prior to infection in the re-challenge study. Collectively, these results show that treatment with Compound A does not impair the generation of de novo antiviral immune responses or inhibit antibody generation to Zika virus.

These results show that Compound A is effective in the treatment of Zika virus infection and is effective in the event of re-infection with Zika virus.

Example 5. Therapeutic Efficacy of Compound A in the Murine Zika Virus Model

The agent used in this experiment was compound A (the compound of formula I, where A is $NH_2$ and B is H as the HCL salt). Compound A was administered IM at 300 mg/kg/day in a volume of 0.05 ml saline. IM administration of the daily dose was accomplished in two IM injections of one-half the daily dose each. Mice were administered the first dose of Compound A 1, 3, 5 or 7 days post-infection (dpi) with Zika virus and continued the treatment for 8 days after the initial dose (n=8 for each condition except for placebo, where n=10 and normal controls, where n=4). Zika virus (Malaysia, strain P 6-740) was administered at a challenge dose of 100 $CCID_{50}$ ($10^3$ pfu) per mouse via subcutaneous injection in a 0.1 ml volume. The results are shown in FIGS. 9-11.

Figure 9:
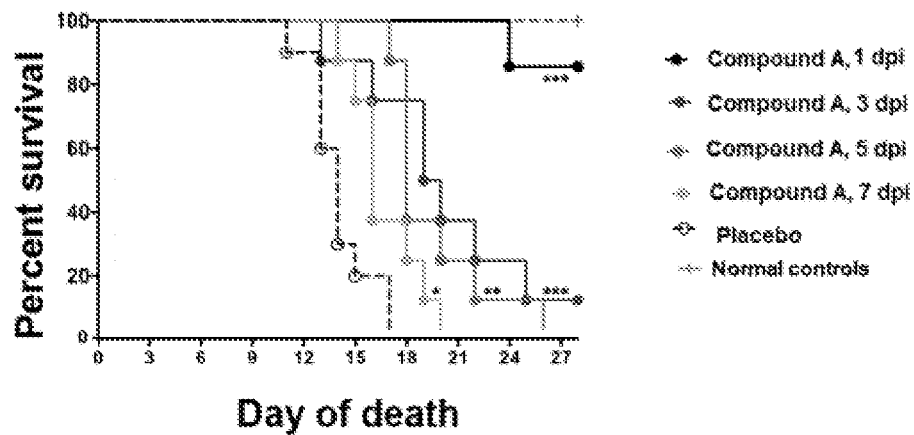
FIG. 9 shows the effect of 300 mg/kg/day Compound A administered at 1, 3, 5 and 7 days post-infection on survival in AG129 mice as compared to placebo (*$P<0.001$, $P<0.01$, *$P<0.1$ as compared with placebo control).

FIG. 9 shows the survival of mice treated with 300 mg/kg/day Compound A at 1, 3, 5 and 7 dpi as compared to placebo. Consistent with previous results, no mice in the placebo group survived past day 18 post-infection. Administration of Compound A 1 dpi resulted in a statistically significant improvements in survival as compared to the placebo group (p<0.001). While the mice treated with 300 mg/kg/day Compound A at 3 and 5 dpi showed increased mortality as compared to Compound A administered 1 dpi, Compound A delayed the mortality curve of infected mice and increased survival in a statistically significant manner (p≤0.001 for * and p≤0.01 for ).

Figure 10A:
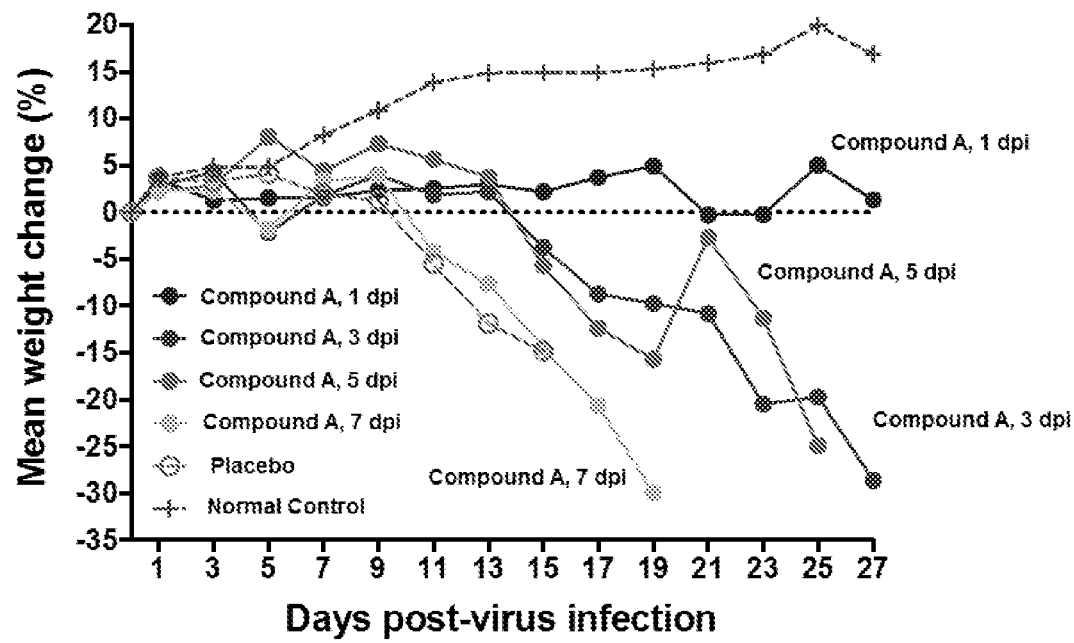
FIG. 10A shows the effect of 300 mg/kg/day Compound A administered at 1, 3, 5 and 7 days post-infection on percent weight change in AG129 mice as compared to placebo.
Figure 10B:
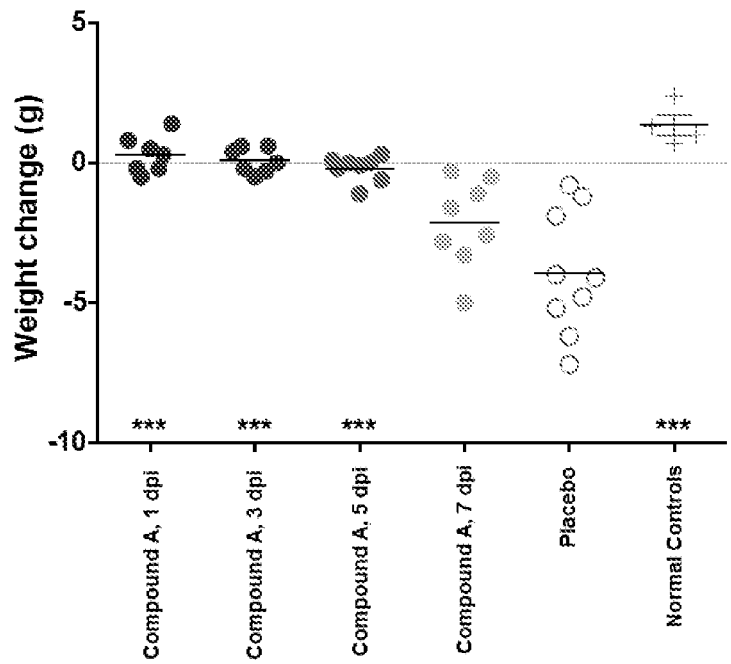
FIG. 10B shows the effect of 300 mg/kg/day Compound A administered at 1, 3, 5 and 7 days post-infection on weight change in grams between days 7 and 13 post-infection in AG129 mice as compared to placebo (***P<0.001 as compared with placebo control).
Figure 10C:
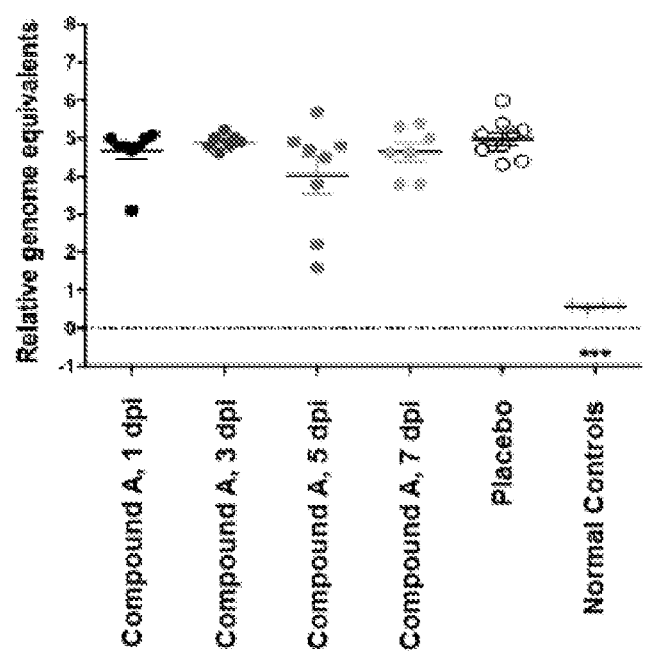
FIG. 10C shows the effect of 300 mg/kg/day Compound A administered at 1, 3, 5 and 7 days post-infection on viral load in AG129 mice as compared to placebo (***P<0.001 compared with placebo control).

FIG. 10A shows the percent weight change in AG129 mice administered 300 mg/kg/day 1, 3, 5 and 7 dpi as compared to placebo and normal controls. Treatment with 300 mg/kg/day Compound A at 1 dpi showed essentially no weight change through 27 dpi, while normal controls showed a 15% increase in weight gain at 27 dpi. For treatment with Compound A 3, 5 and 7 dpi, the percent weight loss increased with the delay in administration of Compound A, with treatment at 3 and 5 dpi showing statistically significant decreases in percentage weight loss. FIG. 10B shows the weight change in grams between days 7 and 13 post-infection (a point at which minimal mortality was observed for any group). Treatment with 300 mg/kg/day Compound A at 1, 3 and 5 dpi resulted in a statistically significant decrease in weight loss as compared to placebo treated mice (p<0.001) consistent with the results in FIG. 10A. FIG. 10C shows viremia on day 5 post-infection. Viral RNA levels in serum on day 5 post-infection (relative to virus administration in each group) were not significantly decreased in any treatment group.

Figure 11:
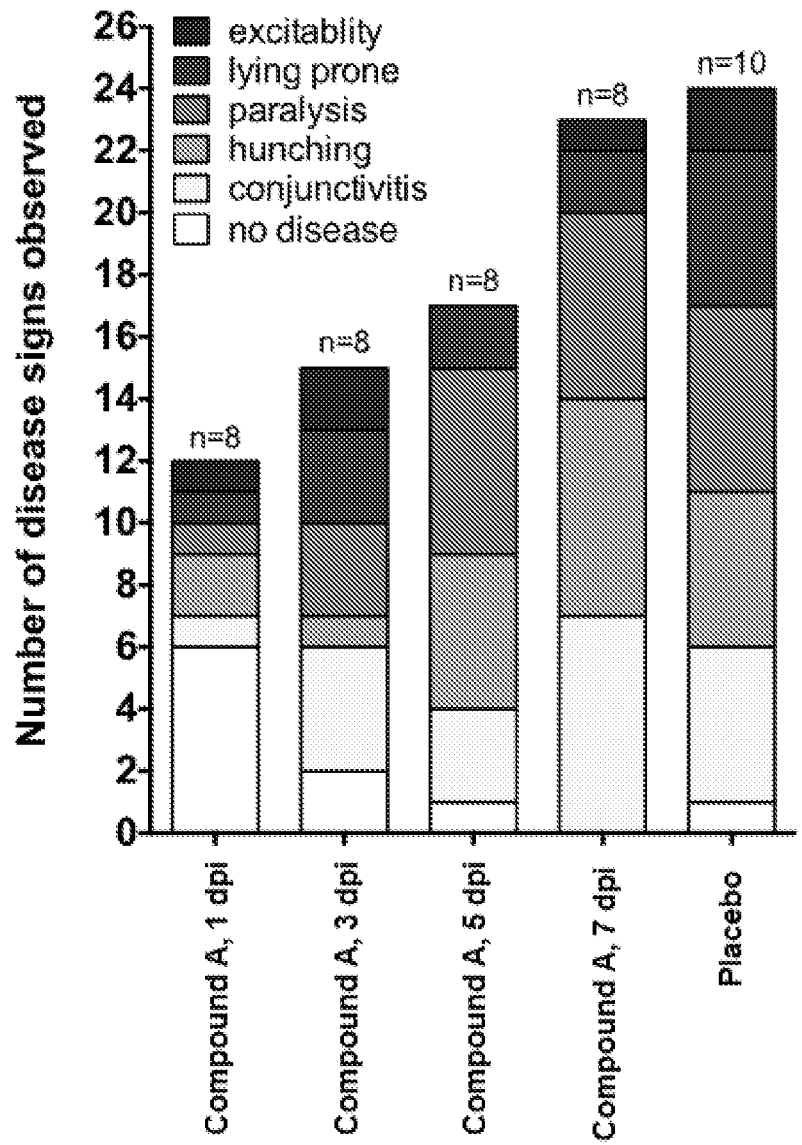
FIG. 11 shows the effect of 300 mg/kg/day Compound A administered at 1, 3, 5 and 7 days post-infection on the appearance of disease signs in AG129 mice.

FIG. 11 shows the assessment of disease signs (excitability, lying prone, paralysis, hunching, conjunctivitis or no sign) by treatment. Disease signs were assessed daily for each mouse and the date the disease sign was first noted was recorded. The graph represents the number of mice observed with each disease sign. Only about 50% of the mice in each group displayed each disease sign. For compound A administered 1 dpi, 6 mice showed no disease, while the remaining 2 mice showed 6 disease signs as indicated. As the time of administration of Compound A post-infection increased, the number of mice displaying no disease signs decreased (2 mice at 3 dpi, 1 mouse at 5 dpi and 0 mice at 7 dpi) and the total number of disease signs increased (13 disease signs at 3 dpi, 16 disease signs at 5 dpi and 23 disease signs at 7 dpi).

These results show that Compound A is effective when administered up to 5 days post-infection with Zika virus and may be used therapeutically for the treatment of Zika virus infection.

Figure 14A:
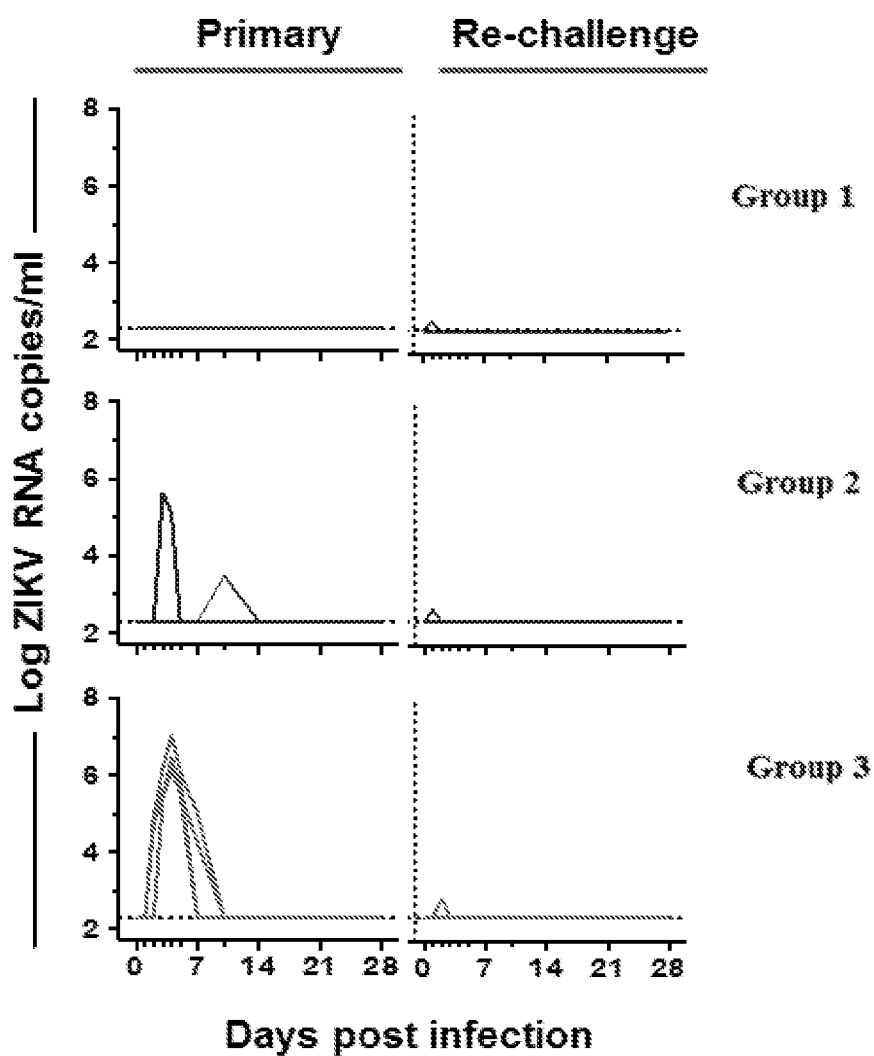
FIG. 14A shows the presence of Zika virus RNA in plasma of animals after primary challenge with Zika virus strain PRVABC-59 and subsequent heterologous challenge with Zika virus strain KF993678.
Figure 14B:
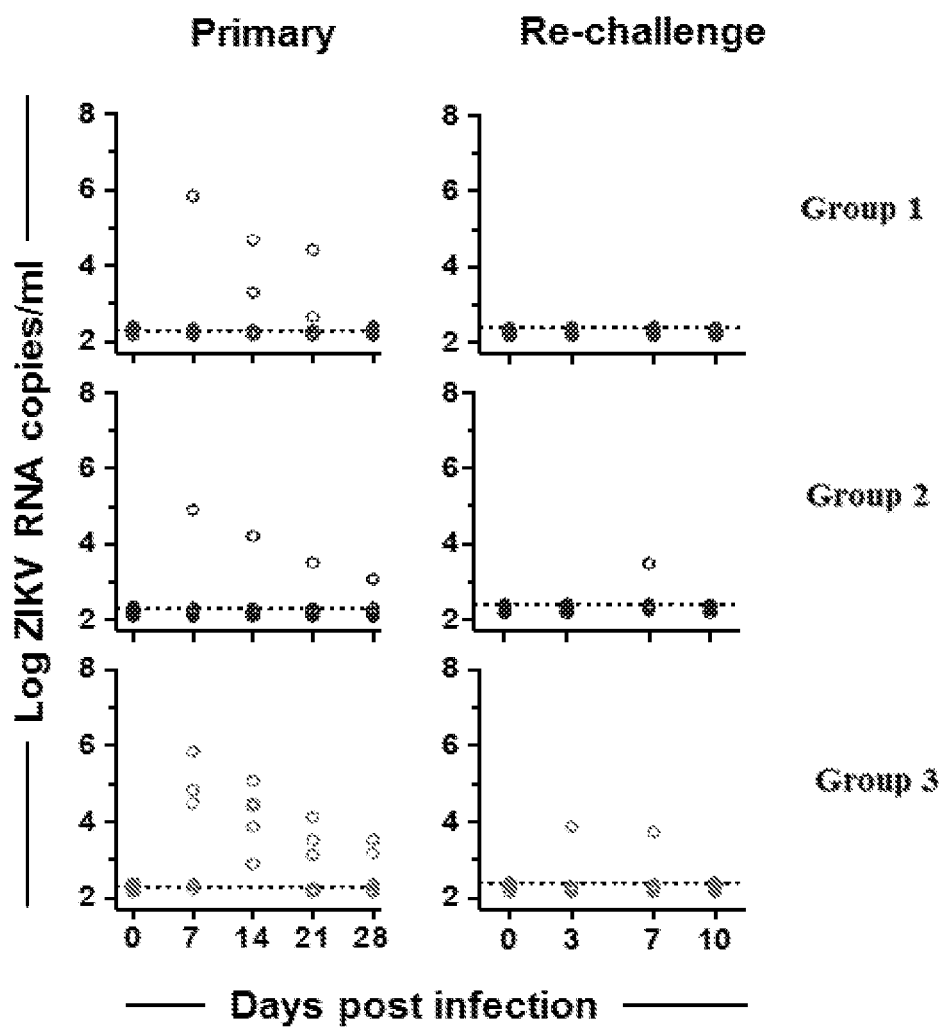
FIG. 14B shows the presence of Zika virus RNA in CSF of animals after primary challenge with Zika virus strain PRVABC-59 and subsequent heterologous challenge with Zika virus strain KF993678.
Figure 14C:
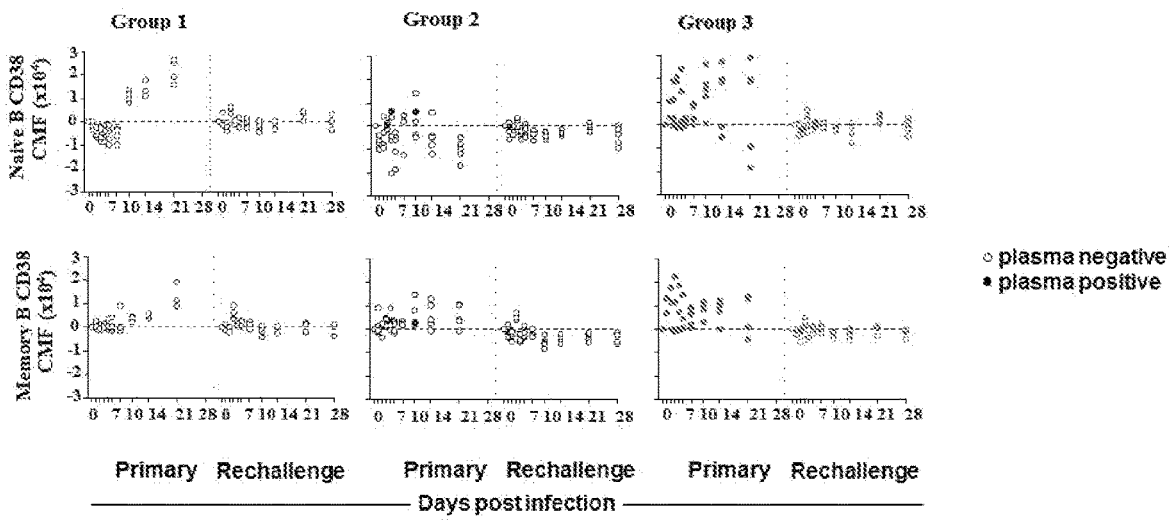
FIG. 14C shows B cell activation over time post-infection after primary challenge with Zika strain PRVABC-59 and heterologous challenge with Zika strain KF993678.
Figure 14D:
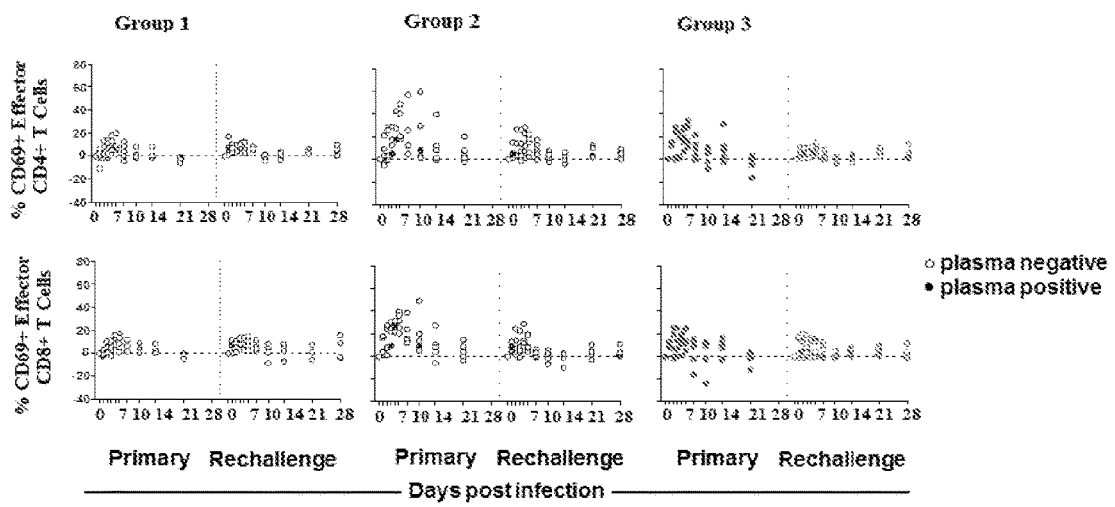
FIG. 14D shows memory T cell activation over time post-infection after primary challenge with Zika strain PRVABC-59 and heterologous challenge with Zika strain KF993678.

Example 6. Therapeutic Efficacy of Compound a in a Non-Human Primate Zika Virus Model The agent used in this experiment was compound A (the compound of formula I, where A is $NH_2$ and B is H as the HCL salt). The non-human primate (NHP) animals used in this example were captive-bred Indian rhesus macaques. Rhesus macaques have been reported to be susceptible to infection by lineages of Zika virus that are currently circulating around the world (Osuna, et al., Nat Med, PMID 27694931, October 2016, which is hereby incorporated by reference for such teaching). In the Rhesus macaque model, peak viremia is observed 2-3 days after viral administration, with male animals showing slightly greater peak viremia than female animals. Body temperature correlates generally with viremic load in this model system. After infection, Zika virus RNA can be detected in any bodily fluid or tissue of the subject, such as, but not limited to, blood, blood plasma or serum, breast milk, amniotic fluid, semen, seminal fluid, vaginal secretions, cerebrospinal fluid, urine, saliva and the like as well as in tissues (including, but not limited to, the brain, neurological tissue, and both male and female reproductive tissues). In this model, Zika virus infection is not fatal with administration of the dose of Zika virus strains in this example. In addition, in rhesus macaques initial Zika virus infection has been shown to elicit protective immunity on re-infection.

Animals were pre-screened to be seronegative for simian retrovirus, Herpes B, and filoviruses. Fifteen animals (n=15) were used in this example and divided into 3 groups (see Table 3). Two groups animals (Groups 1 and 2; n=5 for each) were treated with compound A as described in Table 3. The control group (Group 3; n=5) received formulation vehicle only. All animals in Groups 1 to 3 received the dose of Zika virus described. A Puerto Rican isolate of Zika virus (PRV-ABC-59) was used in this example during initial viral challenge and administered subcutaneously at a dose of $10^5$ PFU. For heterologous challenge after initial viral infection, a Thai isolate of Zika virus (KF993678) was used (administered day 70 post-infection with respect to initial Zika virus challenge). For the initial viral infection, animals were monitored throughout the course of the study by sampling whole blood as well as urine, saliva and cerebrospinal fluid (CSF) to monitor for the presence of Zika virus. Samples were taken pre-dose and on days 0, 1, 2, 3, 4, 5, 7, 10, 14, 21 and 28 for blood, urine and saliva and on days 7, 14, 21 and 28 for CSF (via lumbar puncture). Zika virus RNA levels in the plasma, urine, saliva and CSF were measured.

For Group 1, formulated Compound A was administered by IM on day 0 at 200 mg/kg (split 100 mg/kg doses, with the first 100 mg/kg dose administered 90 minutes after challenge with Zika virus and the second 100 mg/kg dose delivered 6-8 hours after the first dose) and then twice daily at 25 mg/kg on days 1 through 9 following Zika virus challenge. For Group 2, formulated Compound A was administered by IM on day 0 at 200 mg/kg (split 100 mg/kg doses, with the first 100 mg/kg dose administered 90 minutes after challenge with Zika virus and the second 100 mg/kg dose delivered 6-8 hours after the first dose). For Group 3, vehicle only was administered by IM on the day of Zika virus challenge (+90) and then twice daily on days 1 through 9 following Zika virus challenge.

TABLE 3

| Group | | Treatment | | |
|---|---|---|---|---|
| No. | n | Test Article | Dose (mg/kg) | Route |
| 1 | 5 | Compound A | 200 mg/kg (split dose) on day of Zika challenge and 25 mg/kg b.i.d. each of days 1-9 post Zika challenge | I.M. |
| 2 | 5 | Compound A | 200 mg/kg (split dose) on day of Zika challenge and vehicle b.i.d. each of days 1-9 post challenge | I.M. |
| 3 | 5 | Vehicle | Vehicle on day of Zika virus challenge and b.i.d. each of days 1-9 post challenge | I.M. |

Compound A was well-tolerated in all animals. The results for plasma viremia for Groups 1 to 3 are shown in FIGS. 12A and 12B. All control animals (Group 3) developed high level viremia as detected in blood plasma by day 2 post-infection. Four control animals became viremic by day 2 post-infection and one animal became viremic on day 3 post-infection; viral replication was persistent until day 7 in two animals in Group 3. Animals in Group 1 did not develop detectable viremia as detected in blood plasma through day 28 post-infection. Animals in Group 2 showed significant protection, with only two animals from this group showing viremia as detectable in the blood plasma, with one animal displaying detectable viremia in blood plasma between days 3 to 4 post-infection and the other animal displaying detectable viremia in blood plasma at day 10 post-infection. In both cases for animals in Group 2, the magnitude of viremia was significantly reduced as compared to control (Group 3) and in one case the onset of viremia was significantly delayed as compared to control (Group 3).

Zika virus was also monitored in CSF, saliva and urine for all animals. The results for Group 1 are shown in FIG. 13A, the results for Group 2 in FIG. 13B and the results for Group 3 in FIG. 13C. FIG. 13D shows a summary of the data for Groups 1 to 3 with the shaded bar indicating the number of samples testing positive for Zika virus RNA in CSF, saliva and urine at various time points post-infection. Animals in Groups 1 and 2 showed only sporadically detectable Zika virus RNA in CSF, saliva and urine with viral shedding reduced as compared to control (Group 3).

The presence of the viral RNA in serum (days 0, 7, 14, 21 and 28 post-infection) and CSF (days 0, 3, 7 and 10) of animals in Groups 1 to 3 was also determined after heterologous challenge with the Thai Zika virus isolate. Results are shown as compared to the presence of viral RNA in plasma and CSF after initial infection with the Puerto Rican Zika virus isolate as shown in FIG. 12A (serum) and FIGS. 13 A and B (CSF). The results show the presence of minimal viral RNA present in the serum (FIG. 14A) and CSF (FIG. 14B) indicating a potent peripheral immune response after heterologous challenge was generated in the animals with excellent control of Zika virus RNA levels in plasma and the central nervous system.

In summary, Compound A was well tolerated in NHP and offered significant protection again Zika virus infection and subsequent re-challenge (even with a different strain of Zika virus).

The effect of Compound A on immune system activation was also examined in the NHP animal model. B cell activation and memory T cell activation were examined after the initial challenge on day 0 with the PRVABC-59 Zika virus isolate and after heterologous challenge with a Thai isolate of Zika virus (KF993678) on day 70. Plasma samples were taken on days 0, 7, 14, 21 and 28 for analysis of B cell and memory T cell activation (days post-infection with each Zika virus isolate). Animals were not administered additional doses of Compound A after heterologous challenge with the Thai Zika virus isolate. FIG. 14C shows the effects of Compound A on B cell activation after initial challenge with the Puerto Rican Zika virus isolate and heterologous challenge with the Thai Zika virus isolate in Groups 1 to 3. CD38 expression of naive (CD27−) and memory (CD27+) B cells in plasma samples were determined by flow cytometry (results expressed as geometric mean fluorescence, GMF, $\times 10^4$ of CD38). Solid circles indicate animals that were plasma positive for Zika virus infection and empty circles indicate the animals were plasma negative for Zika virus infection. All animals in Groups 1 to 3 had a Zika virus specific neutralizing antibody response after initial challenge and after heterologous challenge (Groups 1 to 3). As shown in FIG. 14C, all animals showed limited B cell activation after heterologous challenge.

FIG. 14D shows the effects of Compound A on memory T cell activation after the initial challenge on day 0 with the PRVABC-59 Zika virus isolate and heterologous challenge with the Thai Zika virus isolate in Groups 1 to 3. The percentage of CD69+/CD8+T and CD69+/CD4+ effector T cells were determined by flow cytometry. Solid circles indicate animals that were plasma positive for Zika virus infection and empty circles indicate the animals were plasma negative for Zika virus infection. As shown in FIG. 14D, all animals in Groups 1 to 3 showed activated CD8+ and CD4+ T cell response after heterologous challenge.

Figure 14E:
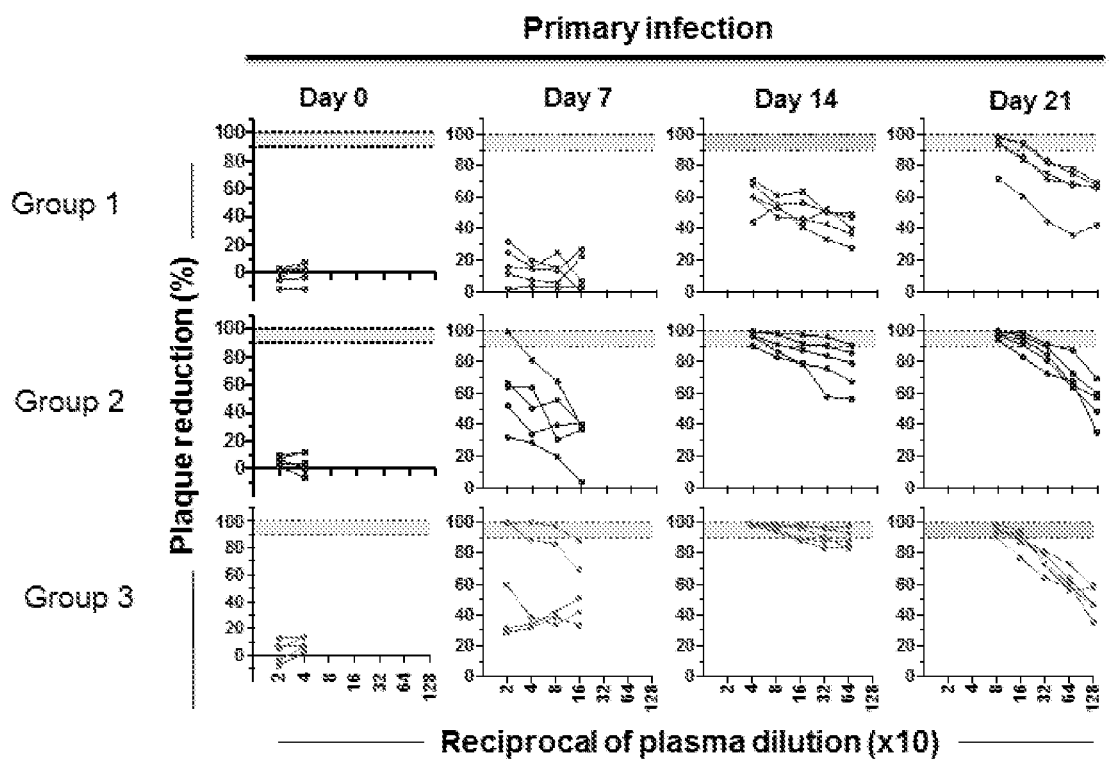
FIG. 14E shows plaque reduction percentage over time in Compound A treatment Groups 1 and 2 and control Group 3 following primary challenge with Zika virus strain PRVABC-59.
Figure 14F:
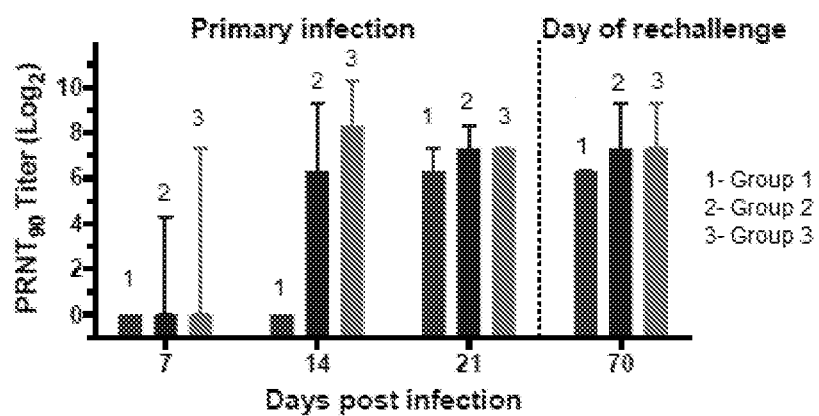
FIG. 14F shows $PRNT_{90}$ titers of neutralizing antibodies over time in Compound A treatment Groups 1 and 2 and control Group 3 following primary challenge with Zika virus strain PRVABC-59.

To assess for the presence of neutralizing antibodies following challenge with the PRVABC-59 Zika virus isolate, a plaque reduction assay was performed. The percentage of plaque reduction and the 90% plaque reducing neutralization titer ($PRNT_{90}$) were determined. The results are shown in FIG. 14E for percentage of plaque reduction by treatment group and in FIG. 14F for $PRNT_{90}$ by treatment group. Groups 1-3 all showed the presence of neutralizing antibodies to Zika virus by day 14 which persisted until day 70. The $PRNT_{90}$ of Groups 1 to 3 was essentially equal on day 70.

Collectively, these results show that treatment with Compound A does not impair the generation of de novo antiviral immune responses.

Example 7—Dose Ranging Studies of Compound A in a Non-Human Primate Zika Virus Model The agent used in this experiment was compound A (the compound of formula I, where A is $NH_2$ and B is H as the HCL salt). The non-human primate (NHP) animals used in this example were as described in Example 6. Animals were pre-screened to be seronegative for simian retrovirus, Herpes B, and filoviruses. Twenty animals (n=20) were used in this example and divided into 5 groups (see Table 4). Four groups of animals (Groups 1 to 4; n=4 for each) were treated with Compound A. The control group (Group 5; n=4) received formulation vehicle only. All animals in Groups 1 to 5 were administered Zika virus Puerto Rican isolate PRVABC-59. Zika virus was administered subcutaneously at a dose of $10^5$ PFU. Animals were monitored throughout the course of the study by sampling whole blood to monitor for the presence of Zika virus. Samples were taken pre-dose and on days 0, 1, 2, 3, 4, 5, 7, 10, 14 and 21 for blood, and pre-dose and on days 0 (approximately 2 hours after the second administration of Compound A) 1 and for pharmacokinetic analysis. Zika virus RNA levels in the plasma were measured.

For Group 1, formulated Compound A was administered by IM on day 0 at 200 mg/kg (split 100 mg/kg doses, with the first 100 mg/kg dose administered 90 minutes after challenge with Zika virus and the second 100 mg/kg dose delivered 6-8 hours after the first dose) and then twice daily at 25 mg/kg on days 1 through 9 post-infection. For Group 2, formulated Compound A was administered by IM on day 0 at 150 mg/kg (split 75 mg/kg doses, timed as in Group 1) and then twice daily at 19 mg/kg on days 1 through 9 post-infection. For Group 3, formulated Compound A was administered by IM on day 0 at 100 mg/kg (split 50 mg/kg doses, timed as in Group 1) and then twice daily at 13 mg/kg on days 1 through 9 post-infection. For Group 4, formulated Compound A was administered by IM on day 0 at 50 mg/kg (split 25 mg/kg doses, timed as in Group 1) and then twice daily at 6 mg/kg on days 1 through 9 post-infection. For Group 5, vehicle only was administered by IM on the same schedule as Groups 1 to 4.

TABLE 4

| Group No. | n | Test Article | Dose (mg/kg) | Route |
|---|---|---|---|---|
| 1 | 4 | Compound A | 200 mg/kg (split dose) on day of Zika challenge and 25 mg/kg b.i.d. each of days 1-9 post Zika challenge | I.M. |
| 2 | 4 | Compound A | 150 mg/kg (split dose) on day of Zika challenge and 19 mg/kg bid. each of days 1-9 post Zika challenge | I.M. |
| 3 | 4 | Compound A | 100 mg/kg (split dose) on day of Zika challenge and 13 mg/kg b.i.d. each of days 1-9 post Zika challenge | I.M. |
| 4 | 4 | Compound A | 50 mg/kg (split dose) on day of Zika challenge and 6 mg/kg b.i.d. each of days 1-9 post Zika challenge | I.M. |
| 5 | 4 | Vehicle | Vehicle on day of Zika virus challenge and b.i.d each of days 1-9 post challenge | I.M. |

Figure 15A:
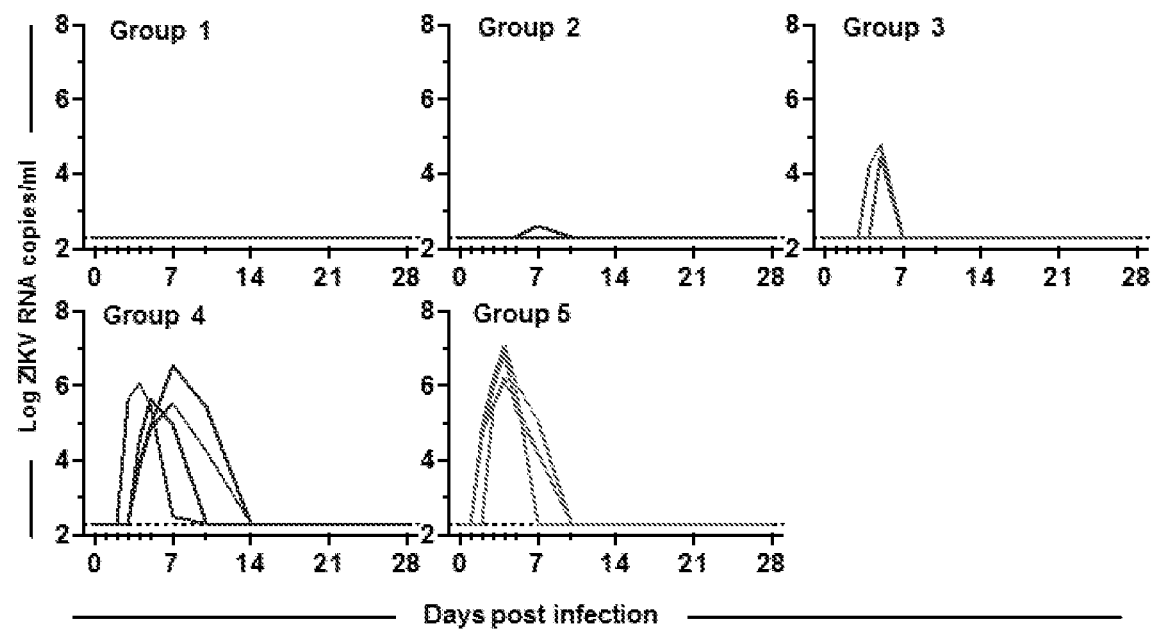
FIG. 15A shows the effect of Compound A treatment (IM administration, post-infection; Groups 1 to 4) or vehicle in Group 5 (control) on the detection of Zika virus RNA in blood samples in non-human primates after subcutaneous infection with Zika strain PRVABC-59.
Figure 15B:
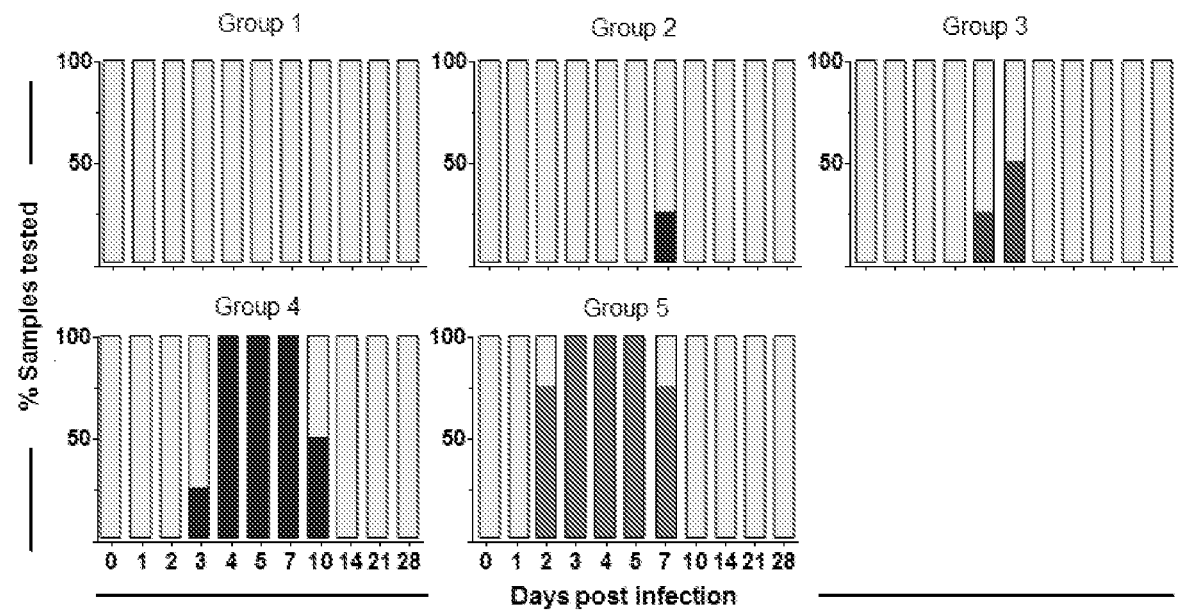
FIG. 15B shows the percentage of blood samples positive for Zika virus RNA over time post-infection in non-human primates following IM administration of Compound A in Groups 1 to 4 (treatment groups) or vehicle in Group 5 (control) after subcutaneous infection with Zika strain PRVABC-59.

Compound A was well-tolerated in all animals. The results for plasma viremia for Groups 1 to 3 are shown in FIGS. 15A and 15B. All control animals (Group 5) developed high level viremia as detected in blood plasma by day 2 post-infection, with all four animals being viremic on day 2 post-infection. Viral replication was persistent until day 7 for all four animals in Group 5. Animals in Group 1 did not develop detectable viremia as detected in blood plasma through day 28 post-infection. Animals in Group 2 showed almost complete protection, with only one animal from this group showing slight viremia detectable on day 7 post-infection. Animals in Group 3 showed significant protection, with only two animals from this group showing slight viremia detectable in the blood plasma, with one animal displaying detectable viremia in blood plasma between days 4 to 5 post-infection and the other animal displaying detectable viremia in blood plasma only on day 5 post-infection. Animals in group 4 were viremic between days 4 to 7 post-infection, with viremia persisting in half the animals through day 10 post-infection. In both cases for animals in Groups 2 and 3 exhibiting viremia, the magnitude of viremia was significantly reduced as compared to control (Group 5) and in one case the onset of viremia was significantly delayed as compared to control (Group 5). No animal in the control group (Group 5) displayed viremia past day 10 post-infection.

In summary, Compound A was well tolerated in NHP and offered significant protection again Zika virus infection at the doses and administration schedule described for Groups 1 to 3.

Figures 15C, 15D:
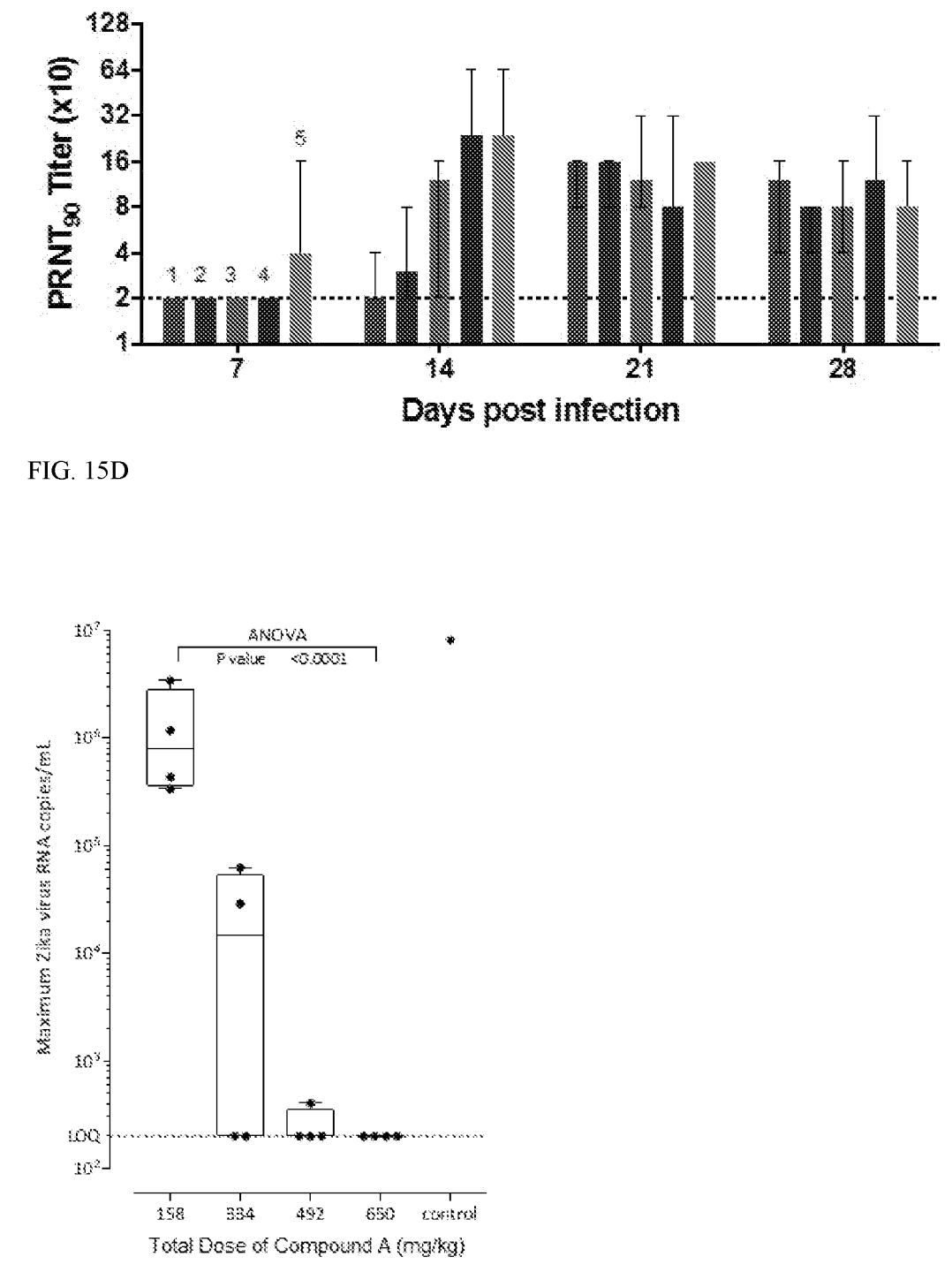

The presence of neutralizing antibodies following challenge with the PRVABC-59 Zika virus isolate was determined as described in Example 6. The results are shown in FIG. 15C. Groups 1-5 all showed the presence of neutralizing antibodies to Zika virus by day 21 post-infection. All animal showed the presence of neutralizing antibodies on day 28 post-infection. These results show that treatment with Compound A does not impair the generation of de novo antiviral immune responses at the doses and administration schedule described for Groups 1 to 4.

Figure 15E:
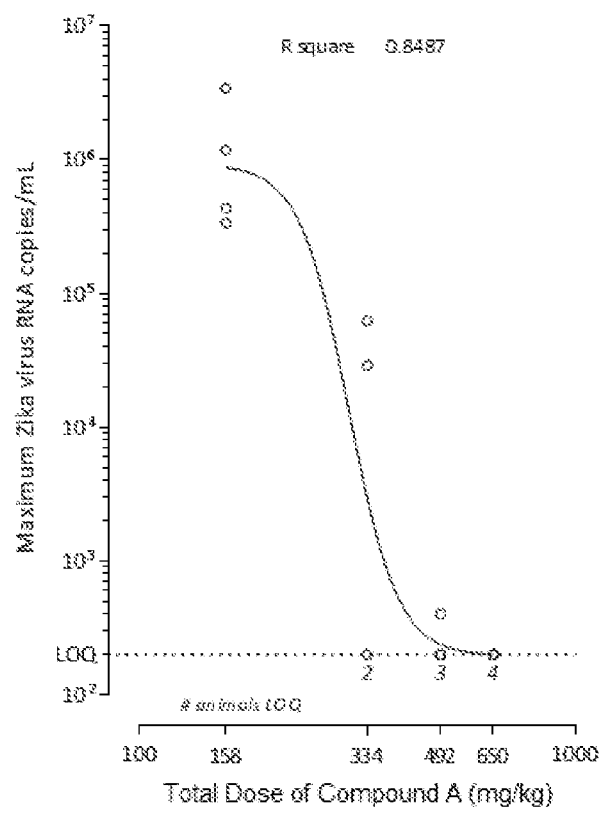
FIG. 15E shows logistic regression of log titer Zika virus RNA by log dose Compound A.

The dose response of Compound A in relation to Zika virus load in the serum of non-human primates was also examined. FIG. 15D shows the maximum titer of Zika virus RNA by total dose (mg/kg) of Compound A administered over the treatment period for Groups 1-4 and for control (Group 5). The results show that at total doses of Compound A greater than 334 mg/kg (Groups 1 to 3), Zika virus titers decreased dramatically and in a statically significant manner (p value<0.0001) as compared to control Zika virus titers. At total doses of compound A of 492 mg/kg (Group 2) and 650 mg/kg (group 1), Zika virus was below the limit of quantification in 3 out of 4 and 4 out of 4 samples, respectively. FIG. 15E shows logistic regression of Zika virus log titer by log dose of Compound A. The numbers at each total dose amount indicate the number of samples that were below the limit of quantification. Consistent with FIG. 15D, administration of a total dose of Compound A greater than 334 mg/kg significantly reduced viral titers.

Example 8—Intramuscular Injection of Compound A in Human Subjects

A phase 1 double-blind, placebo-controlled, dose-ranging study was conducted to evaluate the safety, tolerability, and pharmacokinetics of Compound A administered by intramuscular injection (IM) in healthy human subjects. The study was conducted in two parts. In part 1, subjects received a single dose of Compound A at doses from 0.3 mg/kg to 10 mg/kg via IM administration. Additionally, the effect of lidocaine administration (co-administered with Compound A at a dose of 4 mg/kg) on alleviation of pain associated with injection was also evaluated. In part 2, subjects received Compound A for 7 days (q.d.) at doses of 2.5 mg/kg/day, 5 mg/kg/day or 10 mg/kg/day via IM administration. 50 subjects received single doses of Compound A in part 1 (12 subjects received placebo) and 23 subjects received multiple doses of Compound A in part 2 (6 subjects received placebo). The assignments of subjects to various dosing regimens is shown in Table 5. All planned cohorts were completed.

TABLE 5

| Part 1 | | |
| --- | --- | --- |
| Cohort | Dose (mg/kg) | Number of subjects |
| 1 | 0.3 | 6 active; 2 placebo |
| 2 | 0.75 | 6 active; 2 placebo |
| 3 | 1.8 | 6 active; 2 placebo |
| 4 | 4 | 6 active; 2 placebo |
| 5 | 7 | 6 active; 2 placebo |
| 6 | 10 | 6 active; 2 placebo |
| Lidocaine evaluation | 4 | 14 active |

| Part 2 | | |
| --- | --- | --- |
| Cohort | Dose (mg/kg/day) q.d. for 7 days | Number of subjects |
| 1 | 2.5 | 7 active; 2 placebo |
| 2 | 5 | 8 active; 2 placebo |
| 3 | 10 | 8 active; 2 placebo |

Eligible subjects were adults of either sex ages 18 to 50. Inclusion criteria were: 1) weight≥50 kg (110 lbs) and ≤100 kg (220 lbs); 2) body mass index (BMI) of 19-32 kg/m$^2$; 3) willing to abstain from alcohol consumption for a period of 2 days prior to and during the study; 4) sexually active women of child bearing potential and sexually active men must utilize 2 highly effective contraceptive methods during the study and for a period of time after the study; 5) abstain from caffeinated beverages; 6) normal vital signs at rest; and 7) the ability to provide written informed consent. Exclusion criteria were: 1) subjects who are study site employees, or immediate family members of a study site or sponsor employee; 2) participation in a clinical research study within the previous 90 days; 3) any medical condition or medical history that, in the opinion of the investigator or sponsor, would interfere with the subject's ability to participate in the study or increase the risk of participation for that subject; 4) any screening laboratory test with an abnormal result that is grade 1 (mild) or greater; 5) abnormal ECG (defined as any screening or baseline QTc>450 msec, PR>200 msec, or ventricular and/or atrial premature contractions that are more frequent than occasional, and/or as couplets or higher in grouping; 6) an abnormal cardiovascular exam including a confirmed elevated blood pressure at screening (systolic greater than 140, diastolic greater than 90) after 5 minutes of supine rest, tachycardia>100 bpm after 5 minutes of supine rest; 7) family or personal history of sudden death or QT prolongation; 8) use of prescription, over-the-counter (OTC) medications or herbal supplements, with the exception of acetaminophen and non-oral hormonal contraception, for a period of 7 days prior to and during the study; 9) inadequate muscle mass to receive IM injections; 10) history of alcohol or drug abuse within the previous year, or current evidence of substance dependence or abuse; 11) current smokers or history of smoking within the last 12 months; 12) serious adverse reaction or serious hypersensitivity to any drug; 13) presence or history of clinically significant allergy requiring treatment, as judged by the investigator. Hayfever is allowed unless it is active; 14) donation or loss of greater than 400 mL of blood within the previous 3 months; 15) positive serology for hepatitis B surface antigen, hepatitis C antibody, or human immunodeficiency virus (HIV) type 1; 16) pregnant or nursing females; and 17) male subjects with pregnant female partners.

Results

The plasma concentration time profile of Compound A was determined for each subject in part 2 (results expressed as ng/ml Compound A). Blood samples were taken on Day 1 prior to administration of the first dose and at 1, 2, 3, 4, 6, 8, 10, 12, 16 and 24 hours after administration of the first dose of Compound A and on Day 7 prior to administration of the last dose of Compound A and at 1, 2, 3, 4, 6, 8, 10, 12, 16, 24, 36, 48, 72 and 96 hours after administration of the last dose of Compound A. Plasma samples were obtained from the blood samples and the concentration of Compound A determined.

Figure 16A:
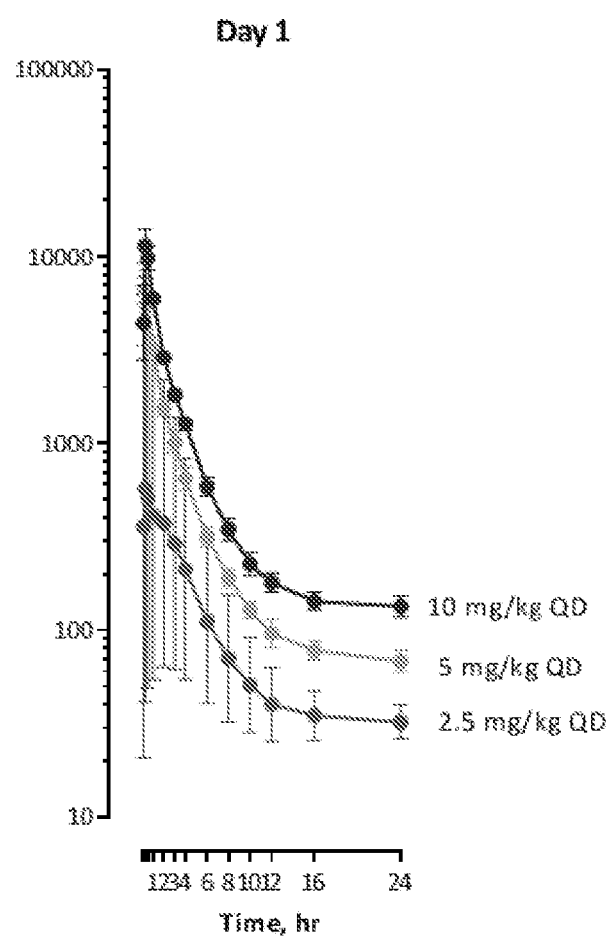
FIG. 16A shows the plasma PK profile of Compound A administered to human subjects by IM injection following the first dose of Compound A on day 1 (results expressed as ng/ml Compound A).
Figure 16B:
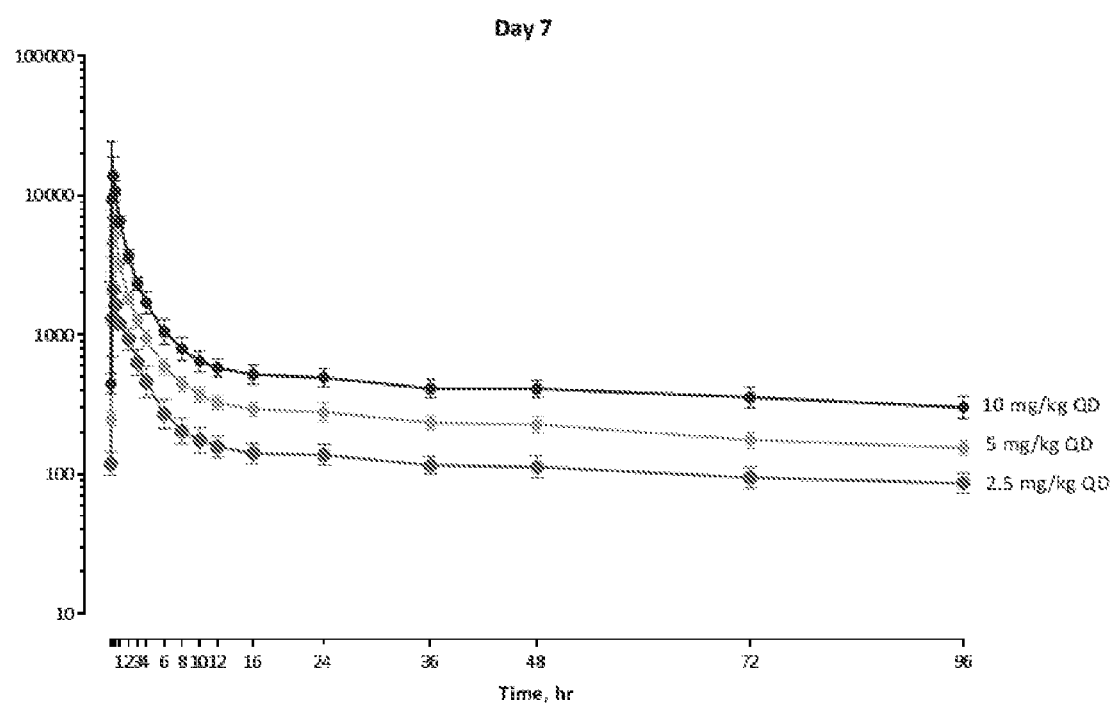
FIG. 16B shows the plasma PK profile of Compound A administered to human subjects by IM injection following the last dose of Compound A on day 7 (results expressed as ng/ml Compound A).

The results are shown in FIG. 16A for Day 1 and FIG. 16B for Day 7. The results are shown as geometric mean (95% CI) and expressed as ng/ml Compound A. As can be seen in FIGS. 16A and 16B, exposure was dose-proportional and linear with increasing dose. Plasma concentrations of Compound A were maximal 1 to 2 hours after administration.

For both part 1 and part 2, no serious or severe adverse events occurred and no clinically significant laboratory abnormalities occurred at any dose. Co-administration of lidocaine with Compound A was found to ameliorate injection site pain, without altering the plasma PK profile of Compound A (data not shown).

Example 9—Model of Intravaginal Administration of Zika Virus

Zika virus infections can be spread through sexual contact. An animal model of Zika virus infection by the vaginal route was used to determine differences in viremia of Zika virus based on the manner of infection. The non-human primate animals used in this example were captive-bred Indian rhesus macaques as described in Example 6. Female animals (n=4) were administered Zika virus Puerto Rican isolate PRVABC-59 via intravaginal administration at a dose of $10^5$ PFU (the same dose used for subcutaneous administration in Examples 6 and 7). Animals were monitored visually throughout the course of the study. Blood, CSF and CVL samples were taken to monitor for the presence of Zika virus and to assess pharmacokinetic, pharmacodynamic, immune activation and virology parameters. Blood samples were taken pre-dose and on days 0, 1, 2, 3, 4, 5, 7, 10, 14, 21 and 28 for determination of Zika virus RNA levels, immune activation (only to day 21) and virology parameters, and pre-dose and on days 0 (approximately 2 hours after the second administration of Compound A), 1 and 7 for pharmacokinetic and pharmacodynamic analysis. CSF samples were taken on days 0 7, 14, 21 and 28 (via lumbar puncture) and CVL samples were taken on days 0, 3, 7, 14, 21, and 28 (via cervicovaginal swab) for determination of Zika virus RNA levels and virology parameters.

Figure 12A:
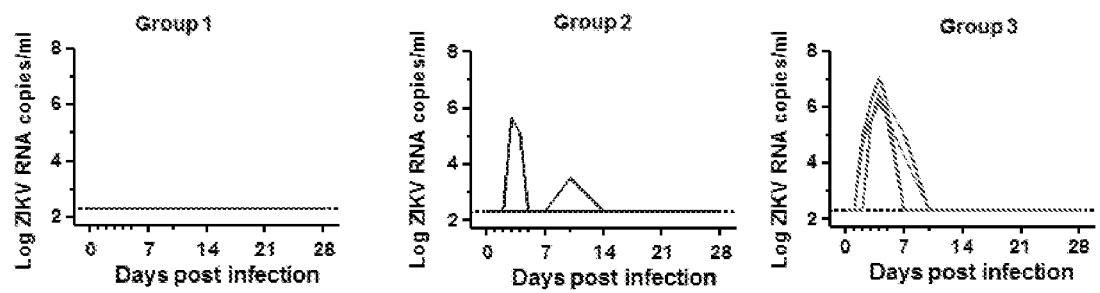
FIG. 12A shows the effect of IM administration of Compound A in Groups 1 and 2 (treatment groups) and of vehicle in Group 3 (control) on the presence of Zika virus RNA in the plasma of non-human primates after subcutaneous infection with Zika strain PRVABC-59.
Figure 12B:
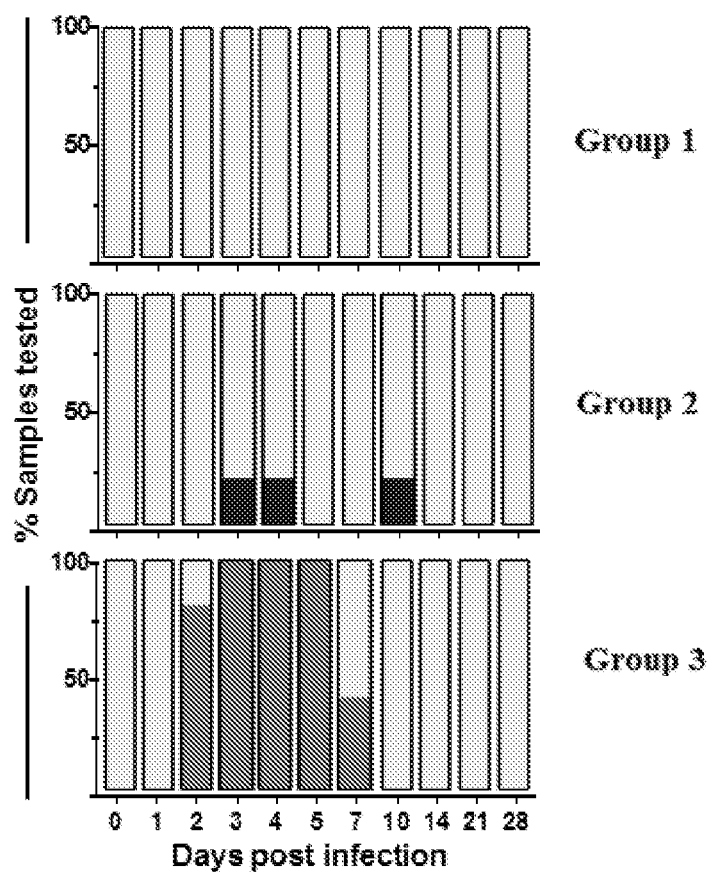
FIG. 12B shows the percentage of plasma samples positive for Zika virus RNA over time post-infection in non-human primates following IM administration of Compound A in Groups 1 and 2 (treatment groups) and of vehicle in Group 3 (control) after subcutaneous infection with Zika strain PRVABC-59.
Figure 17:
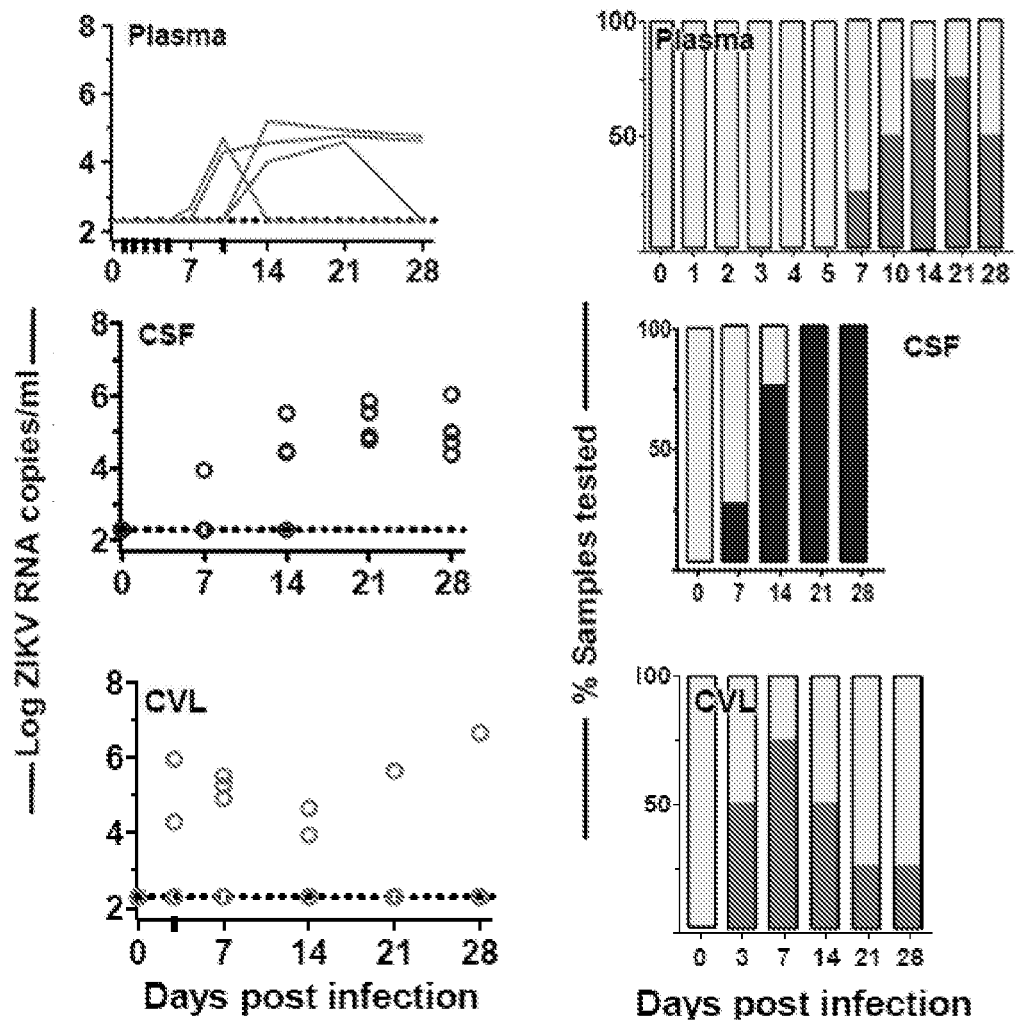
FIG. 17 shows the appearance of Zika virus RNA in the blood, CSF and cervicovaginal fluid in non-human primates after intravaginal infection with Zika strain PRVABC-59.

As shown below, rhesus macaques were susceptible to Zika virus infection via intravaginal administration. At the administered dose, animals were viremic as determined by detection of Zika virus RNA in the blood between days 7 to 10 days post-infection with peak viremia occurring after 10 post-infection. Furthermore, Zika virus RNA was detected in the blood of two animals at 28 days post-infection (FIG. 17). When compared with subcutaneous administration of Zika virus at the same dose (shown in FIGS. 12A and 12B of Example 6), it becomes apparent that subcutaneous administration results in a more rapid appearance of Zika RNA in the blood (viremia detectable between days 2 to 7 post-infection, with peak viremia occurring around day 5 post-infection). No Zika virus RNA was detectable in the blood after subcutaneous administration after day 7 post-infection showing a more rapid clearance of Zika virus after subcutaneous administration. Further comparison of the data indicate that total Zika virus burden in the blood was lower in animals infected with Zika virus by intravaginal administration (Log Zika virus RNA copies/ml less than 5 at peak viremia) as compared to subcutaneous administration (Log Zika virus RNA copies/ml between 6 and 7 at peak viremia).

Figure 13A:
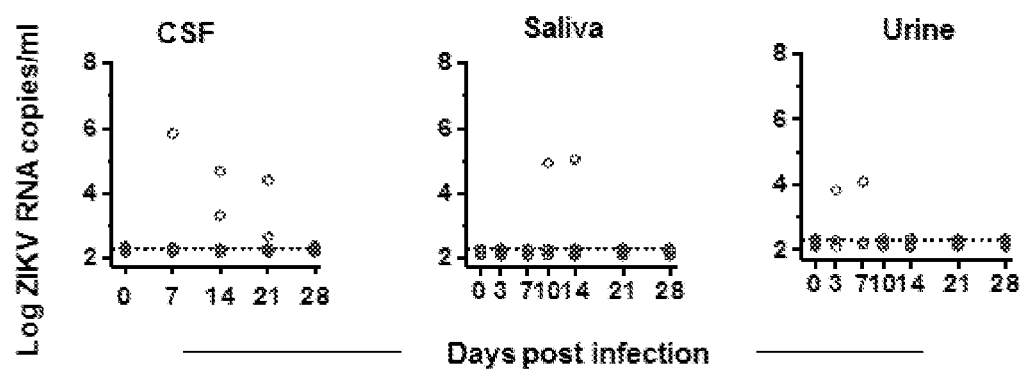
FIG. 13A shows the effect of Compound A treatment (IM administration, post-infection; Group 1) on the detection of Zika virus RNA in cerebrospinal fluid, saliva and urine in non-human primates after subcutaneous infection with Zika strain PRVABC-59.
Figure 13B:
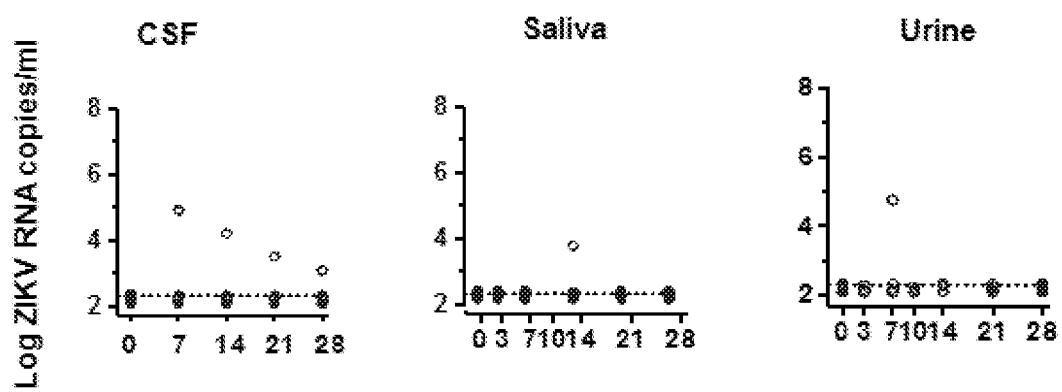
FIG. 13B shows the effect of Compound A treatment (IM administration, post-infection; Group 2) on the detection of Zika virus RNA in cerebrospinal fluid, saliva and urine in non-human primates after subcutaneous infection with Zika strain PRVABC-59.
Figure 13C:
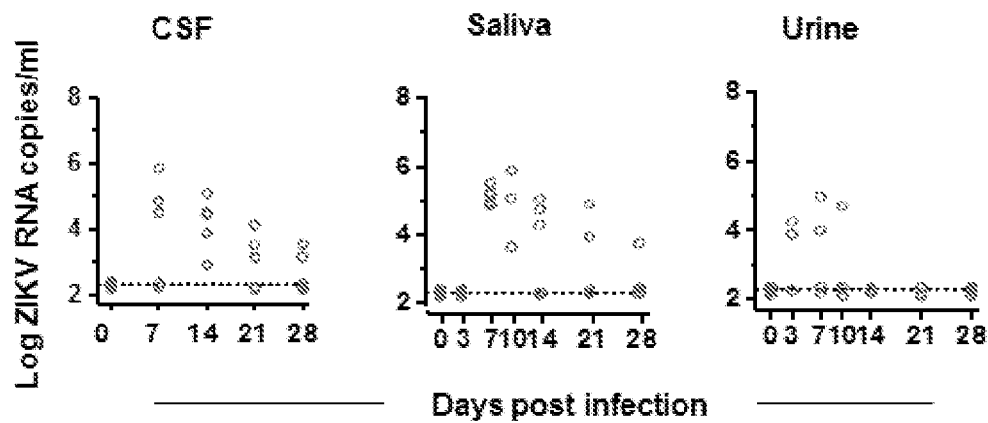
FIG. 13C shows the effect of control treatment (Group 3) on the detection of Zika virus RNA in cerebrospinal fluid, saliva and urine in non-human primates after subcutaneous infection with Zika strain PRVABC-59.
Figure 13D:
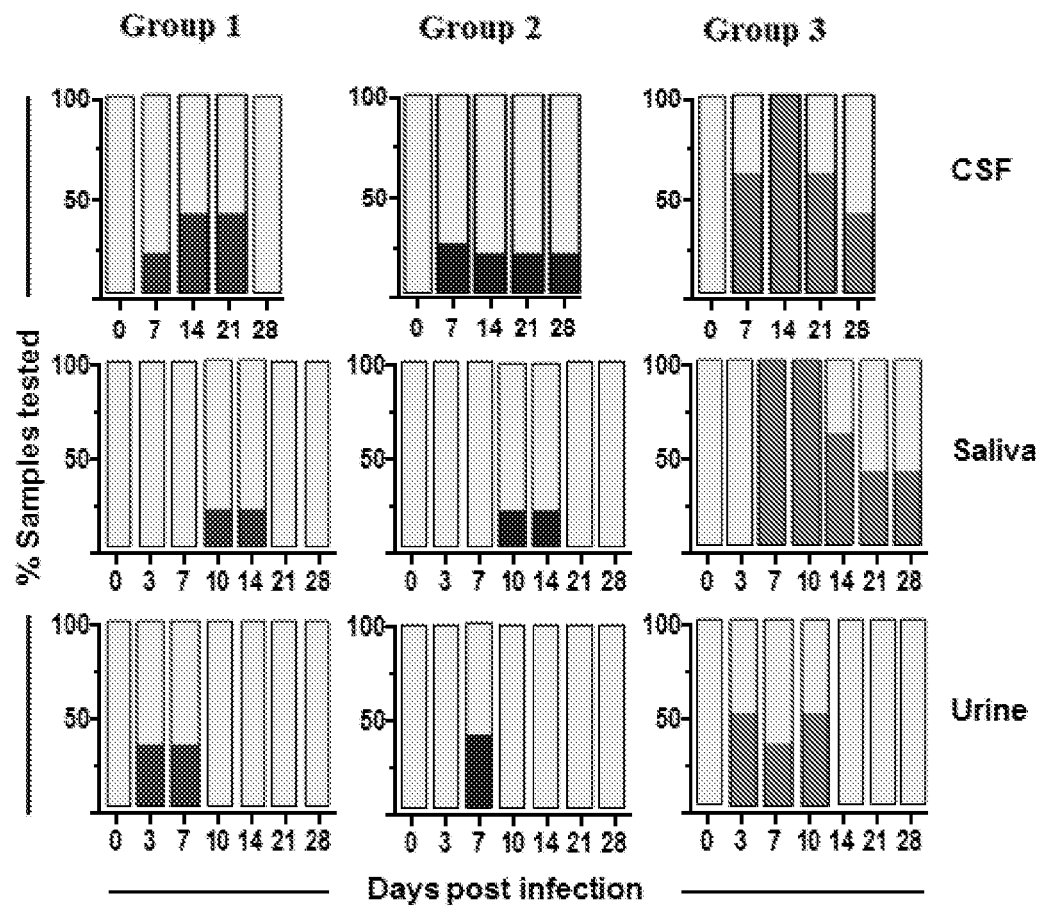
FIG. 13D shows the percentage of cerebrospinal fluid, saliva and urine samples positive for Zika virus RNA over time post-infection in non-human primates following IM administration of Compound A in Groups 1 and 2 (treatment groups) or vehicle in Group 3 (control) after subcutaneous infection with Zika strain PRVABC-59.

With regard to CSF, intravaginal administration of Zika virus resulted in detection of Zika virus RNA in the CSF beginning on day 7 post-infection (1 animal) and continuing through day 28 post-infection (all 4 animals) as shown in FIG. 17. Total Zika virus burden also increased through days 21 post-infection and remained elevated on day 28 post-infection. When compared with subcutaneous administration of Zika virus at the same dose (shown in FIGS. 13C and 13D of Example 6), it becomes apparent that subcutaneous administration results in a more rapid appearance of Zika RNA in the CSF (Zika virus RNA detectable in three animals on day 7 post-infection versus 1 by intravaginal administration) and a more rapid clearance of Zika virus from the CSF (2 animals with detectable Zika virus on day 28 post-infection versus 4 animals by intravaginal administration). Furthermore, the data show that total Zika virus burden in the CSF was lower in animals infected with Zika virus by subcutaneous administration at later time points (Log Zika virus RNA copies/ml around 3 at day 28 post-infection) as compared to intravaginal administration (Log Zika virus RNA copies/ml around 5 at day 28 post-infection).

In summary, intravaginal exposure to Zika virus results in delayed and more persistent viral replication in the blood and CSF as compared to subcutaneous exposure. Furthermore, the total viral burden in the blood after intravaginal exposure is less than that seen with subcutaneous exposure. Total viral RNA detected in the CSF was comparable at peak levels in intravaginal and subcutaneous administration, but Zika virus RNA was detectable at higher levels at later time points after intravaginal exposure.

Intravaginal administration also resulted in earlier viral replication in the vaginal mucosa as compared to the blood and CSF (FIG. 17). The data show that the levels of Zika virus detected in CVL are higher than in the blood indicating a higher level of viral replication in the vaginal mucosa. Viral RNA was detectable in 1 animal at days 21 and 28 post-infection.

These results indicate that the kinetics of Zika virus infection are different and dependent on the manner in which a subject is exposed to Zika virus. Intravaginal exposure, such as through sexual intercourse with an infected partner, results in the delayed presence of Zika virus in the blood and CSF, but a more persistent viral replication. These data indicate the treatment window for treatment of Zika virus infection may be broader when Zika exposure occurs through intravaginal exposure than through subcutaneous exposure (as would occur when bitten by a mosquito).

Example 10—Model of Intravaginal Administration of Zika Virus With Delayed Administration of Compound in Non-Human Primates The agent used in this experiment will be compound A (the compound of formula I, where A is $NH_2$ and B is H as the HCL salt). The non-human primate animals used in this example will be captive-bred Indian rhesus macaques as described in Example 6 Animals will be pre-screened to be seronegative for simian retrovirus, Herpes B, and filoviruses. Fifteen animals (n=15) will be used in this study and will be divided into 3 groups (see Table 6). Two groups of animals (Groups 1 and 2; n=5 for each) will be treated with Compound A at varying times after intravaginal infection with Zika virus. The control group (Group 3; n=5) will receive the same dose of Zika virus by the same route of administration and formulation vehicle only. All animals in Groups 1 to 3 will be administered Zika virus Puerto Rican isolate PRVABC-59 on day 0 of the study. Zika virus will be administered intravaginally at a dose of $10^5$ PFU. Animals will be monitored visually throughout the course of the study. Blood, CSF and CVL samples will be taken to monitor for the presence of Zika virus and to assess pharmacokinetic, pharmacodynamic, immune activation and virology parameters. Blood samples will be taken pre-dose and on days 0, 1, 2, 3, 4, 5, 7, 10, 14, 21 and 28 for determination of Zika virus RNA levels, immune activation (only to day 21) and virology parameters, and pre-dose and on days 0 (approximately 2 hours after the second administration of Compound A), 1 and 7 for pharmacokinetic and pharmacodynamic analysis. CSF samples will be taken on days 0, 7, 14, 21 and 28 (via lumbar puncture) and CVL samples will be taken on days 0, 3, 7, 14, 21, and 28 (via cervicovaginal swab) for determination of Zika virus RNA levels and virology parameters. Samples of other bodily fluids, such as, but not limited to, urine and saliva, may also be taken according to one of the schedules above or according to a different schedule.

For Group 1, formulated Compound A will be administered by IM at 96±1 hr post-infection at 200 mg/kg (split 100 mg/kg doses, with the second dose delivered 6-8 hours after the first dose) and then twice daily at 25 mg/kg on days 5 through 13 post-infection. For Group 2, formulated Compound A will be administered by IM at 120±1 hr post-infection at 200 mg/kg (split 100 mg/kg doses, with the second dose delivered 6-8 hours after the first dose) and then twice daily at 25 mg/kg on days 6 through 14 post-infection. For Group 3, vehicle only will administered by IM twice daily on the day of Zika virus infection and on days 1-9 post-infection.

TABLE 6

Treatment

| Group No. | n | Test Article | Dose (mg/kg) | | Route |
|---|---|---|---|---|---|
| 1 | 5 | Compound A | 200 mg/kg (split dose) on day 4 post Zika challenge and 25 mg/kg b.i.d. each of days 5-13 post Zika challenge | 96 hrs post-infection | I.M. |
| 2 | 5 | Compound A | 200 mg/kg (split dose) on day 5 post Zika challenge and 25 mg/kg b.i.d. each of days 6-14 post Zika challenge | 120 hrs post-infection | I.M. |
| 3 | 5 | Vehicle | Vehicle b.i.d, on day of Zika virus challenge and b.i.d each of days 1-9 post Zika challenge | Vehicle only | I.M. |

The primary endpoint for this study will be reduction of plasma viremia. In the absence of treatment, at the dose of Zika virus administered plasma viremia is readily detectable in 100% of the animals. The study will measure the reduction of Zika virus RNA in the blood after Zika challenge and administration of Compound A as described in Table 6. The pharmacokinetic and pharmacodynamic responses of Compound A (Groups 1-2) in the NHP model will also be assessed. Antiviral modeling using pharmacokinetic, pharmacodynamic and viral load data will also be performed. Various immune system parameters will also be measured by flow cytometry (percent NK cells subsets and their level of activation, percent monocyte cells subsets and their level of activation, and percent naïve, central memory, effector/effector memory CD4+ and CD8+ T cell subsets and activation levels) as well as the production of neutralizing antibodies to Zika virus.

Example 11—Delayed Administration Model in Non-Human Primates

The agent used in this experiment will be compound A (the compound of formula I, where A is NH$_2$ and B is H as the HCL salt). The non-human primate (NHP) animals to be used in this example is as described in Example 6. Animals will be pre-screened to be seronegative for simian retrovirus, Herpes B, and filoviruses. Twenty animals (n=20) will be used in this study and will be divided into 5 groups (see Table 7). Three groups of animals (Groups 1 to 3; n=5 for each) will be treated with Compound A at varying times after infection with Zika virus. The control group (Group 4; n=5) will receive the same dose of Zika virus and formulation vehicle only. All animals in Groups 1 to 4 will be administered Zika virus Puerto Rican isolate PRVABC-59 on day 0 of the study. Zika virus will be administered subcutaneously at a dose of $10^5$ PFU. Animals will be monitored visually throughout the course of the study. Blood samples will be taken to monitor for the presence of Zika virus and to assess pharmacokinetic, pharmacodynamic, immune activation and virology parameters. Blood samples will be taken pre-dose and on days 0, 1, 2, 3, 4, 5, 7, 10, 14 and 21 for determination of Zika virus RNA levels, immune activation and virology parameters, and pre-dose and on days 0 (approximately 2 hours after the second administration of Compound A), 1 and 7 for pharmacokinetic and pharmacodynamic analysis.

For Group 1, formulated Compound A will be administered by IM at 24±1 hr post-infection at 200 mg/kg (split 100 mg/kg doses, with the second dose delivered 6-8 hours after the first dose) and then twice daily at 25 mg/kg on days 2 through 10 post-infection. For Group 2, formulated Compound A will be administered by IM at 48±1 hr post-infection at 200 mg/kg (split 100 mg/kg doses, with the second dose delivered 6-8 hours after the first dose) and then twice daily at 25 mg/kg on days 3 through 11 post-infection. For Group 3, formulated Compound A will be administered by IM at 72±1 hr post-infection at 200 mg/kg (split 100 mg/kg doses, with the second dose delivered 6-8 hours after the first dose) and then twice daily at 25 mg/kg on days 4 through 12 post-infection. For Group 4, vehicle only will administered by IM twice daily on the day of Zika virus infection and on days 1-9 post-infection.

TABLE 7

Treatment

| Group No. | n | Test Article | Dose (mg/kg) | | Route |
|---|---|---|---|---|---|
| 1 | 5 | Compound A | 200 mg/kg (split dose) on day 1 post Zika challenge and 25 mg/kg b.i.d. each of days 1-10 post Zika challenge | 24 hrs post-infection | I.M. |
| 2 | 5 | Compound A | 200 mg/kg (split dose) on day 2 post Zika challenge and 25 mg/kg b.i.d. each of days 3-11 post Zika challenge | 48 hrs post-infection | I.M. |
| 3 | 5 | Compound A | 200 mg/kg (split dose) on day 3 post Zika challenge and 25 mg/kg b.i.d. each of days 4-12 post Zika challenge | 72 hrs post-infection | I.M. |
| 4 | 5 | Vehicle | Vehicle on day of Zika virus challenge and b.i.d each of days 1-9 post Zika challenge | Vehicle only | I.M. |

The primary endpoint for this study will be reduction of plasma viremia. In the absence of treatment, at the dose of Zika virus administered plasma viremia is readily detectable in 100% of the animals. The study will measure the reduction of Zika virus RNA in the blood after Zika challenge and administration of Compound A as described in Table 7. The pharmacokinetic and pharmacodynamic responses of Compound A (Groups 1-3) in the NHP model will also be assessed. Antiviral modeling using pharmacokinetic, pharmacodynamic and viral load data will also be performed. Various immune system parameters will also be measured by flow cytometry (percent NK cells subsets and their level of activation, percent monocyte cells subsets and their level of activation, and percent naïve, central memory, effector/effector memory CD4+ and CD8+ T cell subsets and activation levels) as well as the production of neutralizing antibodies to Zika virus.

Methods

Viruses

The MR-766 isolate of Zika virus was collected from a sentinel rhesus monkey in the Zika forest of Uganda in April 1947 and the P 6-740 strain was collected from mosquitos in Malaysia in July 1966. These two Zika virus strains were kindly provided by Robert B. Tesh (University of Texas Medical Branch, Galveston, Tex.). The Zika virus PRVABC-59 strain was isolated in Puerto Rico from the blood of a human patient in December 2015. The virus was originally provided by Barbara Johnson (Centers for Disease Control and Prevention, Fort Collins, Colo.). The Zika virus strain KF993678 was isolated in Canada in 2103 from the blood of a human patient who had recently vacationed in Thailand. Virus strains were amplified once or twice in Vero cells and had titers of $10^{7.7}$, $10^{6.7}$ and $10^{7.5}$ 50% cell culture infectious doses ($CCID_{50}$)/mL, for MR-766, P 6-740 and PRVABC-59, respectively. The Malaysian P6-740 strain was titrated for lethality in AG129 mice and used for the present animal study.

Mouse Model

A mouse model of Zika virus infection and disease was characterized. Male and female AG129 mice between 8 and 10 weeks were infected subcutaneously (s.c.) with Zika virus (P6-740). A dose titration of virus was performed to determine a suitable challenge dose of virus for model characterization and antiviral/vaccine studies.

A model characterization study was conducted to identify key time-points of virus replication in various tissues. A cohort of animals was included where survival and weight were monitored to demonstrate consistency with these parameters. Two male and two female mice were necropsied 1, 3, 5, 7, 9, 11 and 13 days after virus challenge. Tissues, including serum, spleen, liver, kidney, brain, testes/uterus, and urine were collected from each animal Part of each tissue was fixed in 4% paraformaldehyde or neutral buffered formalin for at least 24 hours prior to paraffin embedding and sectioning for use in immunohistochemistry analysis described above. Total RNA was extracted from tissues and Zika virus RNA was quantified as described above.

For Zika virus infection and antiviral treatment studies, mice were randomly assigned to groups of 10 animals each. A $10^{-3}$ dilution ($10^{4.0}$ pfu/mL) of the virus was prepared in MEM. Mice were challenged s.c. with 0.1 mL of the diluted virus (~$10^{3.0}$ pfu/animal). All compound dosages were based on an average mouse weight of 22 g. Compounds were prepared in sterile saline less than 18 hours prior to initial administration in mice and stored at 4° C. for the duration of the study. Compound A was administered i.m., twice daily (bid) at 300 or 150 mg/kg/d. Ribavirin was given i.p., bid at 75 or 50 mg/kg/d. Treatments began 4 hours prior to virus challenge and continued for 8 days. The identity of the treatment groups was blinded to the technician administering treatments. Mortality was observed twice daily for 28 days, and the weight of each mouse was recorded on day 0 and then every other day from 1-19 days post-virus infection (dpi). Mice were humanely euthanized if they could no longer right themselves or were unresponsive to stimuli.

Real-Time RT-PCR for the Detection of Zika Virus RNA

Fifty to 100 mg of freshly isolated tissue was ground with a pestle in 1 mL TRI Reagent (Sigma-Aldrich, St. Louis, Mo.) and total RNA was extracted. For the extraction of viral RNA from liquid samples, QIAamp Viral RNA Mini Spin kit was used according to the manufactures instructions (Qiagen, Valencia, Calif.). Extracted RNA was eluted with nuclease-free water and was amplified by a quantitative real-time RT-PCR using the Logix Smart Zika Test developed by Co-Diagnostics, Inc. (Bountiful, Utah). Five μL of the master mix containing a set of primers and Rapid Probe, labeled with a FAM fluorophore and DABCYL quencher, was mixed with 2-5 μL of RNA and an appropriate volume of water for a final reaction volume of 10 μl. RNA was first reverse transcribed for 10 minutes at 55° C., followed by strand separation by heating to 95° C. for 20 seconds. The PCR reaction consisted of 40 cycles at 95° C. for 1 second and 55° C. for 20 seconds. A standard curve was generated with a synthetic RNA spanning the region of amplification and it was used to calculate the number of genome equivalents of the unknown samples.

Flow Cytometry

Flow cytometry was performed as described in Osuna, et al. (Nat Med, PMID 27694931, October 2016), which is hereby incorporated by reference for such teaching.

Plaque Reduction Assay

Plaque reduction assay was performed as described below. Briefly, NHP blood plasma samples were collected, heat inactivated and stored at −80° C. NHP plasma and positive control ZIKV-neutralizing sera (of known titer) were serially diluted. Undiluted and diluted samples were added to an equal volume of 2,000 PFU/ml of ZIKV (Puerto Rico PRVABC59). The virus-antibody mixture was incubated at 37° C. for 1 h before 100 μl (100 PFU ZIKV) was added to each well of a confluent 6-well tissue-culture dish seeded with Vero cells. After a 1-h virus adsorption at 37° C., cells were overlaid with 1% noble agar in supplemented minimal essential medium (MEM). At 4 d after infection, an additional overlay with 0.02% (wt/vol) neutral red in MEM with 1% agar was added, and plaques were counted and recorded the following day. The assay was performed in triplicate and control wells were also incorporated. The neutralizing-antibody titer was expressed as the maximum dilution of blood plasma that yielded a 90% plaque reduction ($PRNT_{90}$).

Statistical Analysis

Survival data were analyzed using the Wilcoxon log-rank survival analysis and all other statistical analyses were performed using one-way ANOVA using a Bonferroni group comparison (Prism 5, GraphPad Software, Inc).

What is claimed is:

1. A method of reducing the transmission of a Zika virus infection from a first subject to a second subject, the method comprising the step of administering to the first subject or the second subject an effective amount of a compound of formula I or a pharmaceutically acceptable salt, hydrate or solvate thereof (Structure of formula (I): a pyrrolo-pyrimidine nucleoside analog with substituents A and B, and a sugar-like ring bearing HO—CH2, two OH groups, and an NH in the ring.)

wherein A is OH or NH₂, and B is H or NH₂.

2. The method of claim 1, wherein A is NH₂ and B is H.
3. The method of claim 1, wherein the second subject is a sexual partner of the first subject.
4. The method of claim 1, wherein the first subject is a male and the second subject is a female.
5. The method of claim 4, wherein the Zika virus infection is transmitted from the first subject to the second subject through transmission of a bodily fluid of the first subject to the second subject.
6. The method of claim 5, wherein the bodily fluid is blood, semen, seminal fluid, or saliva.
7. The method of claim 4, wherein the compound of formula I is administered to the second subject.
8. The method of claim 7, wherein transmission of the Zika virus by the second subject is reduced.
9. The method of claim 1, wherein the first subject is a female and the second subject is an infant or a prenatal human.
10. The method of claim 9, wherein the Zika virus infection is transmitted from the first subject to the second subject through transmission of a bodily fluid of the first subject to the second subject.
11. The method of claim 10, wherein the bodily fluid is blood, blood plasma, blood serum, amniotic fluid, breast milk, vaginal secretions, urine, amniotic fluid, or saliva.
12. The method of claim 9, wherein the compound of formula I is administered to the first subject.
13. The method of claim 12, wherein the administration reduces a viral titer of the Zika virus in a bodily fluid of the first subject.
14. The method of claim 13, wherein the bodily fluid is blood, blood plasma, blood serum, amniotic fluid, breast milk, vaginal secretions, urine, amniotic fluid, or saliva.
15. The method of claim 1, wherein the compound of formula I is administered to the first subject or the second subject after the first or second subject has been infected with the Zika virus infection or after the first or second subject has been infected with the Zika virus and before the Zika virus infection can be detected.
16. The method of claim 1, wherein a single dose of the compound of formula I is administered during a course of treatment.
17. The method of claim 1, wherein more than one dose of the compound of formula I is administered during a course of treatment.
18. The method of claim 17, wherein the course of treatment comprises administering at least one dose as a loading dose and at least one dose as a maintenance dose.
19. The method of claim 1, wherein the compound of formula I is administered by intravenous administration, intramuscular administration, parenteral administration, oral administration or a combination of the foregoing.
20. A method for reducing a viral titer of a Zika virus in a bodily fluid, tissue or cell of a subject, the method comprising the step of administering to the subject an effective amount of a compound of the formula 1 or a pharmaceutically acceptable salt, hydrate or solvate thereof (Formula (I) repeated)

wherein A is OH or NH₂, and B is H or NH₂.

21. A method of treating or suppressing a disease or condition associated with a Zika virus infection in a subject, the method comprising the step of administering to the subject an effective amount of a compound of the formula I or a pharmaceutically acceptable salt, hydrate or solvate thereof (Formula (I) repeated)

wherein A is OH or NH₂, and B is H or NH₂.

22. The method of claim 21, wherein the disease or condition is a neurological complication, an auto-immune disease, Guillain-Barré syndrome, or and microcephaly.

* * * * *